United States Patent
Horie et al.

(10) Patent No.: US 6,890,531 B1
(45) Date of Patent: May 10, 2005

(54) NEURONAL GROWTH FACTOR GALECTIN-1

(75) Inventors: Hidenori Horie, Kanagawa (JP); Yoshimasa Inagaki, Gunma (JP); Yoshiaki Sohma, Gunma (JP); Toshihiko Kadoya, Gunma (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/744,931

(22) PCT Filed: Jul. 29, 1999

(86) PCT No.: PCT/JP99/04091
§ 371 (c)(1),
(2), (4) Date: May 7, 2001

(87) PCT Pub. No.: WO00/06724
PCT Pub. Date: Feb. 10, 2000

(30) Foreign Application Priority Data

Jul. 31, 1998 (JP) .......................................... 10/218216

(51) Int. Cl.$^7$ ...................... A61K 39/395; A61K 38/00; G01N 33/567; G01N 33/544; C07K 14/00
(52) U.S. Cl. .................... 424/130.1; 436/503; 436/529; 530/350; 930/280; 514/2
(58) Field of Search ...................... 424/130.1; 436/503, 436/529; 530/350; 435/252.1, 320.1; 514/2; 930/280

(56) References Cited

U.S. PATENT DOCUMENTS 5,693,760 A    12/1997 Seilhammer et al. ....... 530/396

FOREIGN PATENT DOCUMENTS

| EP | 0 337 799 | 10/1989 |
|----|-----------|---------|
| WO | 98/08535  | 3/1998  |

OTHER PUBLICATIONS

Chrispeels and Raikhel, 1991, The Plant Cell, 3: 1–9.*
Hirabayashi, et al, 1993, Accession No CAA32938.*
Tracey et al., "Subunit Molecular Mass Assignment of 14,654 Da To The Soluble β–Galactoside–Binding Lectin From Bovine Heart Muscle And Demonstration Of Intramolecular Disulfide Bonding Associated With Oxidative Inactivation", *The Journal of Biological Chemistry*, The American Society for Biochemistry and Molecular Biology, Inc., vol. 267(15):10342–10347, (1992).

Barondes et al., "Galectins: A Family Of Animal β–Galactoside–Binding Lectins", *Cell*, Cell Press, vol. 76:597–598, (1994).

Kasai et al., "Galectins: A Family Of Animal Lectins That Decipher Glycocodes", *J. Biochem.*, vol. 119(1):1–8, (1996).

Yamaoka et al., "Structural And Functional Characterization Of A Novel tumor–Derived Rat Galectin–1 Having Transforming Growth Factor (TGF) Activity: the Relationship Between Intramolecular Disulfide Bridges And TGF Activity", *J. Biochem.*, vol. 119:878–886, (1996).

Puche et al., "Role of Galectin–1 in the Developing Mouse Olfactory System", Development Biology, Article No. 0257, 1996, pp. 274–287, vol. 179, Academic Press, Inc.

Clerch et al., "Sequence of a Full–Length cDNA for Rat Lung β–Galactoside–Binding Protein: Primary and Secondary Structure of the Lectin", Biochemistry, 1988, pp. 692–699, vol. 27, American Chemical Society.

Bladier et al., "β–Galactoside Soluble Lectin From Human Brain: Complete Amino Acid Sequence", Neurochemistry International, 1991, pp. 275–281, vol. 18, No. 2, Pergamon Press.

Horie et al., "Identification of Oxidized Galectin–1 as an Initial Repair Regulatory Factor after Axotomy in Peripheral Nerves", Neuroscience Research, 2000, pp. 131–137, vol. 38, Elsevier Science Ireland Ltd and the Japan Neuroscience Society.

\* cited by examiner

*Primary Examiner*—Elizabeth Kemmerer
*Assistant Examiner*—Sandra Wegert
(74) *Attorney, Agent, or Firm*—Foley & Lardner LLP

(57) ABSTRACT

This invention relates to a remedy for neuropathy, such as nerve injury, nerve degeneration, and hypofunction upon nerve grafting, which contains as the active ingredient galectin-1 having an amino acid sequence represented by SEQ ID NO:1 or its derivative; a protein having the amino acid sequence represented by SEQ ID NO:1 or one having a homology of 90% or more at the amino acid level with the sequence of SEQ ID NO:1 and carrying a disulfide bond(s) at least between Cys at the 16-position (Cys 16) and Cys at the 88-position (Cys 88) among cystein residues at the 2-position (Cys 2), 16-position (Cys 16), 42-position (Cys 42), 60-position (Cys 60), 88-position (Cys 88) and 130-position (Cys 130); and a process for producing the galectin-1 or its derivative protein by using an affinity column having an antibody to the above protein.

41 Claims, 10 Drawing Sheets

34% Acetonitrile Eluted Fraction

36% Acetonitrile Eluted Fraction

1 ; PBS
2 ; Concanavalin A
3 ; Reduced concanavalin A
4 ; E. coli expressed Gal1 (1-134)
5 ; Reduced E. coli expressed Gal1 (1-134)

SEQUENCE LISTING

<160> NUMBER OF SEQ ID NOS: 64

<210> SEQ ID NO 1
<211> LENGTH: 134
<212> TYPE: PRT
<213> ORGANISM: Homo sapiens

<400> SEQUENCE: 1

```
Ala Cys Gly Leu Val Ala Ser Asn Leu Asn Leu Lys Pro Gly Glu Cys
 1               5                   10                  15

Leu Arg Val Arg Gly Glu Val Ala Pro Asp Ala Lys Ser Phe Val Leu
            20                  25                  30

Asn Leu Gly Lys Asp Ser Asn Asn Leu Cys Leu His Phe Asn Pro Arg
        35                  40                  45

Phe Asn Ala His Gly Asp Ala Asn Thr Ile Val Cys Asn Ser Lys Asp
    50                  55                  60

Gly Gly Ala Trp Gly Thr Glu Gln Arg Glu Ala Val Phe Pro Phe Gln
65                  70                  75                  80
```

```
Pro Gly Ser Val Ala Glu Val Cys Ile Thr Phe Asp Gln Ala Asn Leu
            85                  90                  95
Thr Val Lys Leu Pro Asp Gly Tyr Glu Phe Lys Phe Pro Asn Arg Leu
            100                 105                 110
Asn Leu Glu Ala Ile Asn Tyr Met Ala Ala Asp Gly Asp Phe Lys Ile
            115                 120                 125
Lys Cys Val Ala Phe Asp
            130

<210> SEQ ID NO 2
<211> LENGTH: 587
<212> TYPE: DNA
<213> ORGANISM: Rattus norvegicus

<400> SEQUENCE: 2
ggcccctggt gcttcccccc ctcctcctga ggagggggcc tgtgaagagc atatgagcca    60
aacctgacca ctagcctcct ggagccagag aatgggggc atgtgaaagc cttctcaacc   120
cagtgcccag ccatcttccc tgagccgccg gcgggcggtg agcaatgcct gcctcacctt   180
catctggggg tgtccaggag gggtccagac tgtgaatcct gtgctctggc cgggaccact   240
cccccagtcc ccatccatcc cattgcatag gtttagagag agcacgtgtg accactggca   300
ttcatttggg gggtgggaga tattggcgga agccacccca gccttagtcc ccagggcaaa   360
gcgctgggga ggaagatggg gagtcaggga gggggaagt ctcagaagag ggaggagtct    420
gggagcgggg agggacggcc cagcctgtaa aatactgtac atgcactgct gtagatatac   480
tggaatgaat ttctgtaca tgtttggtta atttttttg tacatgattt ttgtatgttt     540
ccttttcaat aaaatcagat tgaacagtga aaaaaaaaa aaaaaaa                   587

<210> SEQ ID NO 3
<211> LENGTH: 332
<212> TYPE: DNA
<213> ORGANISM: Rattus norvegicus

<400> SEQUENCE: 3
acaccctggc cagcgcgggg gacttttttct gcaccatgta gcatactgga ctgccagcct    60
tgcttgtccc aggggcaggc aagggaagcc actcgagccc cggcagcctg ggtgcactga   120 tgagatacg gacttggggg accctggcct cccaaaagcc agggaaggga gggctgaagg    180
actcatggtg accagggggg tgggaccga ccgcccgcc tctgccgccc accaccatct    240
caggaaaggc tgctggtgct ggctgcccgt tccagctgca gggggggctc tgggggtgtc   300
cccagtgcgc cttcactttg ggcctggcct ca                                  332

<210> SEQ ID NO 4
<211> LENGTH: 335
<212> TYPE: DNA
<213> ORGANISM: Rattus norvegicus

<400> SEQUENCE: 4
ctagagtcgc ccgtgcccag cgccccggag gccctggcgg gaggccccac ccaagctgcc    60
ccgggagtgc gtgtggagga ggaggagtgg gcccgggaga tcggggccca gctgcggagg   120
atggcggacg acctcaacgc gcagtacgag cggcggagac aagaagagca acatcgacac   180
cgaccctcgc cctggagggt catgtataat ctcttcatgg gactcctccc cttacccagg   240
gatcctggag cccagaaaat ggagcccaac taggtgccta cacccgtccc ggggacgtc    300 ggagacttga ggggcaggac cccctccgcc ttctg                               335
```

<210> SEQ ID NO 5
<211> LENGTH: 317
<212> TYPE: DNA
<213> ORGANISM: Rattus norvegicus

<400> SEQUENCE: 5

```
aggctagatt tgaccctgta ttagaatagg ggtacttagg tcggataaat tgagggactt      60
ccacgttgat atgagcttta gtgggtaact ggccattcag gtgacccag agccacttcc     120
tcaagacccc tttctagggc ctgcggggaa gagtgggaaa aagaaatttc tatggctgtg    180
aggagaagcg gaggaaaaag cacagtatag ctacttagtg gctccgcgac gcttccggac    240
agactgggtg gatggtgacc acgccccttt cccctctccc aggtcctcag ccctcgctgt    300
caccagccca gcagcac                                                   317
```

<210> SEQ ID NO 6
<211> LENGTH: 1571
<212> TYPE: DNA
<213> ORGANISM: Rattus norvegicus

<400> SEQUENCE: 6

```
aggctagatt tgaccctgta ttagaatagg ggtacttagg tcggataaat tgagggactt      60
ccacgttgat atgagcttta gtgggtaact ggccattcag gtgacccag agccacttcc     120
tcaagacccc tttctagggc ctgcggggaa gagtgggaaa aagaaatttc tatggctgtg    180
aggagaagcg gaggaaaaag cacagtatag ctacttagtg gctccgcgac gcttccggac    240
agactgggtg gatggtgacc acgccccttt cccctctccc aggtcctcag ccctcgctgt    300
caccagccca gcagcaccta gagtcgcccg tgcccagcgc cccggaggcc ctggcgggag    360
gccccaccca agctgccccg ggagtgcgtg tggaggagga ggagtgggcc cgggagatcg    420
gggcccagct gcggaggatg gcggacgacc tcaacgcgca gtacgagcgg cggagacaag    480
aagagcaaca tcgacaccga ccctcgccct ggagggtcat gtataatctc ttcatgggac    540
tcctcccctt acccagggat cctggagccc cagaaatgga gcccaactag gtgcctacac    600
ccgtcccggg ggacgtcgga gacttgaggg gcaggacccc ctccgccttc tgacaccctg    660
gccagcgcgg gggacttttt ctgcaccatg tagcatactg gactgccagc cttgcttgtc    720
ccagggggcag gcaagggaag ccactcgagc cccggcagcc tgggtgcact gatggagata    780
cggacttggg ggaccctggc ctcccaaaag ccagggaagg gagggctgaa ggactcatgg    840
tgaccgaggg ggtggggacc gagccgcccg cctctgccgc ccaccaccat ctcaggaaag    900
gctgctggtg ctggctgccc gttccagctg cagggggggc tctggggtg tccccagtgc    960
gccttcactt tgggcctggc tcaggcccc tggtgcttcc cccctcctc ctgaggaggg     1020
ggcctgtgaa gagcatatga gccaaacctg accactagcc tcctggagcc agagaatggg   1080
gggcatgtga agccttctc aacccagtgc ccagccatct tccctgagcc gccggcgggc    1140
ggtgagcaat gcctgcctca ccttcatctg ggggtgtcca ggaggggtcc agactgtgaa   1200
tcctgtgctc tggccgggac cactccccca gtccccatcc atccattgc ataggtttag    1260
agagagcacg tgtgaccact ggcattcatt tggggggtgg gagatattgg cggaagccac   1320
cccagcctta gtccccaggg caaagcgctg ggaggaagaa tggggagtca gggagggggg   1380
aagtctcaga agagggagga gtctgggagc gggagggac ggcccagcct gtaaaatact    1440
gtacatgcac tgctgtagat atactggaat gaatttctg tacatgtttg gttaattttt    1500
```

```
tttgtacatg attttttgtat gtttcctttt caataaaatc agattgaaca gtgaaaaaaa   1560
aaaaaaaaaa a                                                         1571

<210> SEQ ID NO 7
<211> LENGTH: 419
<212> TYPE: DNA
<213> ORGANISM: Homo sapiens

<400> SEQUENCE: 7
ccatggcttg tggtctggtc gccagcaacc tgaatctcaa acctggagag tgccttcgag     60
tgcgaggcga ggtggctcct gacgctaaga gcttcgtgct gaacctgggc aaagacagca   120
acaacctgtg cctgcacttc aaccctcgct tcaacgccca cggcgacgcc aacaccatcg   180
tgtgcaacag caaggacggc ggggcctggg ggaccgagca gcgggaggct gtctttccct   240
tccagcctgg aagtgttgca gaggtgtgca tccttcga ccaggccaac ctgaccgtca   300
agctgccaga tggatacgaa ttcaagttcc caaccgcct caacctggag ccatcaact   360 acatggcagc tgacggtgac ttcaagatca atgtgtggc ctttgactga taaggatcc   419

<210> SEQ ID NO 8
<211> LENGTH: 427
<212> TYPE: DNA
<213> ORGANISM: Homo sapiens

<400> SEQUENCE: 8
ggatccccat ggcttgtggt ctggtcgcca gcaacctgaa tctcaaacct ggagagtgcc     60
ttcgagtgcg aggcgaggtg ctcctgacg ctaagagctt cgtgctgaac ctgggcaaag   120
acagcaacaa cctgtgcctg cacttcaacc ctcgcttcaa cgcccacggc gacgccaaca   180
ccatcgtgtg caacagcaag gacggcgggg cctgggggac cgagcagcgg gaggctgtct   240
ttcccttcca gcctggaagt gttgcagagg tgtgcatcac cttcgaccag gccaacctga   300
ccgtcaagct gccagatgga tacgaattca gttccccaa ccgcctcaac ctggaggcca   360
tcaactacat ggcagctgac ggtgacttca agatcaaatg tgtggccttt gactgataag   420
cggccgc                                                              427

<210> SEQ ID NO 9
<211> LENGTH: 142
<212> TYPE: PRT
<213> ORGANISM: Homo sapiens

<400> SEQUENCE: 9

Ile Glu Gly Arg Gly Ile Pro Met Ala Cys Gly Leu Val Ala Ser Asn
 1               5                  10                  15

Leu Asn Leu Lys Pro Gly Glu Cys Leu Arg Val Arg Gly Glu Val Ala
            20                  25                  30

Pro Asp Ala Lys Ser Phe Val Leu Asn Leu Gly Lys Asp Ser Asn Asn
        35                  40                  45

Leu Cys Leu His Phe Asn Pro Arg Phe Asn Ala His Gly Asp Ala Asn
    50                  55                  60

Thr Ile Val Cys Asn Ser Lys Asp Gly Gly Ala Trp Gly Thr Glu Gln
65                  70                  75                  80

Arg Glu Ala Val Phe Pro Phe Gln Pro Gly Ser Val Ala Glu Val Cys
                85                  90                  95

Ile Thr Phe Asp Gln Ala Asn Leu Thr Val Lys Leu Pro Asp Gly Tyr
            100                 105                 110
```

```
Glu Phe Lys Phe Pro Asn Arg Leu Asn Leu Glu Ala Ile Asn Tyr Met
        115                 120                 125

Ala Ala Asp Gly Asp Phe Lys Ile Lys Cys Val Ala Phe Asp
    130                 135                 140

<210> SEQ ID NO 10
<211> LENGTH: 104
<212> TYPE: DNA
<213> ORGANISM: Artificial Sequence
<220> FEATURE:
<223> OTHER INFORMATION: Description of Artificial Sequence: EcoRI-NotI
      of pGEXGal1 (all/Ser-3')

<400> SEQUENCE: 10
gaattcaagt tccccaaccg cctcaacctg gaggccatca actacatggc agctgacggt      60
gacttcaaga tcaaaagcgt ggcctttgac tgataagcgg ccgc                      104

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: Primer
      comprising NotI sequence for synthesis of cDNA

<400> SEQUENCE: 11
aactggaaga attcgcggcc gcaggaattt tttttttttt ttttt                      45

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Adaptor for
      addition of EcoRI sequence

<400> SEQUENCE: 12
aattcggcac gagg                                                        14

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:
      Complementary sequence to the nucleotides 52-71 of SEQ ID NO: 2

<400> SEQUENCE: 13
gtggtcaggt ttggctcata                                                  20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:
      Complementary sequence to the nucleotides 33-51 of SEQ ID NO: 2

<400> SEQUENCE: 14
tgctcttcac aggccccct                                                   19

<210> SEQ ID NO 15
<211> LENGTH: 21
<212> TYPE: DNA
<213> ORGANISM: Artificial Sequence
<220> FEATURE:
```

<223> OTHER INFORMATION: Description of Artificial Sequence: Primer for
      sequencing pEF18S

<400> SEQUENCE: 15
ggatcttggt tcattctcaa g                                              21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:
      Complementary sequence to the nucleotides 118-137 of SEQ ID NO: 3

<400> SEQUENCE: 16
ccaagtccgt atctccatca                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      Complementary sequence to the nucleotides 36-55 of SEQ ID NO: 3

<400> SEQUENCE: 17
ggcagtccag tatgctacat                                                20

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: M13 reverse
      primer

<400> SEQUENCE: 18
caggaaacag ctatgac                                                   17

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: M13(-20)
      forward primer

<400> SEQUENCE: 19
gtaaaacgac ggccagtg                                                  18

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      Complementary sequence to the nucleotides 64-83 of SEQ ID NO: 4

<400> SEQUENCE: 20
tcctcctcga cacgcactcc                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: T7 primer

```
<400> SEQUENCE: 21
taatacgact cactataggg                                                   20

<210> SEQ ID NO 22
<211> LENGTH: 12
<212> TYPE: PRT
<213> ORGANISM: Rattus norvegicus

<400> SEQUENCE: 22

Pro Gly Glu Cys Leu Arg Val Arg Gly Glu Val Ala
 1               5                  10

<210> SEQ ID NO 23
<211> LENGTH: 6
<212> TYPE: PRT
<213> ORGANISM: Rattus norvegicus

<400> SEQUENCE: 23

Leu Pro Asp Gly Tyr Glu
 1               5

<210> SEQ ID NO 24
<211> LENGTH: 10
<212> TYPE: PRT
<213> ORGANISM: Rattus norvegicus

<400> SEQUENCE: 24

Asp Ser Asn Asn Leu Cys Leu His Phe Asn
 1               5                  10

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: The
      nucleotide sequence 15-34 of GENBANK ACCESSION NO. J04456

<400> SEQUENCE: 25
tgcgcctgcc cgggaacatc                                                   20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: The
      nucleotide sequence 28-47 of GENBANK ACCESSION NO. J04456

<400> SEQUENCE: 26
gaacatcctc ctggactcaa                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:
      Complementary sequence to the nucleotides 472-491 of GENBANK
      ACCESSION NO. J04456

<400> SEQUENCE: 27
gctgccttta ttgggggcca                                                   20
```

```
<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence:
      Complementary sequence to the nucleotides 463-482 of GENBANK
      ACCESSSION NO. J04456, with a NotI site at the 5' site of the
      sequence

<400> SEQUENCE: 28
gagagagcgg ccgcattggg ggccatgggc tggc                                   34

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer for
      obtaining the clone pEFGl1 containing human galectin-1 cDNA

<400> SEQUENCE: 29
cctcagacag tggttcaaag                                                   20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer for
      obtaining the clone pEFGl1 containing human galectin-1 cDNA

<400> SEQUENCE: 30
tgcattcatt ttatgtttca g                                                 21

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence:
      Complementary sequence to the nucleotides 436-457 of GENBANK
      ACCESSSION NO. J04456, with a BamHI site at the 5' site of the
      sequence

<400> SEQUENCE: 31
agagtggatc cttatcagtc aaaggccaca catttg                                 36

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: The
      nucleotides 50-69 of GENBANK ACCESSION NO. J04456, with an NcoI
      site at the 5' site thereof

<400> SEQUENCE: 32
gagagaccat ggcttgtggt ctggtcgc                                          28

<210> SEQ ID NO 33
<211> LENGTH: 20
<212> TYPE: PRT
<213> ORGANISM: Homo sapiens
<220> FEATURE:
<221> NAME/KEY: MOD_RES
<222> LOCATION: (2)
<223> OTHER INFORMATION: An undetermined amino acid
<221> NAME/KEY: MOD_RES
```

```
<222> LOCATION: (16)
<223> OTHER INFORMATION: An undetermined amino acid

<400> SEQUENCE: 33

Ala Xaa Gly Leu Val Ala Ser Asn Leu Asn Leu Lys Pro Gly Glu Xaa
 1               5                  10                  15

Leu Arg Val Arg
            20

<210> SEQ ID NO 34
<211> LENGTH: 8
<212> TYPE: PRT
<213> ORGANISM: Homo sapiens

<400> SEQUENCE: 34

Gly Glu Val Ala Pro Asp Ala Lys
 1               5

<210> SEQ ID NO 35
<211> LENGTH: 4
<212> TYPE: PRT
<213> ORGANISM: Homo sapiens

<400> SEQUENCE: 35

Phe Pro Asn Arg
 1

<210> SEQ ID NO 36
<211> LENGTH: 10
<212> TYPE: PRT
<213> ORGANISM: Homo sapiens

<400> SEQUENCE: 36

Val Arg Gly Glu Val Ala Pro Asp Ala Lys
 1               5                  10

<210> SEQ ID NO 37
<211> LENGTH: 10
<212> TYPE: PRT
<213> ORGANISM: Homo sapiens

<400> SEQUENCE: 37

Asp Gly Gly Ala Trp Gly Thr Glu Gln Arg
 1               5                  10

<210> SEQ ID NO 38
<211> LENGTH: 8
<212> TYPE: PRT
<213> ORGANISM: Homo sapiens

<400> SEQUENCE: 38

Leu Pro Asp Gly Tyr Glu Phe Lys
 1               5

<210> SEQ ID NO 39
<211> LENGTH: 12
<212> TYPE: PRT
<213> ORGANISM: Homo sapiens

<400> SEQUENCE: 39

Asp Ser Asn Asn Leu Cys Leu His Phe Asn Pro Arg
 1               5                  10

<210> SEQ ID NO 40
```

```
<211> LENGTH: 15
<212> TYPE: PRT
<213> ORGANISM: Homo sapiens

<400> SEQUENCE: 40

Phe Asn Ala His Gly Asp Ala Asn Thr Ile Val Cys Asn Ser Lys
 1               5                  10                  15

<210> SEQ ID NO 41
<211> LENGTH: 8
<212> TYPE: PRT
<213> ORGANISM: Homo sapiens

<400> SEQUENCE: 41

Ser Phe Val Leu Asn Leu Gly Lys
 1               5

<210> SEQ ID NO 42
<211> LENGTH: 16
<212> TYPE: PRT
<213> ORGANISM: Homo sapiens

<400> SEQUENCE: 42

Leu Asn Leu Glu Ala Ile Asn Tyr Met Ala Ala Asp Gly Asp Phe Lys
 1               5                  10                  15

<210> SEQ ID NO 43
<211> LENGTH: 18
<212> TYPE: PRT
<213> ORGANISM: Homo sapiens

<400> SEQUENCE: 43

Ala Cys Gly Leu Val Ala Ser Asn Leu Asn Leu Lys Pro Gly Glu Cys
 1               5                  10                  15

Leu Arg

<210> SEQ ID NO 44
<211> LENGTH: 26
<212> TYPE: PRT
<213> ORGANISM: Homo sapiens

<400> SEQUENCE: 44

Glu Ala Val Phe Pro Phe Gln Pro Gly Ser Val Ala Glu Val Cys Ile
 1               5                  10                  15

Thr Phe Asp Gln Ala Asn Leu Thr Val Lys
                20                  25

<210> SEQ ID NO 45
<211> LENGTH: 5
<212> TYPE: PRT
<213> ORGANISM: Homo sapiens

<400> SEQUENCE: 45

Cys Val Ala Phe Asp
 1               5

<210> SEQ ID NO 46
<211> LENGTH: 12
<212> TYPE: PRT
<213> ORGANISM: Homo sapiens

<400> SEQUENCE: 46

Ala Cys Gly Leu Val Ala Ser Asn Leu Asn Leu Lys
 1               5                  10
```

<210> SEQ ID NO 47
<211> LENGTH: 5
<212> TYPE: PRT
<213> ORGANISM: Homo sapiens

<400> SEQUENCE: 47

Cys Val Ala Phe Asp
 1               5

<210> SEQ ID NO 48
<211> LENGTH: 6
<212> TYPE: PRT
<213> ORGANISM: Homo sapiens

<400> SEQUENCE: 48

Pro Gly Glu Cys Leu Arg
 1               5

<210> SEQ ID NO 49
<211> LENGTH: 26
<212> TYPE: PRT
<213> ORGANISM: Homo sapiens

<400> SEQUENCE: 49

Glu Ala Val Phe Pro Phe Gln Pro Gly Ser Val Ala Glu Val Cys Ile
 1               5                  10                  15

Thr Phe Asp Gln Ala Asn Leu Thr Val Lys
             20                  25

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: The
      nucleotides 50-69 of GENBANK ACCESSSION NO.
      J04456, with a BamHI site at the 5' site thereof

<400> SEQUENCE: 50
gagagaggat ccccatggct tgtggtctgg tcgc                              34

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence:
      Complementary sequence to the nucleotides 436-457 of GENBANK
      ACCESSION NO. J04456, with a NotI site at the 5' site of the
      sequence

<400> SEQUENCE: 51
agagtgcggc cgcttatcag tcaaaggcca cacatttg                          38

<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: The
      nucleotides 50-68 of GENBANK ACCESSION NO. J04456, with a BamHI
      site at the 5' site thereof

<400> SEQUENCE: 52
gagagaggat ccccatggct agcggtctgg tcg                               33

-continued

<210> SEQ ID NO 53
<211> LENGTH: 37
<212> TYPE: DNA
<213> ORGANISM: Artificial Sequence
<220> FEATURE:
<223> OTHER INFORMATION: Description of Artificial Sequence:
    Complementary sequence to the nucleotides 437-457 of GENBANK
    ACCESSION NO. J04456, with a NotI site at the 5' site thereof

<400> SEQUENCE: 53
agagagcggc cgcttatcag tcaaaggcca cacattt                              37

<210> SEQ ID NO 54
<211> LENGTH: 97
<212> TYPE: DNA
<213> ORGANISM: Artificial Sequence
<220> FEATURE:
<223> OTHER INFORMATION: Description of Artificial Sequence: The
    nucleotides 366-457 of GENBANK ACCESSION NO. J04456, with a NotI
    site at the 5' site thereof

<400> SEQUENCE: 54
aattcaagtt ccccaaccgc tcaacctgg aggccatcaa ctacatggca gctgacggtg      60
acttcaagat caaaagcgtg gcctttgact gataagc                              97

<210> SEQ ID NO 55
<211> LENGTH: 97
<212> TYPE: DNA
<213> ORGANISM: Artificial Sequence
<220> FEATURE:
<223> OTHER INFORMATION: Description of Artificial Sequence:
    Complementary sequence to the nucleotides 370-457 of GENBANK
    ACCESSION NO. J04456, with a NotI site at the 5' site thereof

<400> SEQUENCE: 55
ggccgcttat cagtcaaagg ccacgctttt gatcttgaag tcaccgtcag ctgccatgta    60
gttgatggcc tccaggttga ggcggttggg gaacttg                              97

<210> SEQ ID NO 56
<211> LENGTH: 56
<212> TYPE: DNA
<213> ORGANISM: Artificial Sequence
<220> FEATURE:
<223> OTHER INFORMATION: Description of Artificial Sequence: The
    nucleotides 50-105 of GENBANK ACCESSION NO. J04456 with changes to
    A, C and A at the positions 56, 58 and 98 respectively

<400> SEQUENCE: 56
atggctagcg gtctggtcgc cagcaacctg aatctcaaac ctggagagag ccttcg         56

<210> SEQ ID NO 57
<211> LENGTH: 65
<212> TYPE: DNA
<213> ORGANISM: Artificial Sequence
<220> FEATURE:
<223> OTHER INFORMATION: Description of Artificial Sequence: The
    nucleotides 171-235 of GENBANK ACCESSION NO. J04456 with changes
    to A and A at the positions 176 and 230 respectively

<400> SEQUENCE: 57
acctgagcct gcacttcaac cctcgcttca acgcccacgg cgacgccaac accatcgtga    60
gcaac                                                                 65

<210> SEQ ID NO 58

```
<211> LENGTH: 65
<212> TYPE: DNA
<213> ORGANISM: Artificial Sequence
<220> FEATURE:
<223> OTHER INFORMATION: Description of Artificial Sequence:
      Complementary sequence to the nucleotides 171-235 of GENBANK
      ACCESSION NO. J04456

<400> SEQUENCE: 58
gttgctcacg atggtgttgg cgtcgccgtg ggcgttgaag cgagggttga agtgcaggct    60
caggt                                                               65

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence:
      Complementary sequence to the nucleotides 354-375 of GENBANK
      ACCESSION NO. J04456

<400> SEQUENCE: 59
aacttgaatt cgtatccatc tg                                            22

<210> SEQ ID NO 60
<211> LENGTH: 65
<212> TYPE: DNA
<213> ORGANISM: Artificial Sequence
<220> FEATURE:
<223> OTHER INFORMATION: Description of Artificial Sequence:
      Complementary sequence to the nucleotides 311-375 of GENBANK
      ACCESSSION NO. J04456 with substitution of T for A at the
      position 314

<400> SEQUENCE: 60
aacttgaatt cgtatccatc tggcagcttg acggtcaggt tggcctggtc gaaggtgatg    60
ctcac                                                               65

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Amino acid
      sequence added to the N-terminus of Gal1(1-134)

<400> SEQUENCE: 61

Gly Ile Pro Met
  1

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: N-terminal
      sequence of GIPM-Gal1 (1-134)
<221> NAME/KEY: MOD_RES
<222> LOCATION: (6)
<223> OTHER INFORMATION: Unidentified amino acid

<400> SEQUENCE: 62

Gly Ile Pro Met Ala Xaa Gly Leu Val Ala Ser Asn Leu Asn Leu
  1               5                  10                  15

<210> SEQ ID NO 63
<211> LENGTH: 10
```

-continued

```
<212> TYPE: DNA
<213> ORGANISM: Artificial Sequence
<220> FEATURE:
<223> OTHER INFORMATION: Description of Artificial Sequence: Synthetic
      adaptor

<400> SEQUENCE: 63
cctcgtgccg                                                              10

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 64
gagagaggat ccccatggct agcggtctgg tcg                                    33
```

NEURONAL GROWTH FACTOR GALECTIN-1

TECHNICAL FIELD OF THE INVENTION

The present invention relates to Galectin-1, or derivatives thereof, having nerve regeneration promoting activity such as the regeneration of axons, the repair of nerve tissues and the like, and remedies for neuropathy involving nerve injury, nerve degeneration and hypofunction at nerve grafting which contain such proteins as the active ingredients.

BACKGROUND OF THE INVENTION

Most neuropathies, e.g. nerve injury caused by a traffic accident, nerve injury or nerve degeneration caused by remedies for cancers or AIDS, and the injury or hypofunction of peripheral nerves or central nerves caused by amyotrophic lateral sclerosis, diabetic neuropathy, dementia senilis, Alzheimer's disease, Parkinson's disease and the like are intractable, they present a serious condition, and often lead to death of a patient. However, at present, there is no effective remedy. Since, degeneration and deciduation of nerve tissues, transaction and regression of axons, and so on occur in these neuropathies, in order to prevent and treat the neuropathy, a factor which acts to inhibit nerve tissue degeneration or apoptosis and promoting axons regeneration, is required as an effective remedy.

Since Levi-Montalcini et al. found nerve growth factor (NGF) about 40 years ago, it has been revealed that humoral factors acting on nerve cells, i.e., a neurotrophic factor group including ciliary neurotrophic factor (CNTF), brain-derived neurotrophic factor (BDNF), neurotrophin-3 (NT-3), neurotrophin-4/5 (NT-4/5) and glia-derived neurotrophic factor (GDNF), and cytokines or the like contain a factor acting to support the survival of various neurons and to regenerate axons. And the applicability of some kinds of these factors to pharmaceutical formulations has also been studied.

Galectin is a generic name for an animal lectin specific for a lactosamine sugar chain, and is also called β galactoside-binding animal lectin or S-type lectin. Galectin is confirmed to exist in the cells of animal tissues ranging from lower Invertebrata such as nematode and sponge to bird and human. Some species of this type of lectin had been found, and in 1994, these were proposed to be generically called "galectin" (S. H. Barondes et al, *Cell,* 76, 597–598, 1994). Up until now, galectin-1 to galectin-11 have been reported as members of the galectin family. It has been reported that the actions of these galectins are associated with cell growth and cell adhesion, but these physiological functions are still unknown (J. Hirabayashi et al., *J. Biochem.,* 119, 1–8, 1996; N. L. Perillo et al., *J Mol Med.,* 76, 402–412, 1998). With regard to galectin-1, the structures of a large number of animal-derived forms have been determined (human-galectin-1: J. Hirabayashi et al., *J. Biochem.,* 104, 1–4, 1988; J. Hirabayashi et al., *Biochim. Biophys, Acta.,* 1008, 85–91, 1989, rat galectin-1: L. B. Clerch et al., *Biochemistry,* 27, 692–699, 1988, mouse galectin-1: T. J. G. Wilson et al., *Biochem. J.,* 261, 847–852, 1989, bovine galectin-1: W. M. Abbot et al., *Biochem. J.,* 259, 283–290, 1989). Information regarding the galectin-1 gene and protein, and a remedy for autoimmune diseases are disclosed in Japanese Patent Application Laying-Open (kokai) No. 2-84192 (Title: Mammalian 14-β-gal Lectins, Applicant: Ideon Corporation) and International Publication WO94/11497 (Title: Method of causing selective immunosuppression using HL-60-related lectins, Applicant: Incyte Pharmaceuticals Inc.) However, there is no description regarding galectin-1 as a remedy for neurodegenerative diseases such as nerve injury and neuropathy in the above documents.

On the other hand, as stated below, there are some reports on the relation between galectin-1 and the nervous system: galectin-1 expresses in a dorsal spinal nerve root ganglion cell at the development stage of a sensory nerve (J. Dodd, et al. *J Exp Biol.* 124, 225–238, 1986; M. A. Hynes, et al. *J. Neurosci.,* 10, 1004–1013, 1990); galectin-1 is associated with the aggregation of nerve cells or the development of neurites, as a cell adhesive substrate, in a dorsal spinal root ganglion cell (R. L. Outenreath et al., *J. Neurocytol.,* 21, 788–795, 1992); galectin-1 expresses in a rat olfactory nerve cell at the development stage, and is associated with the development of axons as a cell adhesive substrate (N. K. Mahanthappa, et al. *Development.* 120, 1373–1384, 1994; E. H. Raabe, et al. *Brain Res Dev Brain Res.* 101, 187–196, 1997); galectin-1 is associated with the development of axons in a culture system comprising mouse olfactory nerve cells, as a cell adhesive substrate (A. C. Puch, et al. *Dev. Biol.* 179, 274–287, 1996); there are reports on the distribution of galectin-1 in some kinds of nerve tissues (R. Joubert et al, *Dev. Neurosci. II,* 397413, 1989; S. Kuchler et al, *Dev. Neurosci., II,* 414–427, 1989), etc. These reports on galectin-1 are limited to discussion of its distribution in nerve tissues or its function as an adhesive substrate of nerve cells, and contain no description of galectin-1 as a factor that promotes nerve regeneration by acting on a nerve cell or a paraneural system, such as do neurotrophic factors or cytokines which act on the nervous system. Furthermore, it has been found that human galectin-1 has 6 cysteine residues in a molecule thereof, and that this protein has β-galactoside binding activity in a state where this protein is reduced, i.e., the cysteine is free, whereas this protein does not have that activity in a state where this protein is oxidized, i.e., a SS bond is formed. All of the above-mentioned laying-open applications or reports regarding the nervous system describe regarding the existence and function of galectin-1 as a lectin. However, there is no report at all in respect of the physiological action of galectin-1 on nervous systems as a nerve regeneration promoting factor or a nerve survival-support factor in a state where this protein is oxidized, i.e., SS bonds are formed and there is no lectin activity.

Not only the above stated biological properties, but also physicochemical properties are also greatly different between oxidized galectin-1 and reduced galectin-1. Since the formation of a SS bond by oxidation means that one cystine residue is formed from two cysteine residues, accordingly the oxidized protein loses two hydrogen atoms per SS bond, i.e., 2 Dalton (Da) of molecular weight are decreased. Human galectin-1 may form 3 couples of SS bond, and in such a case, the protein loses 6 Da of molecular weight. The difference of molecular weight can be determined by measuring the molecular weight with a high precision mass spectrometer. Furthermore, since the higher order structure of protein is greatly changed by the formation of SS bond, and both the steric dimensions of molecule and amino acid residues existing on a molecular surface are changed, the mobility on SDS electrophoresis and the elution time in reversed phase chromatography, ion exchange chromatography and the like are also changed. By examining physicochemical properties, it is possible to distinguish whether galectin-1 is in an oxidized state or in a reduced state.

In neuropathy, the degeneration and deciduation of nerve tissues, the transection and regression of axons, and the like occur. So, as an effective remedy for preventing or treating this disease, a neurotrophic factor or the like which acts to control the degeneration of nerve tissues or apoptosis and promote the regeneration of neurites is desired. The study on the applicability of a neurotrophic factor group including NGF, CNTF, BDNF etc. to remedies has been proceeding. These neurotrophic factor groups are ones having a function of promoting neurite regeneration and supporting the survival, and these were mainly found in nerve cells isolated from fetal or young animals at the development stage. So, to allow expression of the actions of neurotrophic factors, it is necessary to allow the factors to directly act on nerve cells. However, the reactivity to factors may be different between nerve cells of adult animals and those of fetal or young animals. Furthermore, as distinct from its state in a culture plate, each nerve cell does not exist separately in vivo, but generally nerve cells attach with each other or are enclosed by paraneural system cells such as Schwann cell, so that they exchange information interactively to maintain their functions. Where nerves are regenerated after nerve injury occurred, nerve cells perform cross talk with other cells surrounding them to repair their functions. As is clear from the above descriptions, there is the problem of how the factor groups can be made to act on nerve cells on which they directly act, in other words, there is the problem of administration method, therefore the development of remedies for neuropathy faces difficulty.

Under these circumstances, using the organ culture system of nerve tissues which maintains its functional structure in vivo, the present inventors have continued a thorough study to find out a novel protein factor indicating activity which promotes neurite regeneration from a transected nerve end of nerve tissues and supports its survival, or a novel use of the known factors as remedies for treating neuropathy or nerve injury.

To sum up, the main purpose of the present invention is to provide galectin-1 which is effective for treating neuropathy involving nerve injury, nerve degeneration and hypofunction at nerve grafting and derivatives thereof, and remedies for neuropathy containing them as active ingredients.

SUMMARY OF THE INVENTION

The present inventors have carried out various studies to obtain a factor promoting neurite regeneration from a transected nerve end of nerve tissues and supporting (or maintaining) the survival thereof. As an evaluation method which is much similar to in vivo conditions, an organ culture assay system was applied, wherein the dorsal root ganglion tissues of an adult or aged rat were embedded into a collagen gel, and the axonal regeneration from the transected nerve end was observed, therewith the factor was screened. As a result, from the COS1 cell culture supernatant into which cDNA derived from rat liver was transfected with an animal expression vector, an active factor promoting the axonal regeneration from a transected nerve end of nerve tissues and supporting the survival thereof, was purified. Then, a part of the sequence was determined, and this factor was identified as a protein having galectin-1 sequence. Furthermore, it was also found that a protein expressed from DNA encoding the galectin-1 promotes the axonal regeneration both in vitro and in vivo and has survival supporting activity.

The inventors have conducted various studies to obtain a factor, which promotes regeneration of axons from the transected nerve fiber terminal of the nerve tissue and maintains its survival. The inventors have screened for such a factor by an organ culture assay system comparable to in vivo conditions. In this assay system, DRG (dorsal root ganglion) derived from a mature or aged rat was embedded in collagen gel, and regeneration of axons from the transected nerve end was observed. Thus, the inventors have purified an active factor, which promotes regeneration of axons from the transected nerve end of DRG and maintains survival of the nerve fiber, from the culture supernatant of COS 1 cells; determined its partial sequence; and identified it as a protein having galectin-1 sequence. In addition, the inventors have found that a protein expressed by DNA encoding this galectin-1 can promote regeneration of axons both in vitro and in vivo, that is, it has survival-maintaining activity of the nerve fiber.

The present invention provides remedies for neuropathy involving nerve injury, nerve degeneration, and hypofunction (or dysfunction) at nerve grafting, which contain as an active ingredient galectin-1 or its derivatives having an amino acid sequence shown in SEQ ID No:1.

Galectin-1 or its derivatives used in this invention may have lectin activity, or may have almost no lectin activity or no lectin activity. As used herein, the term "lectin activity" means β-galactoside binding activity. Lectin having such activity normally possesses an ability to bind to a lactose column or an ability to allow hemagglutination.

In an embodiment of this invention, galectin-1 or its derivatives carry a disulfide bond(s) at least between Cys at the 16-position (Cys 16) and Cys at the 88-position (Cys 88) among cysteine residues at the 2-position (Cys 2), 16-position (Cys 16), 42-position (Cys 42), 60-position (Cys-60), 88-position (Cys 88) and 130-position (Cys 130) in the amino acid sequence shown in SEQ ID NO:1.

As used herein, the term "oxidized" means that two or more cysteine residues of the protein are in an oxidized state, that is, the residues form a disulfide bond(s).

The protein of this invention possesses a nerve regeneration-promoting effect, including regeneration of axons and repair of nerve tissues. In this respect, the protein of this invention has a function similar to that of a neurotrophic factor. A known type of galectin-1 is a reduced type, has lectin activity, and has an effect as an adhesive substrate of nerve cells (N. K. Mahanthappa et al., supra; A. C. Puch et al., supra). However, it was not known that galectin-1 functions as a nerve regeneration-promoting factor.

Galectin-1 or its derivatives illustrated according to an embodiment of this invention, carry disulfide bonds between the following Cys residues in the amino acid sequence shown in SEQ ID NO:1:
(1) Cys 16–Cys 88, Cys 2–Cys 130 and Cys 42–Cys 60; or
(2) Cys 16–Cys 88, Cys 2–Cys 60 and Cys 42–Cys 130; or
(3) Cys 16–Cys 88, Cys 2–Cys 42 and Cys 60–Cys 130, or they may comprise a mixture of at least two groups out of (1), (2) and (3), especially the one contains 50% or more said (1).

Examples of the derivatives are as follows:
(a) Derivatives, which have an amino acid sequence comprising at least one amino acid substitution, deletion, insertion and/or addition relative to the amino acid sequence shown in SEQ ID NO:1, and have a nerve regeneration-promoting activity; or have an amino acid sequence substantially shown in SEQ ID NO:1. The term "substantially" means that such an amino acid sequence can contain a change (i.e., substitution, deletion, insertion and/or addition) in at least one amino acid residue that has no effect on nerve regeneration-promoting activity.

(b) Derivatives, which have a homology of 80% or more, preferably 90% or more, more preferably 95% or more at amino acid level with the amino acid sequence shown in SEQ ID NO:1.
(c) Derivatives, which have the acylated (for example, formylated and acetylated) N-terminal end.
(d) Derivatives, in which Met$^{-2}$ Lys$^{-1}$ or Met$^{-1}$ is added to the N-terminal end.
(e) Derivatives, which are covalently bound with a water-soluble polymer (for example, polyethylene glycol) or a carbohydrate chain(s).

Remedies of this invention are useful in treatment for neuropathy, for example, promotion of nerve regeneration and functional recovery from central and peripheral nerve damage due to external injuries resulted from an accident and surgery; disorders resulted from nerve damages due to curative treatment, such as chemotherapy or radiation therapy against diseases including cancer, AIDS, and the like; nerve damages resulted from central and peripheral nerve injuries due to drugs, heavy metals, chemicals such as alcohols; nerve injuries resulted from ischaemia or infection, malignancy or metabolic disorders, for example, diabetic neuropathy, or dysfunction in kidney or liver; degeneration of special nerve cells including amyotrophic lateral sclerosis, which is a motor nerve degenerative disorder, and nerve degenerative disorders, such as Alzheimer's disease. Moreover, the remedies of this invention can be used as a nerve regeneration-promoting agent for recovery of neuropathy such as hypofunction upon nerve grafting.

Remedies of this invention can be made into a pharmaceutical form, such as for oral and parenteral administration by combining with a pharmaceutically acceptable liquid or solid carrier. In addition, the remedy may contain one or more factors having neurotrophic activity, including NGF (nerve growth factor), and BDNF (brain-derived nerve growth factor); or extracellular matrix having such factors or paraneural cells.

In an embodiment of this invention, the remedies of this invention may be in the form that is prepared by allowing the protein of this invention to be contained into collagen gel, adding (an)other neurotrophic factor(s) if necessary, and directly embedding at a site of nerve injury. In this case, essential ingredients, such as pharmaceutical agent and carrier, are placed or packed within a tube made of a biocompatible material (for example, silicon rubber, collagen, polypropylene, polyester, or polyamide).

Moreover, the present invention relates to a method for the treatment of neuropathy, comprising administering the above remedy of this invention to a patient (including human) who needs the treatment of neuropathy such as nerve injury, nerve degeneration, or hypofunction upon nerve grafting.

The present invention also provides the above-defined galectin-1 or its derivatives.

Furthermore, the present invention provides a process of producing the above protein comprising the steps of loading a substance containing the above-defined galectin-1 or its derivative (for example, a natural substance or the one prepared by recombination or a chemical method) to an affinity column to which an antibody or antibodies to the above protein are bound, allowing the protein to be adsorbed, subsequently eluting the protein, and if necessary oxidizing the protein.

DETAILED DESCRIPTION OF THE INVENTION

Figure 1:
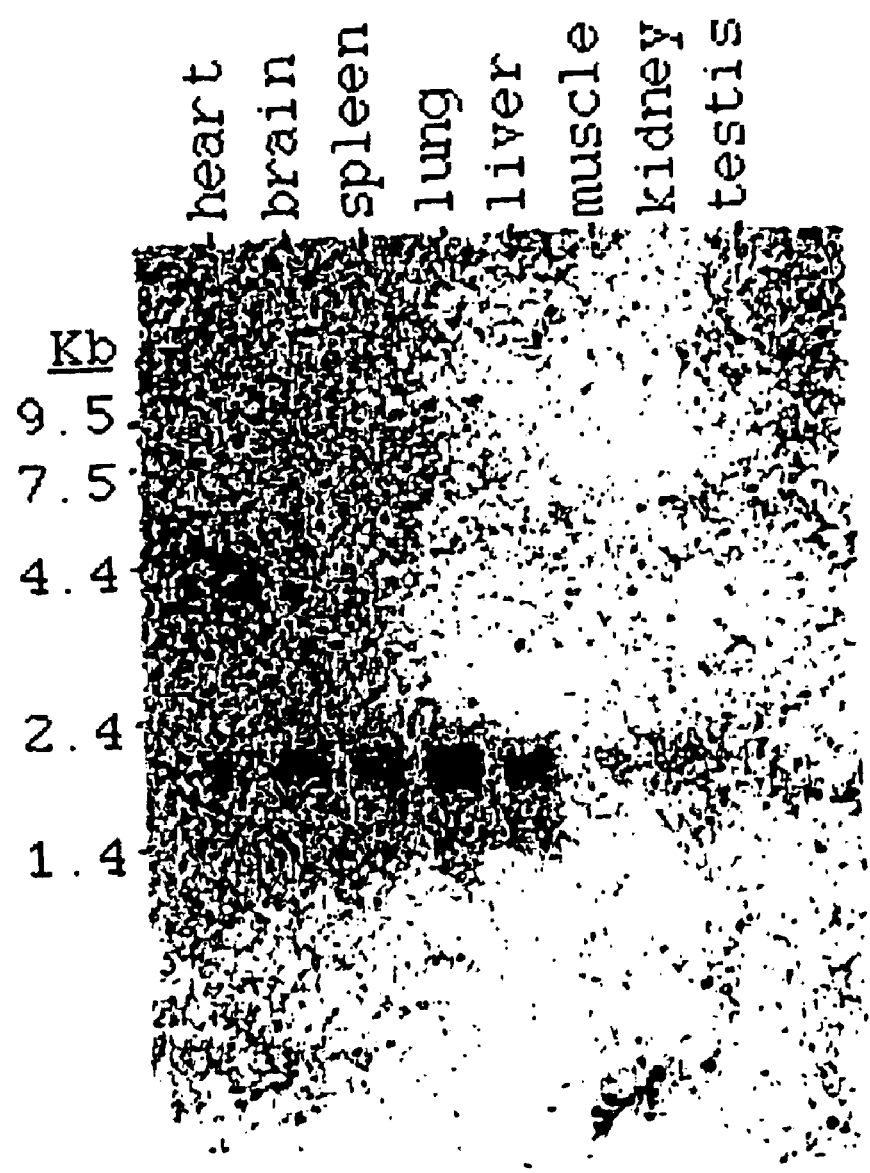
FIG. 1 is a photograph of an electrophoresis showing the results of Northern Blot assay regarding RNA obtained from each tissue of a rat.

Hereinafter, the present invention is further described with regard to the method of producing the protein of the present invention which has a nerve regeneration promoting activity (hereinafter "the protein of the present invention") and pharmaceutical compositions containing the protein.

Gene Construction

The protein of the present invention can be obtained by a process of: constructing a recombinant vector comprising DNA encoding a complete or partial amino acid sequence shown in SEQ ID NO:1, or DNA encoding the derivatives of the above amino acid sequence (e.g. an amino acid sequence wherein one or more amino acids are substituted, deleted, inserted and/or added); transforming a host cell with the above vector, culturing the obtained host cell; and finally separating and purifying the protein of interest.

The DNA encoding the protein of the present invention can be obtained by a process of: obtaining DNA by the restriction enzyme cleavage of genomic DNA, cloning from cDNA library, or DNA synthesis, and then converting and amplifying the obtained DNA by site-directed mutagenesis techniques such as oligonucleotide site-directed mutagenesis or cassette mutagenesis, or PCR method. In this case, for example, a technique described in *Molecular Cloning* (Sambrook et al., Cold Spring Harbor Laboratory Press (1989)) can be applied.

The gene of the protein of the present invention and its structure are already known in respect of various living things including human and mouse (e.g. Abbott et al., *Biochem. J.*, 259, 291–294, 1989; Chiariotti et al., *Biochim. Biophys. Acta*, 1089, 54–60, 1991). So, on the basis of the information regarding these known nucleotide sequences and amino acid sequences, DNA encoding the protein of the present invention can be obtained/produced from cDNA library, as appropriate, using PCR method, DNA synthesis technique and so on.

As shown in Examples described later, the cDNA encoding the protein of the present invention can be obtained by producing a cDNA library from human liver tissue in accordance with standard techniques and then applying PCR method, using primers produced on the basis of the known nucleotide sequence of human galectin-1.

In the case of applying DNA chemical synthesis, according to e.g. the method of Alton et al. (Japanese Patent Application Laying-Open (kohyo) No. 59-501097), a DNA fragment encoding the protein of the present invention can be obtained by designing the nucleotide sequence on the basis of the amino acid sequence of the protein of the present invention, and using preferential codons, if necessary.

Furthermore, regarding a polypeptide derived by deletion, addition, insertion and/or substitution of one or more amino acid residues in the amino acid sequence shown in SEQ ID NO: 1, on the basis of the above-stated DNA encoding galectin-1, DNA encoding the mutant polypeptide can be produced by site-directed mutagenesis techniques such as oligonucleotide site-directed mutagenesis or cassette mutagenesis (e.g. Mark et al., *Proc. Natl. Acad. Sci. USA*, 81, 5662–5666, 1984; Inouye et al., *Proc. Natl. Acad. Sci. USA*, 79, 3438–3441, 1982; PCT WO85/00817 laid-open on Feb. 28, 1985; and Wharton et al., *Nature*, 316, 601–605, 1985) or PCR method, or by DNA chemical synthesis.

Applicable host cells include prokaryotic cells (e.g. those of bacteria and preferably *Escherichia coli*) and eukaryotic cells (e.g. those of yeast, insect or mammal). Examples of mammalian cells include a COS cell, Chinese Hamster Ovary cell, X63.6.5.3. cell, C-127 cell, BHK (Baby Hamster Kidney) cell, human-derived cell (e.g. HeLa cell), etc. Examples of yeast include a baker's yeast (*Saccharomyces cerevisiae*), methanol-assimilated yeast (*Pichia pastoris*), etc. Examples of insect cells include a silk worm culture cell (e.g. Sf21 cell) and the like.

When the protein of the present invention is produced using a prokaryotic or eukaryotic cell, the protein can be obtained by a process of: adding cleavage sites by restriction enzymes and/or promoter DNA facilitating expression, to DNA encoding the protein; integrating the above DNA into an appropriate expression vector, culturing the cells transformed or transfected by the vector, and separating and purifying the generated protein of the present invention. In the case where *Escherichia coli* is selected as a host, a codon (priority codon) which is preferable to the expression in *Escherichia coli* may be integrated.

Vectors used for transforming *Escherichia coli* include pKC30 (Shimatake H. and M. Rosenberg, *Nature*, 292, p 128–132, 1981), pTrc99A (Amann E. et al, *Gene*, 108, 193–200, 1991), pCFMS36 (ATCC No. 39934; Japanese Patent Application Laying-Open (kohyo) No. 60-501988), etc.

Vectors for mammalian cells include pSV2-neo (Southern and Berg, *J. Mol. Appl. Genet.*, 1, 327–341, 1982), pCAGGS (Niwa et al., *Gene*, 108, 193–200, 1991) or pcDL-SR α 296 (Takebe et al., *Mol. Cell. Biol.*, 8, 466–472, 1988), etc. Those for yeast include pG-1 (Schena M. and Yamamoto K. R., *Science*, 241, 965–967, 1988), etc. Those for silk worm cells include a transfer vector pAc373 used for preparing recombinant viruses (Luckow et al., *Bio/Technology*, 6, 47–55, 1988), etc.

These vectors may comprise a replication origin, selective marker, promoter and ribosome binding-site, as needed, and these for eukaryotic cells may further comprise an RNA splice site, polyadenylation signal and so on, as needed.

Examples of replication origins comprised in vectors for mammalian cells include those derived from SV40, adenovirus, bovine papilloma virus, etc. Examples of replication origins comprised in vectors for *Escherichia coli* include those derived from ColE1, R factor, F factor, etc. Replication origins comprised in vectors for yeast include those derived from 2 μm DNA, ARS1, etc.

Promoters for gene expression comprised in vectors for mammalian cells include those derived from viruses, e.g. retrovirus, polyoma virus, adenovirus, SV40, etc., or those derived from chromosomes, e.g. EF1-α, etc. The promoters comprised in vectors for *Escherichia coli* include a promoter derived from bacteriophage λ or a trp, lpp, lac or tac promoter, etc. The promoters comprised in vectors for baker's yeast include an ADH, PH05, GPD, PGK or MAF α promoter, and those for methanol-assimilated yeast include AOX1 promoter and the like. The promoters for silk worm cell vectors include that derived from nuclear polyhedrosis virus and the like.

Selective markers for vectors for mammalian cells include a neomycin (neo) resistance gene, thymidine kinase (TK) gene, dihydrofolate reductase (DHFR) gene, *Escherichia coli* xanthine guanine phosphoribosyltransferase (Ecogpt) gene, etc. Those for vectors for *Escherichia coli* include a kanamycin resistance gene, ampicillin resistance gene, tetracycline resistance gene, etc. Those for vectors for yeast include a Leu2, Trp1 or Ura3 gene, etc.

For example, when the protein of the present invention consisting of amino acids 1 to 134 of the amino acid sequence shown in SEQ ID NO:1 is produced, first, DNA encoding amino acids 1 to 134 is synthesized, and then NcoI site (which comprises ATG of initiation codon) is added to N-terminal of the DNA, whereas stop codon is added to the C-terminal and BamHI site is added downstream of the C-terminal. This DNA fragment is treated with NcoI and BamHI, and linked to pET-3d (Stratagene) which was digested with NcoI and BamHI. Then, using *Epicurian Coli* BL21 (DE3) Competent Cells (Stratagene), a transformant used for expressing the protein of the present invention is obtained from *Escherichia coli* having an expression vector. In an expression plasmid pET-3d, the gene of interest is inserted downstream of T7 phage promoter and transcribed by T7 RNA polymerase provided from a host *Escherichia coli*. Since this T7 RNA polymerase gene is integrated into a host *Escherichia coli* chromosome which is downstream of lac UV5 promoter, its expression can be controlled by inducing with the addition of IPTG.

Protein Expression, Refolding and Purification

In order to obtain the protein of the present invention using the above-described host-vector systems, the following process may be applied: a host cell is transformed by a recombinant DNA wherein the gene is integrated into the proper site of the above vectors; the obtained transformant is cultured; and the polypeptide is separated and purified from cells or culture medium. This process can be carried out by the combined use of known means and methods.

In the case of expressing the protein using a host, the original signal sequence may be converted, or the signal sequences of other proteins may be used, in order to more reliably uniformizing the N-terminus of the expression product. Or, N-terminus can be uniformized even by converting (substituting or adding) amino acid residues positioned at, or in the vicinity of the N-terminus (e.g. adding arginine or lysine residues other than methionine residues, in the case of expressing the protein using *Escherichia coli*).

Furthermore, the protein of the present invention can also be obtained by a process of: adding Glutathione-S-transferase (GST), histidine tag, FLAG peptide or the like to the N- or C-terminus of the protein of the present invention through the recognition peptide of a specific enzyme (e.g. thrombin, Factor Xa, enterokinase, etc.); expressing as a fusion protein in an appropriate host and isolating it; and then treating the fusion protein with an applicable enzyme.

An example of the protein of the present invention includes a protein comprising an amino acid sequence shown in SEQ ID NO:1. In addition, the present invention even comprises the derivatives of the protein of the present invention which comprise a conversion (i.e., a substitution, deletion, insertion and/or addition) in a portion of the amino acid sequence.

Examples of protein derivatives of the present invention can have improved stability or persistence in vivo, and reduced immunogenicity by e.g. a conversion (a substitution, deletion, insertion and/or addition) of amino acids, the acylation of N-terminus, and the binding of water soluble polymers such as polyethylene glycol to α-amino group or ε-amino group.

As a general method of improving the thermodynamic stability of protein, it has been theoretically shown that the introduction of proline residue and the removal of glycine residue are effective (Matthews et al., *Proc. Natl. Acad. Sci. U.S.A.* 84, 6663–6667, 1987). Thus, to improve the stability of the protein derivatives of the present invention, designing a protein derivative into which a proline residue is introduced and a protein derivative where glycine residue is removed, has been considered.

Since the comformation of a protein is generally formed so that the protein has hydrophobic amino acids inside and hydrophilic amino acids outside, the improvement of the solubility of the protein can be expected by substituting amino acids existing on the protein surface by more hydrophilic charged amino acids. Also the protein derivatives of the present invention can be designed from this point of view.

In addition, there can also be applied the amino acid sequences of galectin-1 from other species having homology with human galectin-1 (e.g. chicken galectin: Ohyama, Y et al., *Biochem. Biophys, Res. Commum. vol.*134, p. 51–56 (1986); rat galectin: Clerch, L. B. et al., *Biochemistry, vol.*27, p. 692–699 (1988), mouse galectin: Wilson, T. J. G. et al., *Biochem. J. vol.*261, p. 847–852 (1989), bovine galectin: Abbot, W. M. et al., *Biochem. J. vol.*259, p. 283–290 (1989), etc.) For example, comparing amino acid sequences between human and rat, there can be selected either a site which has proline for rat, but an amino acid other than proline for human, or another site which has glycine for human, but an amino acid other than glycine for rat.

Furthermore, the proteins of the present invention include the human protein of the present invention having an amino acid sequence shown in SEQ ID NO:1 or derivatives thereof, wherein lysine and methionine residues are added to the positions −1 and −2, or wherein a methionine residue is added to the position −1. It is known that, when an expression is carried out in a cell using bacteria (e.g. *Escherichia coli*) as a host, there may be obtained a protein, wherein an initiation methionine residue is added to the N-terminal side of protein having a nerve regeneration promoting activity. In addition, depending on hosts, the generated protein with a nerve regeneration promoting activity may be glycosylated, or the N-terminus of the generated protein may or may not be blocked by an acetyl residue, formyl residue or the like. The protein of the present invention also comprises these kinds of proteins.

The protein of the present invention may be purified and isolated from natural sources (e.g. a conditioned medium having a nerve regeneration promoting activity, or human lung, kidney, placenta, etc.), but it is preferably obtained by gene recombination. With the latter method, there is the advantage that mass production is possible.

When the protein of the present invention is purified from natural sources or recombinant cells, one or more general protein purification methods set forth below can be used in combination: salting out, ammonium sulfate fractionation, solvent extraction, HPLC, affinity chromatography, ion exchange chromatography, lectin affinity chromatography, pigment adsorption chromatography, hydrophobic interaction chromatography, gel filtration chromatography, reversed phase chromatography, heparin affinity chromatography, sulfated gel chromatography, hydroxyl apatite chromatography, metallic chelating chromatography, isoelectric chromatography, preparative scale electrophoresis, isoelectric focusing method and so on. Otherwise, the physicochemical properties of the protein of the present invention, which can be assumed from Examples described later, can also be used. In addition, an antibody column using an antibody capable of recognizing the protein of the present invention can also be used.

Regarding the amino acid sequence of the protein of the present invention comprising 6 cysteine residues, it is desirable that it exists in a state where it is cross-bridged (oxidized) with a disulfide bond(s). The oxidation methods of converting a reduced protein to an oxidized protein include a chemical oxidation method or a disulfide exchange reaction. The chemical oxidation methods include an air oxidation method, an air oxidation method wherein heavy metallic ion (e.g. $Cu^{2+}$) is used as a catalyst, a method wherein iodosobenzoic acid, hydrogen peroxide or the like is used, and so on. A typical example of disulfide exchange reaction is a method wherein a redox buffer containing both reduced and oxidized glutathiones is used, but a method wherein a redox buffer containing cysteine, dithiothreitol, 2-mercaptoethanol and cysteamine can also be used. Thus, the protein of the present invention having a disulfide bond(s) at least between Cys on the 16-position (Cys16) and Cys on the 88-position (Cys88) among cysteine residues on the 2-position (Cys2), 16-position (Cys16), 42-position (Cys42), 60-position (Cys60), 88-position (Cys88) and 130-position (Cys130) can be obtained. The protein comprises 1 to 3 disulfide bond(s), preferably 2 to 3 disulfide bonds, and more preferably 3 disulfide bonds. When the refolding of protein is carried out expressing DNA encoding an amino acid sequence of SEQ ID NO:1 in *Escherichia coli*, the protein is obtained as a mixture which consists of the following 3 types of oxidized galectin-1 having a disulfide bond between each cysteine: (1) Cys16–Cys88, Cys2–Cys130 and Cys42–Cys60; (2) Cys16–Cys88, Cys2–Cys60 and Cys42–Cys130; and (3) Cys16–Cys88, Cys2–Cys42 and Cys60–Cys130, and further comprises more than 50% of galectin-1 of the above (1). When the above DNA is expressed in a COS1 cell, the oxidized galectin-1 of the above (1) is mainly obtained. When a high-performance reversed phase chromatography, wherein acetonitrile concentration in 0.1% TFA increases linearly 32% to 40% for 60 minutes at room temperature, is carried out using YMC Protein RP (10 mm×250 mm, YMC) as a column, the oxidized galectin-1 expressed in *Escherichia coli* is eluted, as approx. 36% acetonitrile concentration (in the case of form (1)) and approx. 34% acetonitrile concentration (in the case of forms (2) and (3)). When a high-performance reversed phase chromatography, wherein acetonitrile concentration in 0.1% TFA increases linearly 32% to 44% for 45 minutes at room temperature, is carried out using YMC Protein RP (4.6 mm×150 mm, YMC) as a column, in the case of form (1), the oxidized galectin-1 expressed in a COS1 cell is eluted as approx. 38% acetonitrile concentration.

Pharmaceutical Composition

The present invention includes remedies for neuropathy involving nerve injury, nerve degeneration, hypofunction at nerve grafting and so on which contain as an active ingredient the above-defined galectin-1 or its derivatives.

The remedies may include a diluent, antiseptic, solubilizer, emulsifier or adjuvant, as well as a general appropriate liquid or solid carrier (Remington: *The Science and Practice of Pharmacy*, Nineteenth Edition, Mack Publishing Company, 1995). Such a pharmaceutical composition has a liquid or solid form, and is able to be mixed with a diluent selected from buffers having various pH and ionic strength (e.g. Tris-hydrochloric acid, acetate, phosphate), an additive such as albumin or gelatin for preventing surface adsorption, a surfactant (e.g. Tween 20, Tween 80, Pluronic F68, bile salt), a solubilizer (e.g. glycerol and polyethylene glycol), an antioxidant (e.g. ascorbic acid and sodium metabisulfite), an antiseptic (e.g. thimerosal, benzyl alcohol, paraben), and an excipient or an isotonizing agent (e.g. lactose and mannitol).

Furthermore, the properties of the pharmaceutical composition of the present invention include a covalent bond between the protein and a water soluble polymer such as polyethylene glycol; chelate complexation with metallic ions; or the uptake of the above substance into a granular formulation of polymerized compound such as polylactate, polyglycolate or hydrogel, or onto its surface, or into a liposome, microemulsion, micelle, monolayer- or multilayer-caveola, erythrocyte ghost, or spheroplast. The composition having the above-stated characteristics has an influence on the physical condition, solubility, stability, in vivo release rate, and in vivo clearance of the protein of the present invention. So, the composition is selected depending on the physical and chemical properties of the protein having nerve regeneration promoting activity.

The remedies of the present invention can have various administration routes including parenteral, transpulmonary, transnasal, peroral or local imbedding administration. And, depending on these administration routes, processes such as granulation, protective coating, mixing with protease inhibitor, mixing with absorbefacient, enclosure in biological materials or biocompatible materials such as collagen can be applied to the remedies. The dosage forms include solution, suspension, emulsion, tablet, pill, capsule, aerosol, enteric coated tablet, sustained release preparation, imbedding preparation and the like, but are not limited thereto. In the embodiment of the present invention, the protein of the present invention may be contained in collagen, to directly be imbedded into a neurological location, but for example, necessary ingredients such as agent or carrier can be included into a tube made of a biocompatible material (e.g. silicone rubber, collagen, polypropylene, polyester, polyamide, etc.)

Regarding remedies comprising the protein of the present invention, generally 0.01 µg/kg body weight to 1 mg/kg body weight can be administered as an active ingredient one to several times per day, according to age, body weight, symptom, sex, administration route and so on. However, the dosage is not limited to the above range, and it can vary on various therapeutical factors.

The combined use of the protein of the present invention with a single or other additive neurotrophic activity factor groups is useful for treating a large number of nervous system disorders. Other additive factors include a member of the neurotrophin family including NGF, BDNF, NT-3, NT-4/5, NT-6 and the like; the insulin family including insulin, IGF-I, IGF-II and the like; the FGF family including aFGF, bFGF, FGF-5 and the like; the interleukin group including IL-1, IL-2, IL-3, IL-6 and the like; and LIF, GM-CSF, G-CSF, EPO, TPO, CNTF, oncostatin M, TNF α, thioredoxin, GDNF, TGF β, EGF, growth promoting activity, growth inhibitory factor, plasminogen, glia-derived nexin, $\alpha_2$ macroglobulin, S100 protein, annexin V, neuron specific enolase, thrombospondin, and hepatocyte growth factor. Furthermore, neuro-peptides including ganglioside such as GM1 and GM2, adrenocorticotropic hormone (ATCH), thyrotropin-releasing hormone (TRH), hippocampal cholinergic neurotrophic peptide (HCNP), corticotropin-releasing hormone (CRF) and the like are also included to the protein of the present invention. Among them, NGF, BDNF, NT-3, NT-4/5, NT-6, IGF-I, IGF-II, CNTF and GDNF are desirable.

Moreover, the combined use of the protein of the present invention with an extracellular matrix or paraneural system cell is also useful for treating nervous system disorders. Extracellular matrixes include laminin, fibronectin, thrombospondin, collagen and the like. Paraneural system cells include Schwann cell, fibroblast, satellite cell, microphage, glia cell and the like. In addition, the combined use of paraneural system cells with basal membranes is also useful for treating nervous system disorders.

According to in vitro and in vivo experiments, the protein of the present invention has been proved to promote axonal regeneration and remyelinization from nerve injuries due to denervation, crush, freezing of nerves. The system wherein a dorsal root ganglion associated a nerve stumps was embedded into a collagen gel and the effect of axonal regeneration from a nerve stumps was examined (Horie H. et at. *Neurosci Lett* 121, 125–128 (1991); Horie H. et al. *NeuroReport* 2, 521–524 (1991)) showed a clear axonal regeneration effect. Further, even in vivo, there was shown a nerve regeneration effect from nerve injuries due to the denervation, crush and freezing of an sciatic nerve. Referring to previously reported methods (S. Varon, et at, pp. 101–122 in "*Frontiers of clinical neuroscience, vol.6 Neural Regeneration and Transplantation*" edited by F. J. Seil (Alan R Liss, Inc.) (1989); G. Lundborg, et al., *Exp. Neurol.*, 76, 361–375 (1982); L R Williams, et al, *J. Comp. Neurol.*, 218, 460–470 (1983); Q. Zao, et al., *Restor. Neurol, Neurosci.*, 5, 197–204 (1993)), a silicon chamber was attached to an sciatic nerve, and axonal regeneration in the chamber was observed. As a result of this experiment, it was shown that the protein of the present invention promotes axonal regeneration in the chamber filling collagen gels. Furthermore, as a result of another experiment which involved inflicting injuries, including crushing and freezing, to an sciatic nerve, followed by observing the damaged part with an electron microscope (A Seto, Hasegawa M, Uchiyama N, Yamashima T, Yamashita J: *J Neuropathol Exp Neurol* 56:1182–1190 (1997)), it was clear that the administration of the protein of the present invention promotes axonal regeneration and remyelinization. From the results of these experiments regarding the nerve regeneration promoting effect, the protein of the present invention is considered to be useful for treating neuropathy involving various nerve injuries, nerve degeneration and the like, which are attended with the regression or demyelination of axons.

The main uses of the protein of the present invention are the promotion of nerve regeneration and function recovery from central and peripheral nerve injuries suffered from an accidental injury or surgical operation. Or, another use of the protein is treating for nerve injuries suffered as a result of curative treatments such as chemotherapy and radiation treatment for cancers, AIDS and the like. In addition, this protein can be administered to neuropathies which are caused by central and peripheral nerve injuries suffered from chemical substances such as agent, heavy metal and alcohol. Such neuropathies may be caused by nerve injuries which are suffered as a result of ischaemia, infection, malignant tumor or metabolic disorder, e.g. diabetic neuropathy or the dysfunction of kidney or liver. Further, such neuropathies may also be caused by the degeneration of specific nerve system cells, e.g. one of motor nerve degenerative diseases, amyotrophic lateral sclerosis, and one of neuro-degenerative diseases, Alzheimer's disease, which are motor nerve degenerative diseases. The protein of the present invention can be used for the treatment of neuropathy caused by the nerve injury or nerve degeneration stated above. In addition, it can be administered to patients at peripheral nerve or artificial nerve grafting for nerve injury. Furthermore, it is also useful for nervous function disorder due to productive disorder.

The present invention further provides a method of producing the protein of the present invention using an antibody column. This antibody column can be obtained by binding an antibody cross-reacting with the protein of the present invention to a supporting medium of column. In this case, the entire protein or its fragment having an antigen determinant can be used as an antigen. The antibody herein includes both monoclonal and polyclonal antibodies and a chimeric antibody produced by the known methods, i.e., a "recombinant" antibody. Generally, polyclonal antibody includes various antibodies against various antigen determinants (epitopes), whereas monoclonal antibody is an antibody against a single antigen determinant on an antigen.

Regarding polyclonal antibody, the antiserum can be obtained by a process of emulsifying the protein of the present invention to Freund's complete adjuvant, immunizing a rabbit, mouse, rat, guinea pig or sheep, boosting at intervals of two weeks using Freund's incomplete adjuvant and then bleeding. A specific antibody against the protein of the present invention can be obtained, if necessary, by carrying out an ammonium sulfate fractionation for the obtained antiserum to roughly purify IgG, and then absorbing the roughly purified product with an affinity column to which a purified protein is bound (e.g. the use of CNBr activating Sepharose).

An advantage of monoclonal antibodies is that these antibodies can be synthesized by hybridoma in a culture medium into which no other immunoglobulins are mixed. Monoclonal antibodies are prepared from the culture supernatant of hybridoma, or from mouse abdominal dropsy which is induced by inoculating hybridoma into its abdominal cavity. Hybridoma technique firstly described by Kohler and Milstein (*Eur. J. Immunol.* 6, 511–519 (1976)) can broadly be used to generate hybrid cell systems having high-level monoclonal antibodies against a large number of specific antigens. Monoclonal antibodies can be prepared by the following process: The protein of the present invention, along with an adjuvant such as a dead cell body, is injected into the abdominal cavity of mouse (e.g. BALB/c) to immunize it, and after a booster immunity confirming the generation of antibody, and the spleen is extirpated from the mouse. After splenic cells are prepared, those cells are quickly fused with a myelomain cell strain (e.g. X63, NS-1) in a HAT-medium (containing hypoxanthine, aminopterin and thymidine) in the presence of polyethylene glycol (e.g. #4000). After HAT selection of hybridoma and the screening of a specific antibody-generating cell, this cell is injected into a mouse's abdominal cavity and cloned to obtain a monoclonal antibody. The detailed method of preparing a monoclonal antibody is described, for example, in Tatsuo Iwasaki et al, "*Monoclonal Antibodies—Hybridoma and ELISA*" (1987) Kodansha Scientific, Tokyo, Japan.

The protein of the present invention can be separated and purified by a process of: preparing an antibody column by binding the above-obtained antibodies to gels such as an agarose gel of Sepharose (Pharmacia) activated with cyanogen bromide; passing liquid derived from natural sources (e.g. a conditioned medium having a nerve regeneration promoting activity, or a human lung, kidney, placenta, etc.), recombinant cells or cultures through the column to absorb it; and eluting the protein of the present invention using salt concentration gradient, pH change and a denaturizing agent.

In order to stabilize the remedies containing the protein of the present invention, stabilizers such as saccharides and surfactants can be used. Examples of stabilizers include the following:

Saccharides used as a stabilizer include mannitol, lactose, sucrose, maltose, glucose, inositol, xylose, sorbitol, fructose, galactose, ribose, mannose, cellobiose, cyclodextrin, etc. Among these, sorbitol, mannitol and sucrose are preferable.

Surfactants used for the stabilizer include polyoxyethylene hydrogenated castor oil; polyoxyethylene castor oil; polyoxyethylene sorbitan fatty acid ester such as polysorbate 80 and polyoxyethylene sorbitan monolaurate (sometimes called polysorbate 20); sorbitan fatty acid ester such as polyoxyethylene polyoxypropylene glycol and sorbitan monooleate; sucrose fatty acid ester such as sucrose monolauric acid ester; benzethonium chloride; aromatic quaternary ammonium salt such as benzalkonium chloride; sodium caprylate; sodium sulfite, etc. Among these, polysorbate 80, polysorbate 20 and polyoxyethylene hydrogenated castor oil are preferable.

In the remedies of the present invention, these saccharides can be used within a range from 0.1 to 50% (w/v), and the surfactants within a range from 0.0001 to 50% (w/v).

The remedies containing the protein of the present invention do not only include the above-stated various proteins having a neurotrophic activity, but also the protein of the present invention which is chemically modified by binding to at least one water soluble polymer. The water soluble polymers are selected from e.g. polyethylene glycol, monomethoxy-polyethylene glycol, dextran, poly(N-vinylpyrrolidone) polyethylene glycol, propylene glycol homopolymer, polypropylene oxido/ethylene oxide copolymer, polyvinyl alcohol, etc. These polymers can form covalent bonds through an α-amino group at N-terminal of protein or a ε-amino group of lysine and a reaction group such as aldehyde. It is particularly preferable for the present invention that, by reacting the reactive PEG molecule with the protein of the present invention, reactive polyethylene glycol (PEG) is added thereto. Further, the molecular weight of PEG is preferably from 6 kDa to 50 kDa.

The protein of the present invention is useful as a nerve regeneration promoting agent for neuropathy which promotes axonal regeneration and the recovery of nerve tissues, and supports their survival, as described above and below.

EXAMPLES

The present invention will now be further described with examples, but not limited thereto.

Regeneration of peripheral nerves was evaluated in vitro in the following examples.

The dorsal root ganglion (DRG) with nerve stumps was excised from an animal and then cultured in collagen gel. The cultured system was used as an in vitro model. Using this system, assay for axonal regeneration and for neural survival activity by a factor were performed as described previously (H. Horie et al., NeuroReport, 8, 1955–1959, 1997). DRGs (T2 to T11) with nerve bundles, 1 to 2 mm in length, were excised from a 3-month-old Wistar rat. The DRG was placed in a collagen solution [which was prepared by mixing (A) a solution of 0.5% collagen (type I) dissolved in a diluted acetic acid solution, (B) a 10-fold concentrated minimum essential medium (MEM), and (C) 100 ml of a solution containing 2.2 g of $NaHCO_3$ and 4.77 g of HEPES dissolved in 0.05 NNaOH at a ratio of A:B:C=8:1:1 (by volume)] on a culture dish on ice. The dish was heated at once to 37° C., kept at 37° C. for 5 minutes, so that the collagen solution was converted to a gel phase. Subsequently, the dish was filled with Ham's F12 medium containing 5 µg/ml of insulin, 5 µg/ml of transferrin, 20 nM progesteron, 30 nM sodium selenite, and 0.1 mM putrescine, and then cultured at 37° C. in the air saturated with vapor containing 5% $CO_2$.

Nerve regeneration-promoting factors at various concentrations and fractionated fractions being subjected to purification were added to the medium and cultured for 6 to 7 days. The number of regenerating axons from the transected nerve ends was measured under a phase contrast microscope. For each DRG, peripheral and central transected nerve ends were separately measured for the number of regenerating axons. Average and standard error were calculated for each of all DRG measured, and the significance of the activity was statistically evaluated.

Example 1
Purification of mRNA from Rat Primary-Cultured Hepatocytes

Since Horie H. et al. found a nerve regeneration-promoting activity in the supernatant of a rat hepatocyte primary culture (Neuroreport, 2, 521–524, 1991), this primary-cultured cell was selected as a material for cDNA cloning of a rat nerve regeneration-promoting factor and subjected to the following experiments.

Total RNA was extracted using ISOGEN [RNA extraction reagent manufactured by NIPPON GENE; AGPC method (Chomczynski P, et al., Anal. Biochem. 162, 156–159, 1987)]. Rat hepatocytes were prepared by the enzyme perfusion method (Toshikazu Nakamura, Laboratory Procedures for Hapatic Primary Cell Culture, 1987, Gakkai Shuppan Center, Tokyo, Japan), and cultured in a collagen-coated culture flask containing a serum free culture medium that had been prepared by adding 5 µg/ml of insulin (manufactured by SIGMA), 0.01 µg/ml of EFG (manufactured by TOYOBO CO., LTD., Japan), and 0.3 µg/ml of aprotinin (manufactured by SIGMA) to William's E medium. The primary cell culture prepared from the liver of a 8-week-old rat were inoculated at $8 \times 10^6$ cells per flask, into twenty five 175 $cm^2$ culture flasks (manufactured by Falcon), and then cultured in an incubator in 5% $CO_2$ gas at 37° C. for 2 days. Next the culture medium was removed from each flask, 4 ml of ISOGEN was added per flask followed by thorough suspension, thereby collecting the mixture. Using a 50 ml syringe with a 22G injection needle, suction and ejection of the mixture was repeated about 20 times until the mixture almost lost its viscosity. 20 ml of chloroform was added and mixed with the mixture, followed by centrifugation at 12,000 G for 15 minutes. The supernatant was carefully transferred into another tube, and 50 ml of isopropyl alcohol was added to the tube and mixed, followed by centrifugation at 12,000 G for 10 minutes. The resultant pellet was washed once with a small quantity of 70% ethanol, thereby obtaining approximately 2 mg of total RNA from approximately $2 \times 10^8$ hepatocytes.

Poly $(A)^+$ RNA was purified from the total RNA using mRNA Purification Kit (manufactured by Pharmacia Corporation; method using Oligo dT cellulose). 90 µg of poly $(A)^+$ RNA was obtained from approximately 2 mg of the total RNA.

Example 2
Construction of cDNA Library Derived from Rat Primary-Cultured Hepatocytes for Expression Cloning Double-stranded cDNA, having an EcoRI recognition site on the Met side and a NotI recognition site on the Poly (A) side, was synthesized using TimeSaver™ cDNA Synthesis Kit [manufactured by Pharmacia; a kit for cDNA synthesis based on modified Gubler & Hoffman method (Gene 25, 263–269, 1983)] and DIRECTIONAL CLONING TOOL-BOX [manufactured by Pharmacia Corporation; a set containing a primer for cDNA synthesis having NotI sequence: 5'-AACTGGAAGAATTCGCGGCCGCAGGAA(T)$_{18}$-3' (SEQ ID NO:11) and adaptors for addition of EcoRI sequence: 5'-AATTCGGCACGAGG-3' (SEQ ID NO:12), and 5'-CCTCGTGCCG-3'] (SEQ ID NO: 63) from 5 µg of poly $(A)^+$ RNA obtained in Example 1. Two third of the synthesized cDNA was linked to an 1.5 µg of the expression vector pEF18S that had previously been digested with EcoRI and NotI (Ohashi H. et al., Proc. Natl. Acad. Sci. USA 91, 158–162, 1994). Next the product was divided into 12 equal parts, and each part was transformed into 1000 µl of Competent High *E. coli* DH5 (manufactured by TOYOBO CO., LTD., Japan). As a result, 12 pools of cDNA library, each having $8.3 \times 10^4$ transformants, were prepared ($1.0 \times 10^6$ transformants in total).

Example 3
Preparation of pRLF cDNA by Expression Cloning

Each pool of the cDNA library of rat primary-cultured hepatocyte as prepared in Example 2 was cultured overnight in 15 ml of 2×LB medium (2% Tryptone, 1% yeast extract, 1% NaCl, 0.2% Glucose) containing 50 µg/ml of ampicillin. 0.5 ml of pressure-sterilized glycerin was added and mixed with 0.5 ml of the cultured solution, and the mixture was stored at −80° C. 200 µl of the stored cell solution was cultured overnight in 50 ml of LB medium (1% Tryptone, 0.5% yeast extract, 0.5% NaCl, 0.1% Glucose) containing 50 µg/1 ml of Ampicillin. Subsequently plasmid DNA was extracted basically as described in Molecular Cloning (Sambrook et al., Cold Spring Harbor Laboratory Press, 1989). The 50 µg out of the total 200 µg of the extracted plasmid DNA was transfected into COS1 cells according to the slightly modified DEAE-dextran method including chloroquine treatment (Sompayrac LM, et al., Proc. Natl. Acad. Sci. USA 78, 7575–7578, 1981; Luthman H, et al., Nucl. Acids Res., 11, 1295–1308, 1983) as shown below. $1.5 \times 10^6$ COS1 cells (ATCC CRL1650) suspended in Iscove's Modified Dulbecco's Medium (IMDM) containing 10% fetal calf serum (FCS) were inoculated onto plastic tissue culture flask (manufactured by CORNING) with 225 $cm^2$ culture surface area coated with cell matrix (manufactured by IWAKI GLASS CO., LTD., Japan), and then cultured overnight in an incubator with 5% $CO_2$ gas at 37° C. On the other hand, each pool of the plasmid DNA that had been dissolved in 250 µl of HBS (21 mM HEPES—145 mM NaCl, pH 7.1) was mixed with 25 ml of IMDM containing 250 mg/ml of DEAE-dextran (manufactured by Pharmacia), 48 mM chloroquine (manufactured by SIGMA) and 8% (v/v) Nu-Serum (manufactured by Collaborative). Immediately before transfection, the mixture was added to the above-described COS 1 cells that had been washed twice with IMDM. The mixture was cultured in an incubator with 5% $CO_2$ gas for 3 hours at 37° C. Subsequently the culture supernatant was removed by suction and the flask was washed twice with IMDM. 65 ml of IMDM containing 0.02% bovine serum albumin, 20 µg/ml of human insulin (manufactured by GIBCO BRL), 20 µg/ml of human transferrin (manufactured by GIBCO BRL), 40 µM monoethanolamine (manufactured by SIGMA), and 0.1 µM sodium selenite (manufactured by SIGMA) was added, and then the cell was cultured in an incubator with 5% $CO_2$ gas for 3 days at 37° C., followed by collection of a culture supernatant. The supernatant was thoroughly dialyzed against a F12 medium, and then the nerve regeneration-promoting activity was measured in the above-mentioned in vitro assay system. As a result, nerve regeneration-promoting activity was identified in the culture supernatant of COS1 cells that had been transfected with a pool of the plasmid DNA.

Next, the stored bacterial pool, in which the activity had been found, was diluted $1:10^5$ in CIRCLEGROW™ medium (manufactured by BIO 101) containing 50 µg/ml of Ampicillin. Then 2.5 ml each of the diluted solution was dispensed into 18 tubes, and then cultured overnight. [50 µl of an aliquot was spread over LB agar medium (supplemented with 1.5% agar) containing Ampicillin, and then cultured overnight at 37° C. By counting the number of colonies appeared on the medium, it was confirmed that one tube contained $8.2 \times 10^3$ cDNA clones. That is, a pool containing $8.2 \times 10^3$ clones was generated.] 0.5 ml of pressure-sterilized glycerol was added to 0.5 ml of the culture solution, and then stored at −80%. Plasmid DNA was purified from the remaining 2 ml as described above, thereby obtaining 5 µg of the plasmid DNA per pool. Further, the plasmid DNA was transfected into COS1 cells as described above. From now, the experiment was scaled down using petri-dishes with 60 mm diameter. Nerve regeneration-promoting activity in the resulting culture supernatant was measured, thereby obtaining one pool with the activity. The number of cDNA clones contained in the pool with the activity was reduced from $8.3 \times 10^4$ to $8.2 \times 10^3$, $1.5 \times 10^3$, and 220 in order by repeating such screening. When two or more pools having the activity were obtained in a single round of screening, one of these pools was used for the next round of screening. When the number of clones of the pool reached 220, the stored bacterial pool was diluted, inoculated on LB agar medium containing Ampicillin, and then cultured overnight for the sake of formation of colonies. 540 colonies were individually picked up from the formed colonies. 20 of these colonies were inoculated together in 2.5 ml of CIRCLEGROW™ medium (manufactured by BIO 101) containing 50 µg/ml of Ampicillin, thereby obtaining 27 pools. Plasmid DNA was purified from 2 ml of each overnight culture pool as described above and transfected into COS1 cells, and then the presence of a nerve regeneration-promoting activity in the culture supernatant was measured. Thus, a pool having the activity was obtained. Plasmid DNA was purified from each of the 20 colonies contained in the pool with the activity, as described above. Then the plasmid DNA was transfected into a COS1 cell, and the nerve regeneration-promoting activity in the culture supernatants was measured. A cDNA clone having the activity was eventually obtained and named pRLF.

Example 4
Sequence Analysis of Rat pRLF cDNA

The plasmid DNA of the cDNA clone pRLF obtained in Example 3 was purified basically as described in Molecular Cloning (Sambrook et al., Cold Spring Harbor Laboratory Press, 1989). Approximately 700 µg of plasmid DNA was obtained from 40 ml of the overnight culture of pRLF clone in CIRCLEGROW™ medium containing 50 µg/ml of ampicillin. The obtained plasmid DNA was amplified by PCR using universal primers and oligonucleotide primers of approximately 20 bases that had been synthesized based on the determined cDNA sequence, and using Taq Dye Deoxy™ Terminator Cycle Sequencing Kit (manufactured by Perkin-Elmer Corporation; dideoxy method using fluorescent dye and PCR: Sanger F. et al., Proc. Natl. Acad. Sci. USA 74, 5463–5467, 1977). [The oligonucleotide primers of approximately 20 bases had been synthesized using a 394 DNA/RNA synthesizer (manufactured by Perkin-Elmer Corporation) which is based on the β-cyanoethyl amidite method. Purification of synthetic DNA was performed using an OPC column (manufactured by Perkin-Elmer Corporation). The OPC column is filled with reversed phase silica gel and is used to purify synthetic DNA having trityl group. The purified synthetic DNA was dissolved in TE solution to 20 µM and stored at −20° C. until use.] Then the cDNA nucleotide sequence was determined by a 373A DNA sequencer (fluorescent sequencer, manufactured by Applied Biosystems).

The nucleotide sequence was shown in the Sequence Listing (SEQ ID NO: 2).

Example 5
Detection of pRLF mRNA in Various Rat Tissues

To determine if pRLF is a full-length clone of interest and which organ produces mRNA of interest, Northern blotting was performed using Rat Multiple Tissue Northern Blot [manufactured by CLONTECH; nylon membrane to which poly (A)+ RNAs from different rat tissues were blotted]. Northern blotting was performed basically as described in Molecular Cloning (Sambrook et al., Cold Spring Harbor Laboratory Press, 1989). Prehybridization was conducted for 1 hour at 42° C. in 20 ml of a solution containing 50% formamide, 5×SSC, 5× Denhardt's solution, 1% SDS, and 200 µg/ml of salmon sperm DNA. Probes used herein were prepared by digesting pRLF with restriction enzymes NotI and EcoRI, separating cDNA fragments of approximately 600 bp by electrophoresis using 0.8% agarose gel (manufactured by FMC BioProducts), purifying the fragments using Prep-A-Gene DNA purification Kit (manufactured by Bio-Rad Laboratories, Inc.), and labeling the products with $^{32}$P using a Random Primer DNA labeling kit (manufactured by Takara Shuzo Co., Ltd., Japan; a kit based on the random primer method described in Anal. Biochem., 132, −13, 1983). Hybridization was conducted by adding the probes to 20 ml of a solution with the same composition as used in prehybridization and allowing the mixture to react for 20 hours at 42° C. The filter was washed in 2×SSC/0.1% SDS solution for 5 minutes at room temperature, and washed twice in 0.1×SSC/0.1. % SDS solution for 30 minutes at 68° C., followed by analysis using a FUJIX bio-image analyzer BAS 2000 (manufactured by Fuji Photo Film Co., Ltd., Japan). As a result, the expression of mRNA was seen in the heart, brain, spleen, lung, liver, skeletal muscle, and kidney, with relatively high expression in the lung and liver (FIG. 1). Since the strand length of a band is about 1.6 Kb, pRLF was thought to be an incomplete length clone.

Example 6

Isolation of a Full-Length Clone of pRLF

The 5' terminal was recovered by the 5' RACE method because pRLF was thought to be an incomplete length clone based on the results of Example 5. First, two PCR primers were synthesized, which correspond to the most upstream of the cDNA inserted in pRLF. The sequences are as follows:

Flf: 5'-GTGGTCAGGTTTGGCTCATA-3' (complementary to the nucleotides 52–71 of SEQ ID NO:2 in the Sequence Listing; SEQ ID NO:13).

Flg: 5'-TGCTCTTCACAGGCCCCCT-3' (complementary to the nucleotides 33–51 of SEQ ID NO:2 in the Sequence Listing; SEQ ID NO:14).

Further, a primer for sequencing pEF18S was constructed. The sequence is as follows.

EF1α-2: 5'-GGATCTTGGTTCATTCTCAAG-3' (SEQ ID NO:15; located outside EcoRI of a cloning site EcoRI-NotI of pEF18S, toward this cloning site).

PCR was performed using 10 pmol each of the synthesized primers (Flf and EF1α-2) and using the plasmid of the cDNA library (independent clones; $3.2 \times 10^6$) prepared from the mRNA of rat primary-cultured hepatocytes as a template, in a similar manner to that of Examples 1 and 2. Using TaKaRa LA Taq (manufactured by Takara Shuzo Co., Ltd.), PCR was performed in a volume of 100 μl using a GeneAmp™ PCR System 2400 (manufactured by Perkin-Elmer Corporation). The PCR reaction cycle was repeated 35 times after denaturation for 5 minutes at 94° C., each cycle consisting of denaturation for 30 seconds at 94° C., annealing for 30 seconds at 57° C., and synthesis for 2 minutes at 72° C.; followed by synthesis for further 5 minutes at 72° C. Further, PCR was performed under the same conditions as described above using 10 pmol each of the synthesized primers, Flg and EF1α-2, and using 1 μl of the reaction solution diluted 4-fold as a template. The reaction solution was subjected to electrophoresis using 2% agarose gel. Thus a relatively large and clear band was recovered and the product was purified therefrom using Prep-A-Gene DNA Purification Kit. The nucleotide sequence of this fragment was analyzed directly by a type 377 DNA sequencer (manufactured by Perkin-Elmer Corporation) using the synthesized primers, Flg and Ef1α-2, and using a Taq Dye Deoxy™ Terminator Cycle Sequencing FS Kit (manufactured by Perkin-Elmer Corporation). Thus an upstream sequence of 332 bases was obtained (SEQ ID NO: 3). However, since it was still short of the analytical result of Northern blotting (total length of approximately 1.6 Kb), the following 5' RACE was further repeated. First, two PCR primers were synthesized, which correspond to the N terminal side of the obtained upstream sequence. The sequences are as follows:

Flh: 5'-CCAAGTCCGTATCTCCATCA-3' (complementary to the nucleotides 118–137 of SEQ ID NO: 3 in the Sequence Listing; SEQ ID NO:16).

Fli: 5'-GGCAGTCCAGTATGCTACAT-3' (complementary to the nucleotides 36–55 of SEQ ID NO: 3 in the Sequence Listing; SEQ D NO: 17).

PCR was performed using 10 pmol each of the synthesized primer, Flh, and Anchor Primer (attached to 5'-RACE-Ready cDNA; corresponding to an anchor added to the 5' end of the cDNA) and using rat spleen 5'-RACE-Ready cDNA (manufactured by CLONTECH) as a template. Using TaKaRa LA Taq (manufactured by Takara Shuzo Co., Ltd. Japan), PCR was performed in a volume of 50 μl using GeneAmp™ PCR System 2400 (manufactured by Perkin-Elmer Corporation). The PCR reaction cycle was repeated 30 times, each consisting of denaturation for 45 seconds at 94° C., annealing for 45 seconds at 57° C., and synthesis for 2 minutes at 72° C.; followed by synthesis for further 5 minutes at 72° C. Furthermore, PCR was performed under the same conditions employed above in a volume of 100 μl using 20 pmol each of the synthesized primer, Fli, and Anchor Primer, and using 4 μl of the reaction solution 10-fold diluted as a template. The reaction solution was subjected to electrophoresis using 2% agarose gel. Thus the clearest band was removed and the product was purified therefrom using Prep-A-Gene DNA Purification Kit. This fragment was cloned into a PCR™II vector (TA Cloning™ Kit; manufactured by Invitrogen). PCR was performed using the resultant colonies as templates, and using 7 pmol each of M13 Reverse Primer (5'-CAGGAAACAGCTATGAC-3'; SEQ ID NO:18), M13 (−20) Forward Primer (5'-GTAAAACGACGGCCAGTG-3'; SEQ ID NO:19). That is, the PCR was performed in a volume of 30 μl by GeneAmp™ PCR System 2400 (manufactured by Perkin-Elmer Corporation) using AmpliTaq™ (manufactured by Perkin-Elmer Corporation). The reaction cycle was repeated 35 times after denaturation for 5 minutes at 94° C., each cycle consisting of denaturation for 30 seconds at 94° C., annealing for 30 seconds at 47° C., and synthesis for 1 minute at 72° C.; followed by synthesis for further 5 minutes at 72° C. The reaction solution was subjected to electrophoresis using 2% agarose gel. Thus a band was recovered and the product was purified therefrom using Prep-A-Gene DNA Purification Kit. The nucleotide sequence of this fragment was analyzed by a type 377 DNA sequencer (manufactured by Perkin-Elmer Corporation) using a Taq Dye Deoxy™ Terminator Cycle Sequencing FS Kit (manufactured by Perkin-Elmer Corporation) and using Anchor Primer and Fli. Therefore, a more upstream sequence of 335 bases was obtained (SEQ ID NO:4). At this time, a PCR primer was synthesized, which corresponds to the N terminal of this upstream sequence. The sequence is as follows:

Flj: 5'-TCCTCCTCGACACGCACTCC-3' (complementary to the nucleotides 64–83 of SEQ ID NO:4 in the Sequence Listing; SEQ ID NO:20).

PCR was performed using 20 pmol each of the synthesized primer, Flj, and Anchor Primer, and using 4 μl of the above PCR reaction solution 10-fold diluted, for which rat spleen 5'-RACE-Ready cDNA as a template, and Flh and Anchor Primer had been used. Using TaKaRa LA Taq (manufactured by Takara Shuzo Co., Ltd. Japan), PCR was performed in a volume of 100 μl using a GeneAmp™ PCR System 2400 (manufactured by Perkin-Elmer Corporation). The PCR reaction cycle was repeated 30 times, each consisting of denaturation for 30 seconds at 94° C., annealing for 30 seconds at 63° C., and synthesis for 1.5 minutes at 72° C.; followed by synthesis for 5 minutes at 72° C. The reaction solution was subjected to electrophoresis using 2% agarose gel. Thus the clearest and longest band was recovered and the product was purified therefrom using Prep-A-Gene DNA Purification Kit. This fragment was cloned into a PCR™II vector. Then in the same manner as described above, the fragment was prepared from the colony by PCR, thereby determining its nucleotide sequence. The Primers used herein were M13 Reverse Primer as described above and T7 Primer (5'-TAATACGACTCACTATAGGG-3'; SEQ ID NO: 21). Thus, another upstream sequence of 317 bases (SEQ ID NO:5) was obtained and its full length was 1571 bases (SEQ ID NO:6). Since this full length was consistent with the analytical results of Northern blotting, it was concluded that a complete length clone was obtained.

Homology search was conducted using DNA analysis software "DNASIS" (manufactured by HITACHI SOFTWARE ENGINEERING CO., LTD.). It was shown that the antisense sequence of SEQ ID NO: 6 shared a homology of 85.4% with human Bcl-2 binding component 3 (GENBANK ACCESSION NO. U82987) at nucleotide level. On the other hand, analysis using the same software showed that only ORF of maximum 24 amino acids was present in the clone pRLF (SEQ ID NO:2) that had been obtained by expression cloning. Accordingly, it was thought that protein (peptide) itself encoded by the clone pRLF does not possess nerve regeneration activity, but a substance with nerve regeneration activity may be secreted from COS1 cells by some mechanisms due to introduction of the clone pRLF. To prove the hypothesis, the following experiment was conducted.

Example 7

Purification of Nerve Regeneration-Promoting Factor from Culture Supernatant of pRLF-Transfected COS1 Cells Preparation of Culture Supernatant of pRLF-Transfected COS1 Cells Approximately 300 L of the culture supernatant of pRLF-transfected COS1 cells were prepared to purify a nerve regeneration-promoting factor that is secreted in the culture supernatant of the COS1 cells. This preparation is as described below. First, pRLF clone was shake-cultured in LB medium containing 50 µg/ml of Ampicillin overnight at 37° C. Here, 1.5 L each of this medium was put into a 3L Sakaguchi's flask. Then 170 L of the culture was centrifuged to obtain *E. coli* (wet weight 850 g). Using a plasmid extraction kit (RPM™-4G, manufactured by BIO 101), pRLF plasmid was extracted from 5 g of the *E. coli* per batch. Thus 300 mg of pRLF plasmid was obtained from 170 L of the overnight culture solution.

Transfection of the plasmid pRLF into COS1 cells was performed as described in Example 3. Thus total 294 L of the culture supernatant of pRLF-transfected COS1 cells was obtained and used as a source for purification.

Purification of Nerve Regeneration-Promoting Factor from the Culture Supernatant of pRLF-Transfected COS1 Cell The obtained supernatant was divided into 7 lots, 30 to 50 L each, then purified, because 294 L of the obtained supernatant (total amount of protein; 81678 mg) could not be treated at once. Of these lots, a typical purification is explained for a certain lot. For all purification steps, nerve regeneration-promoting activity was measured using the above-described DRG assay system. Protein was quantified by Coomasie dye binding method (with the reagent manufactured by PIERCE) for steps (1) to (3) and based on absorbance at 280 nm for (4) and following steps. Lots are summarized as follows:

Lot 1: 42.81 L, Protein concentration 0.297 mg/ml Total amount of protein 12698 mg;
Lot 2: 44.73 L, Protein concentration 0.241 mg/ml, Total amount of protein 10760 mg;
Lot 3: 34.16 L, Protein concentration 0.301 mg/ml, Total amount of protein 10290 mg;
Lot 4: 43.05 L, Protein concentration 0.266 mg/ml, Total amount of protein 11438 mg;
Lot 5: 46.30 L, Protein concentration 0.261 mg/mil, Total amount of protein 12070 mg;
Lot 6: 43.92 L, Protein concentration 0.290 mg/mil, Total amount of protein 12752 mg;
Lot 7: 39.15 L, Protein concentration 0.298 mg/ml, Total amount of protein 11670 mg.

(1) Fractionation with Ultrafiltration Membrane

First, Lot 1, the culture supernatant of pRLF-transfected COS1 cells (42.81 L, Protein concentration; 0.297 mg/ml, total amount of protein; 12,698 mg) was centrifuged at 8000 RPM for 30 minutes to remove dead cell debris, thereby collecting the supernatant. Next, the resulting supernatant was filtered through a 100 kDa cutoff ultrafiltration membrane (manufactured by PAUL FILTRON, membrane area 0.46 m$^2$) followed by concentration using a 5 KDa cut-off ultra filtration membrane (manufactured by PAUL FILTRON, membrane area 0.46 m$^2$). The three obtained fractions were a fraction of 5 KDa or less (40.73 L, protein concentration: detection limit or less), a fraction of 5 KDa or more and 100 KDa or less (320 ml, protein concentration: 39.252 mg/ml, total amount of protein: 12560 mg), and a fraction of 100 KDa or more (800 ml, protein concentration: 3.084 mg/ml, total amount of protein: 2467 mg). The three fractions were subjected to DRG assay. Since nerve regeneration-promoting activity was detected in the fraction of 5 KDa or more and 100 KDa or less, this fraction was used for the next step.

(2) TSKgel QAE-TOYOPEARL 550C (Strong Anion Exchange Chromatography)

The fraction of 5 KDa or more and 100 KDa or less obtained in (1) (320 ml, protein concentration: 39.252 mg/ml, total amount of protein: 12560 mg) was diluted 4-fold using 20 mM Tris-HCl buffer (pH 8.0). Subsequently, the diluted solution was loaded at a flow rate of 15 ml/min to a TSKgel QAE-TOYOPEARL 550C column (manufactured by TOSOH CORPORATION, Japan; φ5 cm×10 cm) equilibrated with 20 mM Tris-HCl buffer (pH 8.0) at 4° C. The flow-through fraction was eluted (1900 ml, protein concentration: 0.106 mg/ml, total amount of protein: 201 mg). Next, the eluate was replaced by 20 mM Tris-HCl buffer (pH 8.0) with 750 mM NaCl and loaded to the column at a flow rate of 5 ml/min, so that an adsorbed fraction Q2 was eluted (590 ml, protein concentration: 20.631 mg/ml, total amount of protein: 12172 mg). As a result of DRG assay, nerve regeneration-promoting activity was detected in the adsorbed fraction Q2. Hence, the adsorbed fraction Q2 was used for the next step.

(3) Sephacryl S-200 HR (Gel Filtration Chromatography)

TSKgel QAE-TOYOPEARL 550C column adsorbed fraction Q2 obtained in (2) (590 ml, protein concentration 20.631 mg/ml, total amount of protein 12172 mg) was concentrated to 100 ml using an ultrafiltration unit (manufactured by Amicon; YM3 membrane, 76 mm in diameter). Then, 50 ml of the concentrate 100 ml was loaded at a flow rate of 2.5 mL/min at 4° C. to a Sephacryl S-200 HR column (manufactured by Amersham pharmacia biotech; φ5 cm×100 cm) that had been previously equilibrated with PBS. 50 ml each of the eluate was collected in a tube, and subjected to DRG assay. As a result, nerve regeneration-promoting activity was detected in Fr10 to Fr16, corresponding to the molecular weight ranging from 30 KDa to 5 KDa (350 ml, protein concentration: 4.303 mg/ml, total amount of protein: 1506 mg). Similarly, the remaining 50 ml of concentrate was also fractionated using a Sephacryl S-200 HR column, thereby obtaining active fractions, Fr10 to Fr16 (350 ml, protein concentration: 4.480 mg/ml, total amount of protein: 1568 mg). Sephacryl S-200 HR active fractions thus obtained by two rounds of separate chromatographies were combined (700 ml, protein concentration 4.391 mg/ml, total amount of protein: 3074 mg) and then concentrated to 50 ml using a ultrafiltration unit (manufactured by Amicon; YM3 membrane, 76 mm in diameter). Then, the concentrate was loaded again to a Sephacryl S-200 HR column (manufactured by Pharmacia Biotech, φ5 cm×100 cm) at a flow rate of 2.5 ml/min at 4° C. The eluate was fractionated into 50 ml each, and subjected to DRG assay. As a result, nerve regeneration-promoting activity was detected in Fr13 and 14 corresponding to a molecular weight of 15 Kda (100 ml, protein concentration: 0.224 mg/ml, total amount of protein: 22.039 mg). Thus this fraction was used for the next step.

In this manner, purification steps of (1) to (3) above were conducted for 7 lots, thereby obtaining Sephacryl S-200 HR active fractions for each of these lots. Sephacryl S-200 HR active fractions for each lot are summarized as follows:

Lot 1: 100 ml, Protein concentration 0.224 mg/ml, Total amount of protein 22.039 mg;
Lot 2: 50 ml, Protein concentration 0.313 mg/ml, Total amount of protein 15.672 mg;
Lot 3: 50 ml, Protein concentration 0.366 mg/ml, Total amount of protein 18.300 mg;
Lot 4: 50 ml, Protein concentration 0.316 mg/ml, Total amount of protein 15.800 mg;
Lot 5: 100 ml, Protein concentration 0.230 mg/ml, Total amount of protein 22.950 mg;
Lot 6: 50 ml, Protein concentration 0.305 mg/ml, Total amount of protein 15.240 mg;
Lot 7: 50 ml, Protein concentration 0.245 mg/ml, Total amount of protein 12.250 mg.

(4) Shodex IEC DEAE-2025 (Weak Anion Exchange Chromatography)

Lot 1, Sephacryl S-200 HR active fraction (100 ml, protein concentration: 0.224 mg/ml, total amount of protein: 22.039 mg) and Lot 2, Sephacryl S-200 HR active fraction (50 ml, protein concentration: 0.313 mg/ml, total amount of protein: 15.672 mg) as obtained in (3), were combined (150 ml, protein concentration: 0.251 mg/ml, total amount of protein: 37.711 mg). Then this fraction was concentrated to 5 ml using an ultra filtration unit (manufactured by Amicon; membrane YM3, diameter 76 mm). Subsequently 50 ml of 20 mM Tris-HCl buffer (pH 8.0) was added to the concentrate followed by re-concentration to 5 ml. Another round of this procedure was performed to exchange the buffer with 20 mM Tris-HCl buffer (pH 8.0), thereby obtaining a Sephacryl S-200 HR active fraction (12 ml, protein level: 3.143 mg/ml, total amount of protein: 37.711 mg). Using 20 mM Tris-HCl buffer (pH 8.0) as an eluent A, and 20 mM Tris-HCl buffer (pH 8.0) containing 750 mM NaCl as an eluent B, the fraction was loaded at a flow rate of 2 ml/min to a Shodex EC DEAE-2025 column (manufactured by Showa Denko K.K., Japan; φ2 cm×15 cm) equilibrated with 0% B, at room temperature. After loading, the column was eluted with 20% B in 10 minutes, followed by a 70 minutes linear gradient from 20% B to 60% B. The eluate was fractionated into 4 ml each and then subjected to DRG assay. As a result, nerve regeneration-promoting activity was detected in Fr 39 and 40 having NaCl level of approximately 250 mM (8 ml, protein concentration: 0.02 mg/ml, total amount of protein: 0.16 mg). Thus this fraction was used for the next step.

The remaining lots were purified in the same manner as above, so that Shodex EEC DEAE-2025 active fractions were obtained. That is, the lots were divided into three groups, the combined fraction of Lots 3 and 4, the combined fraction of Lots 5 and 6, and the fraction of Lot 7. Then the groups were separately purified by Shodex EC DEAE-2025, thereby obtaining Shodex IEC DEAE-2025 active fractions.

The Shodex IEC DEAE-2025 active fractions for each of the group of lots was summarized below:
Lot 1 & 2: 8 ml, protein concentration: 0.02 mg/ml, total amount of protein: 0.16 mg;
Lot 3 & 4: 8 ml, protein concentration: 0.02 mg/ml, total amount of protein: 0.16 mg;
Lot 5 & 6: 8 ml, protein concentration: 0.025 mg/ml, total amount of protein: 0.2 mg;
Lot 7: 8 ml, protein concentration: 0.01 mg/ml, total amount of protein: 0.08 mg.

(5) YMC-Pack Protein RP (Reverse Phase Chromatography)

The Shodex IEC DEAE-2025 active fractions of each group of lots as obtained in (4) were combined (32 ml, protein level: 0.0188 mg/ml, total amount of protein 0.6 mg). Then the combined fraction was concentrated to 4 ml using a ultrafiltration unit (manufactured by Amicon; membrane YM 3, diameter 43 mm). 0.5 ml of 2-propanol, 0.5 ml of acetonitrile, and 0.0025 ml of trifluoroacetic acid (TFA) were added to the concentrate so that the concentrate became a final volume of 5.0025 ml, final organic solvent concentration of 20%, and 0.05% of TFA concentration. This mixture was loaded at a flow rate of 0.2 ml/min to a YMC-Pack PROTEIN RP column (manufactured by YMC, φ2.1 mm×150 mm) equilibrated with 40% B, using 2-propanol/acetonitrile 1/1 (volume ratio) that contained 0.1% TFA as an eluent A and 0.08% TFA as an eluent B. After loading, the column was developed with a 30 minutes linear gradient from 40% B to 60% B. The eluate was fractionated into 0.4 ml each, and then subjected to DRG assay. Thus nerve regeneration-promoting activity was detected in Fr 44 and 45 having an organic solvent concentration of approximately 50% (0.8 ml, protein level: 0.012 mg/ml, total amount of protein: 0.0096 mg). This fraction was used for the next step.

(6) Identification of Active Protein Band on the Electrophoretic Gel

Part of YMC-Pack PROTEIN RP active fractions as obtained in (5) was analyzed by electrophoresis. Electrophoresis was performed according to standard techniques (Laemmli, Nature, vol. 227, 680–685, 1970). 5.4 μl out of 0.8 ml of the active fractions was subjected to centrifugal evaporation, followed by the addition of 10 μl of sodium dodecyl sulfate (SDS) gel electrophoresis sample buffer with no reducing agent. Then the product was treated for 5 minutes at 95° C., subjected to SDS gel electrophoresis using 15–25% SDS-polyacrylamide precast gel (manufactured by Daiichi Pure Chemicals, Japan), and stained with 2D-silver staining reagent (Daiichi silver staining kit; manufactured by Daiichi Pure Chemicals, Japan). Daiichi III low molecular weight marker (manufactured by Daiichi Pure Chemicals, Japan) was used as a molecular weight marker. As a result, multiple bands were detected on the electrophoretic gel and the presence of multiple proteins in the active fractions was confirmed. To identify the active protein bands on the electrophoretic gel, an experiment was conducted to extract nerve regeneration-promoting activity from the electrophoretic gel. 8 μl out of 0.8 ml of the active fractions was subjected to centrifugal evaporation, followed by the addition of 10 μl of SDS gel electrophoresis sample buffer with no reducer. Then the product was treated for 10 minutes at 55° C., subjected to SDS gel electrophoresis using 15–25% SDS-polyacrylamide precast gel (manufactured by Daiichi Pure Chemicals, Japan). A prestained broad range marker (manufactured by New England Biolabs. Inc.) was used as a molecular weight marker. After electrophoresis, using a molecular weight of 16.5 KDa band of the pre-stained broad range marker as an index, a molecular weight region lower than 16.5 KDa band out of the regions to which samples had been added was cut into 14 rows of gel each having 1.6 mm width. The cut 14 rows of gel were separately added into an Eppendorf tube each containing 500 µl of purified water with 1.25 µg of transferrin, and then the tubes were set in a rotator and rotated at 4° C. After 16 hours, the extracts were collected. Then another 500 µl of purified water containing 1.25 µg of transferrin was added to the tube. After rotating for 4 hours at 4° C., the first and second extracts were mixed together to form a total of 1 ml of protein extract present in the gel. Subsequently, 20 µl of 1M potassium phosphate (pH 6.8) was added to each of the tubes to eliminate free SDS present in the extract, and then the mixture was allowed, to stand for 4 hours at 4° C. Further, the mixture was centrifuged at 10,000 rpm for 10 minutes to remove the precipitate, and the supernatant was collected, thereby obtaining protein extract present in the gel. After the extract was dialyzed against an assay medium, and subjected to DRG assay, nerve regeneration-promoting activity was detected in No.3 and No. 4 gel extracts corresponding to molecular weight of approximately 14500 Da. Thus it was found that the protein with molecular weight of approximately 14500 Da was an active protein.

Figure 2:
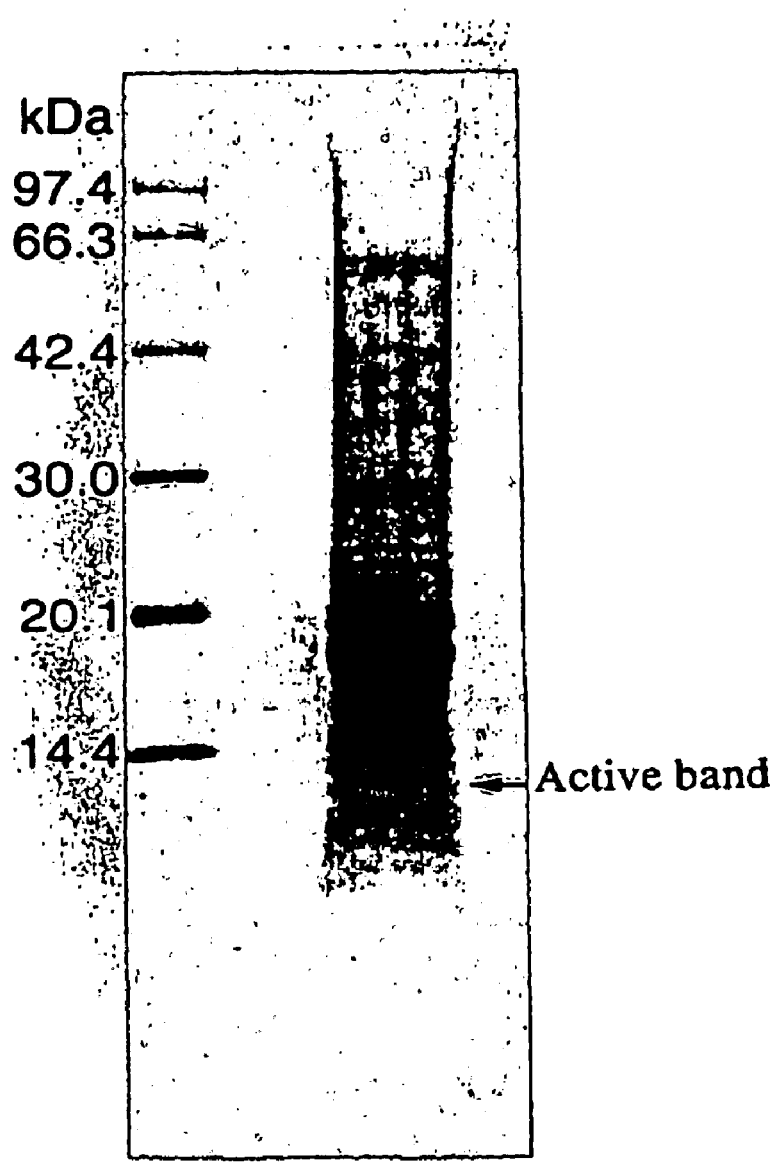
FIG. 2 is a photograph of an electrophoresis image of the nerve regeneration promoting factor purified from the culture supernatant of pRLF transfected COS1 cells.

(7) Separation by Electrophoresis and Electroblotting onto Polyvinylidene Difluoride (PVDF) Membrane The remainder of YMC-Pack PROTEIN RP active fractions were all separated by electrophoresis, because it was found that the active protein in YMC-Pack PROTEIN RP active fractions can be separated from other proteins by electrophoresis as described in (6). 786.6 µl of YMC-Pack PROTEIN RP active fraction was subjected to centrifugal evaporation, followed by addition of 30 µl of SDS gel electrophoresis sample buffer with no reducing agent. The product was treated for 5 minutes at 95° C., and subjected to SDS gel electrophoresis using 15–25% SDS-polyacrylamide precast gel (manufactured by Daiichi Pure Chemicals, Japan). Daiichi III low molecular weight marker (manufactured by Daiichi Pure Chemicals, Japan) and a pre-stained broad range marker (manufactured by New England Biolabs, Inc.) were used. After electrophoresis, using a semi dry transfer system (manufactured by Owl, Inc.), the product was transferred to PVDF membrane (manufactured by Perkin-Elmer Corporation; ProBlott) at a constant current of 150 mA for 3 hours. An anolyte consisting of 0.3 M Tris and 20% methanol (pH 10.4), a transfer membrane solution of 25 mM Tris and 20% methanol (pH 10.4), and a catholyte of 25 mM Tris and 40 mM aminocaproic acid and 20% methanol (pH 10.4) were used. The transferred membrane was stained with Coomassie brilliant blue (CBB) solution containing 0.1% CBB R-250 in 40% methanol and 1% acetic acid. When the stained product was destained with 50% methanol, a staining pattern equivalent to that of silver staining as described in (6) was detected. Moreover, a protein band with molecular weight of approximately 14500 Da, the activity itself, was also stained. Therefore, purification of nerve regeneration-promoting factor in the culture supernatant of pRLF-transfected COS 1 cell was completed. The obtained activity, amount of protein was assumed to be approximately 200 ng according to the degree of CBB staining (FIG. 2).

Example 8

Analysis of Partial Amino Acid Sequence of Nerve Regeneration-Promoting Factor

The amino acid sequence of the protein having nerve regeneration-promoting activity with a molecular weight of approximately 14500 Da that had been transferred to a PVDF membrane as obtained in Example 7 (7) was analyzed according to Iwamatsu's method (Iwamatsu et al., New Basic Biochemical Laboratory Procedures, Vol. 4, 33–84, Maruzen, Tokyo, Japan; Akihiro Iwamatsu, Seikagaku, Vol. 63, No. 2, 139–143, 1991, Japan; and Akihiro Iwamatsu, Electrophoresis, Vol. 13, 142–147, 1992).

(1) Reduction and S-carboxy Methylation

The CBB-stained protein band on a PVDF membrane, having nerve regeneration-promoting activity with a molecular weight of approximately 14500 Da, was cut out. Then the protein band was immersed in an Eppendorf tube with 100 PI of a reduction solution containing 1 mg of dithiothreitol (DI) [0.5 M Tris-HCl buffer (pH 8.3) containing 8M guanidine, 0.3% ethylenediaminetetraacetic acid (EDTA), and 0.125 M lysine] and allowed to stand for 1 hour at 60° C. Next 3 mg of monoiodoacetic acid was added to the solution, and then the solution was vigorously stirred for 15 minutes while shading the tube. After stirring, the PVDF membrane was washed in order with 2% acetonitrile and 0.1% SDS to remove excess reagent remaining on the membrane. Thus, the protein having nerve regeneration-promoting activity with a molecular weight of approximately 14500 Da, and reduced and S-carboxymethylated on the PVDF membrane, was obtained.

(2) Peptide Fragmentation, Peptide Mapping, and Amino Acid Sequence Analysis

Figure 3:
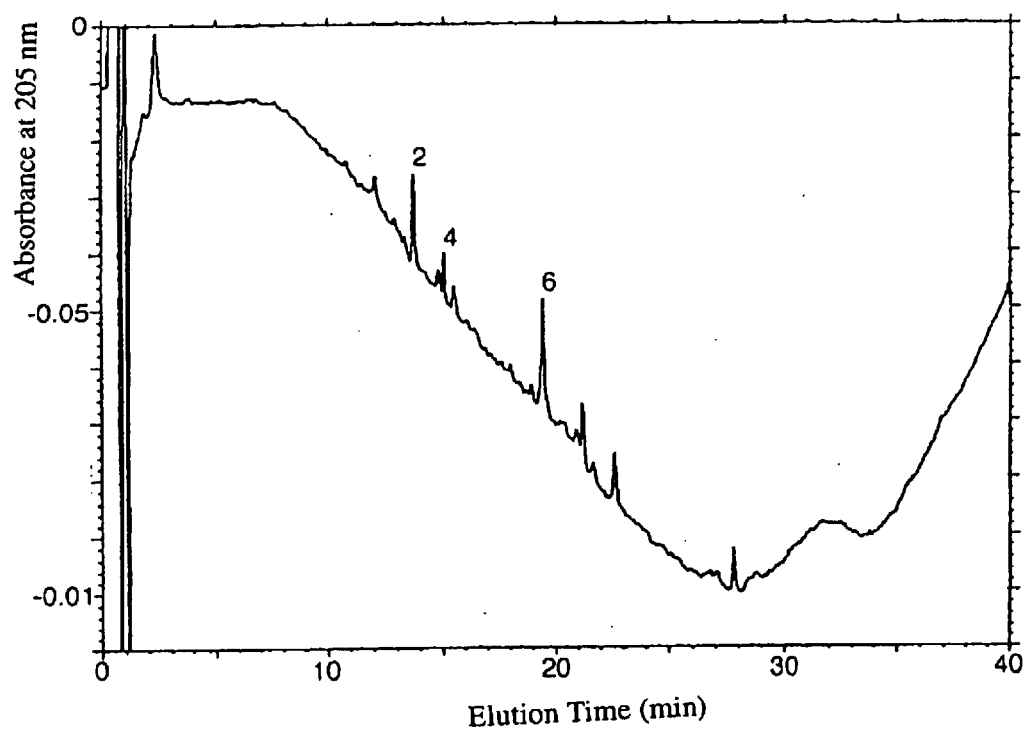
FIG. 3 is a peptide map determined by a reversed phase chromatography, after digesting the nerve regeneration promoting factor purified from the culture supernatant of pRLF transfected COS1 cells with lysyl endopeptidase.

To obtain multiple information on internal amino acid sequences from the resultant protein, the protein was fragmented into peptides by enzymatic digestion. Prior to this enzymatic digestion, PVDF membrane was immersed in 100 µl of 100 mM acetic acid containing 0.5% polyvinylpyrolidone (PVP)-40 and 1 mg of methionine, and then allowed to stand for 30 minutes at room temperature. Thus the unbound portion of protein on the membrane was blocked. After blocking, the membrane was washed with 10% acetonitrile to remove excess reagents. The washed membrane was transferred into a tube containing 20 mM Tris-HCl buffer (pH 9.0) with 10% acetonitrile, followed by addition of 5 pmol of lysyl endopeptidase (*Achromobacter* Protease I; manufactured by WAKO PURE CHEMICAL INDUSTRIES., LTD., Japan), allowing digestion to occur for 3 hours at 40° C. Thus peptide fragments digested by enzymes and liberated from the PVDF membrane were collected in a digestion buffer. The peptide fragments present in the digestion buffer were loaded to a Symmetry C18 reversed phase column (manufactured by Waters; φ 1.0 mm×50 mm) at a flow rate of 0.1 ml/min at 40° C. using 0.05% TFA as solvent A and isoparopanol:acetonitrile=7:3 with 0.02% TFA as solvent B, repectively. The column was eluted with a 30 minutes linear gradient from 1% B to 50% B, thereby obtaining fractions (FIG. 3). Each of the resultant peptide fragments was subjected to Edman degradation using a gas phase amino acid sequencer (manufactured by Shimadzu Corp., PPSQ-2). The N-terminal PTH amino acids recovered in sequence were identified by C18 reverse phase column chromatography based on the isocractic elution method. The amino acid sequences of the fragments that could be identified are summarized as follows (wherein amino acids are shown by one-letter notation):

AP2: PGECLRVRGEVA (SEQ ID NO:22);
AP4: LPDGYE (SEQ ID NO:23);
AP6: DSNNLCLHFN (SEQ ID NO:24).

A database was searched for these amino acid sequences. These sequences were identical to an amino acid sequence of human galectin-1 (Accession NO. P09382; SWISS-PROT database). Hence, it was concluded that the nerve regeneration-promoting factor in the culture supernatant of pRLF-transfected COS1 cells was the most likely to be monkey galectin-1.

Example 9
Cloning of Human Galectin-1 cDNA

First, PCR primers were synthesized based on GEN-BANK ACCESSION NO. J04456, corresponding to human galectin-1 cDNA. The sequences are as follows:

HLEG1: 5'-TGCGCCTGCCCGGGAACATC-3' (GENBANK ACCESSION NO. J04456, 15–34; SEQ ID NO:25);

HLEG2: 5'-GAACATCCTCCTGGACTCAA-3' (GENBANK ACCESSION NO. J04456, 2847; SEQ ID NO:26);

HLEG6: 5'-GCTGCCTTTATTGGGGGCCA-3' (the complementary strand to GENBANK ACCESSION NO. J04456, 472–491; SEQ ID NO:27);

HLEG8: 5'-GAGAGAGCGGCCGCATTGGGGGCCAT GGGCTGGC-3' (NotI site was added to 5' of the strand complementary to GENBANK ACCESSION NO. J04456, 463482; SEQ ID NO:28).

PCR was performed using 40 pmol each of the synthesized primers, HLEG1 and HLEG6, and using 2 µl of *E. coli* stock of SuperScript™ Human Liver cDNA Library (manufactured by GIBCO BRL) as a template. Using TaKaRa LA Taq (manufactured by Takara Shuzo Co., Ltd. Japan), PCR was performed in a volume of 100 µl using GeneAmp™ PCR System 2400 (manufactured by Perkin-Elmer Corporation). The PCR reaction cycle was repeated 35 times after denaturation for 5 minutes at 94° C., each cycle consisting of denaturation for 30 seconds at 94° C., annealing for 30 seconds at 60° C., and synthesis for 1 minute at 72° C.; followed by synthesis for further 5 minutes at 72° C. Further, PCR was performed using 40 pmol each of the synthesized primers, HLEG2 and HLEG8, and using 1 µl of the reaction solution under the same conditions except that annealing temperature was 55° C. The reaction solution was treated with phenol-chloroform (1:1), added with 3M NaOAc (1/10 of the total volume) and ethanol (twice the total volume), and then centrifuged, thereby obtaining pellet. The pellet was blunt-ended with T4 DNA polymerase (manufactured by Boehringer Manheim), digested with NotI, subjected to electrophoresis with 2% agarose gel, thereby recovering a fragment of approximately 460 bp as predicted. The fragment was purified using Prep-A-Gene DNA Purification Kit. Further the fragments was digested with EcoRI, blunt-ended with T4 DNA polymerase, then linked to pEF18S that had been digested with NotI. *E. coli* DH5 was used as a host cell. The insertion sequence of the obtained clone was amplified by PCR (wherein the reaction cycle was repeated 35 times after 5 minutes at 94° C., each cycle consisting of 30 seconds at 94° C./30 seconds at 50° C./1 minute at 72° C.) using 7 pmol each of the primers EF1α-1 (located outside EcoRI of the cloning site EcoRI-NotI of pEP18S, toward this cloning site; 5'-CCTCAGACAGTGGTTCAAAG-3'; SEQ ID NO: 29), and polyAC2 (located outside of NotI of the cloning site EcoRI-NotI of pEF18S, toward this cloning site; 5'-TGCATTCATTTTATGTTTCAG-3'; SEQ ID NO:30). Then the product was subjected to electrophoresis with 2% agarose gel. Thus the recovered fragment of approximately 500 bp as predicted was purified using Prep-A-Gene DNA Purification Kit. The nucleotide sequence of this fragment was analyzed by type377 DNA sequencer (manufactured by Perkin-Elmer Corporation) using primers, EF1α-1 and polyAC2, and using Taq Dye Deoxy™ Terminator Cycle Sequencing FS Kit (manufactured by Perkin-Elmer Corporation). Thus, a clone pEFGal1 (GENBANK ACCESSION NO. J04456, 50457) having the correct nucleotide sequence of human galectin-1 cDNA, from the initiation codon to the termination codon, was obtained.

Example 10
Confirmation of DRG Activity of COS1 Cell Expression Protein of Human Galectin-1 cDNA Clone pREFGal1 (referred to as COS1 expression Gal1 (1–134))

The plasmid pEFGal1 with human galectin-1 cDNA incorporated therein as obtained in Example 9 was transfected to a COS1 cell. Then the presence or absence of a nerve regeneration-promoting activity in Gal1 (1–134) that had been extracted from the COS1 culture supernatant and the COS1 cells were confirmed.

The clone pEFGal1 was cultured overnight in 100 ml of LB medium containing 50 µg/ml of Ampicillin and then subjected to centrifugation, thereby obtaining cells. Plasmid DNA was extracted from the resultant cells using QIAGEN Plasmid Maxi Kit (manufactured by QIAGEN). The plasmid pEFGal1 was transfected to COS1 cells using Transfectum reagent [manufactured by Promega KK; dioctadecylamidoglycylspermin (DOGS)]. $5 \times 10^6$ COS1 cells were inoculated on a plastic tissue culture flask with surface area 225 $cm^2$, and cultured overnight in an IMDM medium containing 10% FBS. After washing the culture cells with IMDM medium, 6.5 ml of IMDM medium was added. Further, 6.5 ml of IMDM medium containing 65 µg of the plasmid pEFGal1 and 6.5 ml of that containing 325 µg of a Transfectum reagent were mixed together and then added to the medium followed by culturing for 6 hours at 37° C. Next the culture solution was removed by suction, and. 52 ml of an IMDM medium containing 10% FBS was added to the flask, followed by 4 culturing for 2 days. After culturing, 50 ml of the culture supernatant and the cells were collected. The culture supernatant was dialyzed against 2 L of PBS containing 5 mM DTT overnight and then filtered. The collected cells were homogenized in 10 ml of PBS containing 100 mM lactose and 5 mM DTT. Then the product was centrifuged at 10000 G for 30 minutes at 4° C.; and the supernatant was collected, dialyzed overnight against 2 L of PBS containing 5 mM DTT, and filtered, thereby obtaining the cell extract. The resulting culture supernatant and cell extract were separately loaded at a flow rate of 0.25 ml/min to a lactose agarose column (manufactured by HONEN CORPORATION; φ5.0 mm×50 mm) that had been equilibrated with PBS containing 5 mM DTT, so that fractions that passed through the column were collected. Next, the eluting buffer was replaced by PBS containing 100 mM lactose and 5 mM DTT and adsorbed fractions were eluted. Electrophoretic analysis resulted in the detection of Gal1 (1–134) with a molecular weight of 14500 Da in adsorbed fractions for both the culture supernatant and the cell extract. The adsorbed fractions from the culture supernatant and the cell extract were dialyzed separately and thoroughly against an assay medium, and then subjected to DRG assay. Thus, a high nerve regeneration-promoting activity was detected at a concentration of 5–50 µg/ml that was estimated by the degree of gel staining. These results showed the presence of Gal1 (1–134) with high nerve regeneration-promoting activity, which was expressed in COS1 cells, in the culture supernatant and in the cells.

Example 11
Construction of *E. coli* Expression Vector for Gal1 (1–134)

Gal1 (1–134) was expressed using an *E. coli* expression vector, pET-3d (STRATAGENE), as described below. First, using pEFGal1 as a template and using two PCR primers, HLEG12, and HLEG14, PCR was performed for 25 cycles after 5 minutes at 94° C., each cycle consisting of 30 seconds at 94° C./30 seconds at 60° C./1 minute at 72° C. for synthesis; followed by 5 minutes at 72° C. for reaction. An amplified fragment containing a sequence spanning from the initiation codon to the termination codon of human galectin-1 was digested with NcoI and BamHI, and subjected to electrophoresis using 0.8% agarose gel, thereby yielding a fragment of approximately 420 bp. This fragment was purified using Prep-A-Gene DNA Purification Kit, and then linked to pET-3d that had been digested with NcoI and BamHI. *E. coli* DH5α was used as a host cell. A clone pETGal1 (1–134) having the correct nucleotide sequence of human galectin-1 cDNA (the nucleotide sequence ranging from NcoI to BamHI of the vector is shown in SEQ ID NO:7) was selected by analysis of the nucleotide sequence. The plasmid DNA of the clone was extracted using GFX™ Micro Plasmid Prep Kit (manufactured by Pharmacia Corporation), and then transformed into Epicurian Coli BL21 (DE3) Competent Cells (manufactured by STRATAGENE; having T7 polymerase downstream of lac UV5 of Lysogenic Lambda phage). The resultant *E. coli* transformant was used for expressing Gal1 (1–134). The PCR primers used herein are as follows:

HLEG12: 5'-AGAGTGGATCCTTATCAGTCAAAGGC CACACATTTG-3' (SEQ ID NO: 31; BamHI site was added at the 5' end of the complementary strand to GENBANK ACCESSION NO. J04456, 436–457);

HLEG14: 5'-GAGAGACCATGGCTTGTGGTCTG GTCGC-3' (SEQ ID NO:32; NcoI site was added at the 5' end of the complementary strand to GENBANK ACCESSION NO. J04456, 50–69).

Example 12

Purification of Gal1 (1–134) Expressed in *E. coli* and Confirmation of its Activity Gal1 (1–134) was obtained from the *E. coli* transformant, into which the *E. coli* expression plasmid pETGal1 (1–134) having human galectin-1 cDNA had been introduced. Then the presence or absence of nerve regeneration-promoting activity in Gal1 (1–134) was confirmed.

The transformant obtained in Example 11 was streaked onto the surface of an LB agar plate containing 50 μg/ml of ampicillin, cultured overnight at 37° C., allowing the colony formation. One of these colonies was shake-cultured in 50 ml of LB medium containing 50 μg/ml of ampicillin. The culture was added into 1000 ml of LB medium containing ampicillin at 50 μg/ml allowing the initial $OD_{600}$ to be 0.2, and then shake-cultured at 37° C. until the $OD_{600}$ reached 0.5–0.6. Subsequently, IPTG was added to the medium to a final concentration of 0.1 mM, followed by shake-culture for 3 hours, thereby inducing the expression of Gal1 (1–134).

One L of the cultured cell solution was centrifuged at 10000 G for 30 minutes, thereby obtaining a Gal1 (1–134) expressing bacterial pellet. The pellet was suspended in 20 ml of PBS, and then ultrasonicated with cooling. The suspension with disrupted cells was centrifuged at 10000 G for 30 minutes, and then the supernatant containing Gal1 (1–134) was collected as a soluble protein. The collected supernatant was dialyzed overnight against 2 L of 20 mM Tris-HCl buffer (pH 8.0). Then the dialysate was loaded at a flow rate of 2 ml/min at room temperature to a Shodex IEC DEAE-2025 column (manufactured by Showa Denko K.K., Japan; φ 2 cm×15 cm) equilibrated with 0% B using 20 mM Tris-HCl buffer (pH 8.0) as a solvent A and the same buffer containing 500 mM NaCl as a solvent B. After loading, the column was eluted in a 60 minutes linear gradient from 0% B to 30% B. The eluate was fractionated into 4 ml each, and then each fraction was subjected to electrophoretic analysis. A band that was suspected to be Gal1 (1–134) of a molecular weight of 14500 Da, was detected in a fraction with approximately 80 mM NaCl concentration. This fraction (15 ml) was used for the next step. Since the amino acid sequence of Gal1 (1–134) contains 6 cysteines, there is a high possibility that SS bonds were formed in human galectin-1 which was contained in the culture supernatant of pRLF-transfected COS1 cells and had a nerve regeneration-promoting activity. Hence, refolding of SS bonds was performed using copper sulfate as an oxidant. Gal1 (1–134) fraction (15 ml) from the DEAE column was diluted 20-fold with 20 mM Tris-HCl buffer (pH 8.0), and 1% copper sulfate solution was added to the diluted solution at the final concentration of 0.0001%. Then the solution was allowed to stand overnight at 4° C. 300 ml of the reaction solution was concentrated using a ultrafiltration unit (manufactured by Amicon; membrane YM 3 with 76 mm diameter), followed by buffer exchange using 20 mM sodium acetate (pH 5.0). Then the solution (final volume 50 ml) was loaded at a flow rate of 0.5 ml/min and at room temperature to a TSKgel SP-5PW column (manufactured by TOSOH CORPORATION, Japan; φ7.5 mm×75 mm) equilibrated with 0% B, using 20 mM sodium acetate buffer (pH 5.0) as a solvent A and the same buffer containing 500 mM NaCl as a solvent B. After loading, the column was eluted with a 60 minutes linear gradient from 0% B to 40% B. The eluate was fractionated into 1 ml each, and each fraction was subjected to electrophoretic analysis. A band that was suspected to be Gal1 (1–134) of a molecular weight of 14500 Da, was detected in a fraction with approximately 150 mM NaCl concentration. This fraction was used for the next step. Gal1 (1–134) fraction (8 ml) from the SP column was loaded at a flow rate of 2.0 ml/min and at room temperature to a YMC PROTEIN RP column (manufactured by YMC; φ 10 mm×250 mm) equilibrated with 40% B, using 0.1% TFA as a solvent A and 80% acetonitrile containing 0.1% TFA as a solvent B. After loading, the column was eluted with a 60 minutes linear gradient from 40% B to 50% B. The eluate was fractionated into 2 ml each, and each fraction was subjected to electrophoretic analysis. Two bands that were suspected to be Gal1 (1–134) having a molecular weight of 14500 Da, were detected respectively in two fractions, one with approximately 34% acetonitrile concentration and the other with approximately 36%. The two bands slightly differ in their mobility in electrophoresis with no reducing agent. However, their mobility was identical to each other in electrophoresis after reduction treatment Accordingly, it was inferred that the two bands were Gal1 (1–134) with different SS-bond bridges.

To confirm these bands were both Gal1 (1–134), N-terminal amino acid sequence analysis and amino acid composition analysis were performed using the fraction eluted at approximately 36% acetonitrile. First, N-terminal amino acid sequence analysis was performed using a protein sequencer (manufactured by Perkin-Elmer Corporation; type 492). As a result, the following N-terminal amino acid sequence was detected (wherein X is an undetermined amino acid):

AlaXGlyLeuValAlaSerAsnLeuAsnLeuLysProGly GluXLeuArgValArg (SEQ ID NO:33)

Since this sequence was identical to the N-terminal amino acid sequence of Gal1 (1–134), it was confirmed that the protein purified by PROTEIN RP column was Gal1 (1–134). Next, amino acid composition was analyzed after hydrolysis of acid using 6 N hydrochloric acid. A sample was subjected to acid hydrolysis in vapor phase with 6 N hydrochloric acid using a PICO•TAG workstation (manufactured by Waters Corporation) for 1 hour at 150° C. Then the sample was subjected to fluorescent derivatization reaction using an AccQ Fluor reagent (manufactured by Waters Corporation). The amino acids were analyzed using an AccQ Tag amino acid analysis system (manufactured by Waters Corporation), and the following amino acid composition ratio was detected. Theoretical values for Gal1 (1–134) are shown in parenthesis:

Asp:22.18 (22), Ser:5.51 (5), Glu:10.30 (10), Gly:11.38 (11), His:2.12 (2), Arg:5.10 (5), Thr:3.89 (4), Ala:13.90 (14), Pro:7.09 (7), Tyr:2.08 (2), Val:9.23 (10), Met:1.15 (1), Lys:7.97 (8), Ile:3.29 (4), Leu:11.85 (12), Phe:9.96 (10) (Cys, and Trp were not determined).

Therefore, it was confirmed that the amino acid composition ratio of the purified protein was in good agreement with the theoretical values of Gal1 (1–134). It was confirmed that the purified protein was Gal1 (1–134), and the purity was significantly high.

Figure 4:
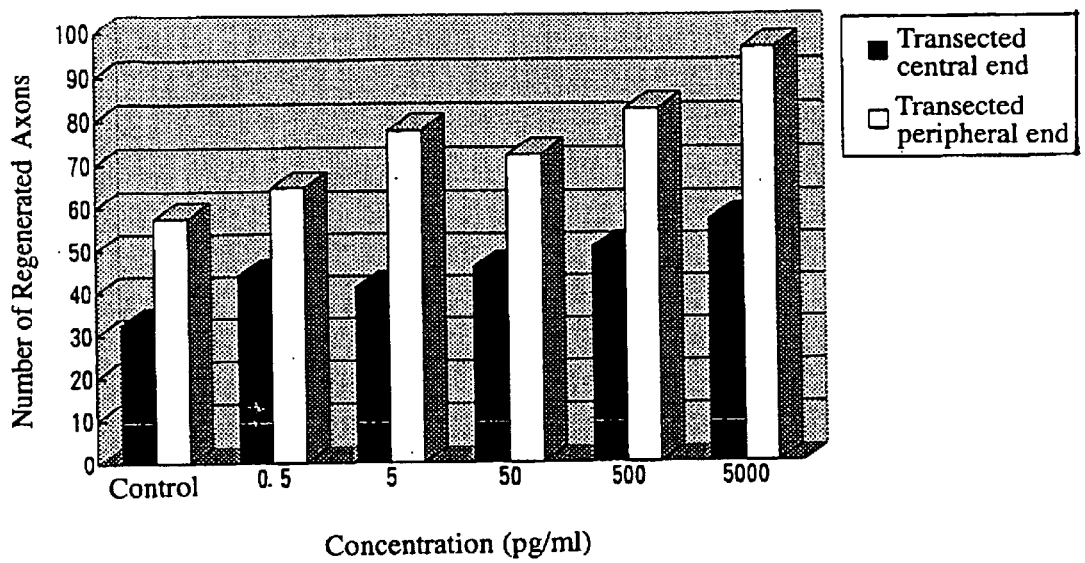
FIG. 4 shows the results regarding the nerve regeneration promoting activity of an *Escherichia coli* expression product Gal1 (1–134). Herein, "Transected central end" and "Transected peripheral end" refer to "a transected central nerve end" and "a peripheral nerve end", respectively.
Figure 4:
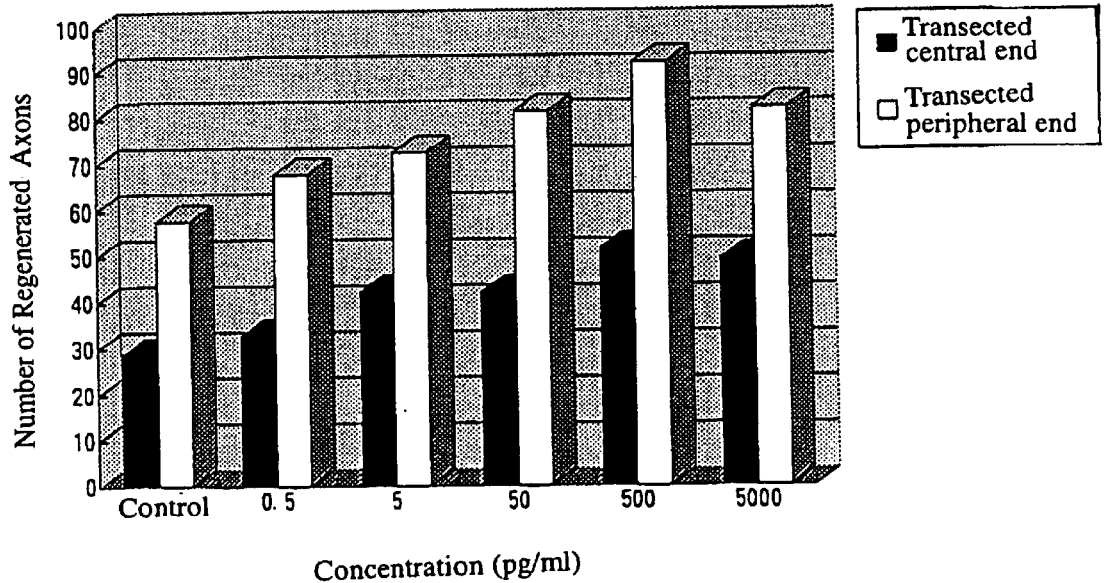

Similarly, N-terminal amino acid sequence analysis and the amino acid composition analysis were conducted for the fraction eluted at approximately 34% acetonitrile. As a result, it was confirmed that the protein eluted in this fraction was Gal1 (1–134) in each analysis. Subsequently, the concentration of Gal1 (1–134) in each sample was determined from the results of the amino acid analysis. The fractions were adjusted to 0.5, 5, 50, 500, 5000 µg/ml, respectively, with an assay medium, and then the nerve regeneration-promoting activity was measured by DRG assay. As a result, Gal 1(1–134) showed a nerve regeneration-promoting activity at the concentration from 0.5 µg/ml to 500 µg/ml, depending on the concentration (FIG. 4). Hence, it was confirmed that *E. coli*-expressed Gal1 (1–134) in which intramolecular SS bonds were formed via oxidation process with copper sulfate possessed a nerve regeneration-promoting activity.

Example 13
Identification of the Pattern of Disulfide Linkages Form of *E. coli* Expressed Gal1 (1–134)

The pattern of disulfide linkages of *E. coli* Gal1 (1–134) obtained in Example 12 (the fraction eluted at an approximately 36% acetonitrile) was identified by mass spectrometry of peptide fragments after enzymatic digestion. 50 µl of the *E. coli* expressed Gal1 (1–134) fraction (equivalent to 15 µg as determined by amino acid analysis) was subjected to centrifugal evaporation, dissolved in 20 µl of 100 mM Tris-HCl buffer (pH 6.8), and then digested with 0.6 µg of trypsin for 16 hours at 37° C.

Figure 5:
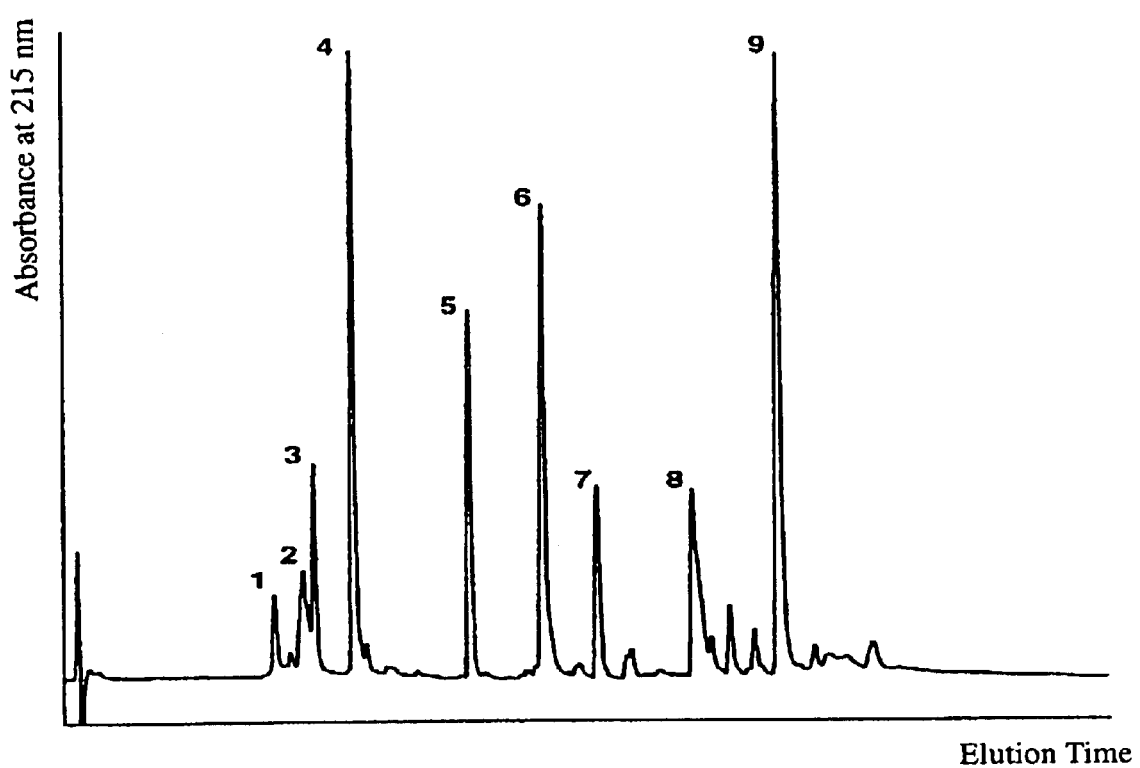
FIG. 5 is a peptide map separated by a reversed phase chromatography, after digesting an *Escherichia coli* expression product Gal1 (1–134) with trypsin.

The peptide fragments present in the digestion buffer were loaded to a Symmetry C18 reverse phase column (manufactured by Waters Corporation; φ 2.0 mm×50 mm) at a flow rate of 0.25 ml/min at a column temperature of 40° C. using 0.05% TFA as a solvent A and a mixture of isoparopanol:acetonitrile=7:3 with 0.02% TFA as a solvent B. The column was eluted with a 50 minutes linear gradient from 1% B to 50% B, to collect the fragments by fractionation (FIG. 5). Part (0.5 µl) of each resultant peptide fragment solution was spotted on a sample plate, and mixed with 0.5 µl of α-cyano-4-hydroxycinnamic acid (CHCA) that had been dissolved at 10 mg/ml in a solution of acetonitrile:0.1% TFA=50:50, followed by air-drying. The dried product was subjected to mass spectrometry using a mass spectrometer, Matrix-Assisted Laser Desorption Ionization ime-of-Flight (MALDI-TOF) type (manufactured by Perceptive; Voyager Elite). Fragment Nos, detected mass, and amino acid sequences assigned based on the mass are as shown below:

| | | |
|---|---|---|
| TP1 | 786.429 | $G^{21}EVAPDAK^{28}$ (SEQ ID NO:34); |
| TP2 | 534.028 | $F^{108}PNR^{111}$ (SEQ ID NO:35); |
| TP3 | 1042.15 | $V^{19}RGEVAPDAK^{28}$ (SEQ ID NO:36); |
| TP4 | 1077.29 | $D^{64}GGAWGTEQR^{73}$ (SEQ ID NO:37); |
| TP5 | 969.466 | $L^{100}PDGYEFK^{107}$ (SEQ ID NO:38); |
| TP6 | 3021.11 | $D^{37}SNNLC^{42}LHFNPR^{48}$ (SEQ ID NO: 39) + $F^{49}NAHGDANTIVC^{60}NSK^{63}$ (SEQ ID NO:40); |
| TP7 | 878.451 | $S^{29}FVLNLGK^{36}$ (SEQ ID NO:41); |
| TP8 | 1785.14 | $L^{112}NLEAINYMAADGDFK^{127}$ (SEQ ID NO:42) |
| TP9 | 5222.08 | $A^{1}C^{2}GLVASNLNLKPGEC^{16}LR^{18}$ (SEQ ID NO:43) + $E^{74}AVFPFQPGSVAEVC^{88}ITFDQANLTVK^{99}$ (SEQ ID NO:44); + $C^{130}VAFD^{134}$ (SEQ ID NO:45). |

Figure 6:
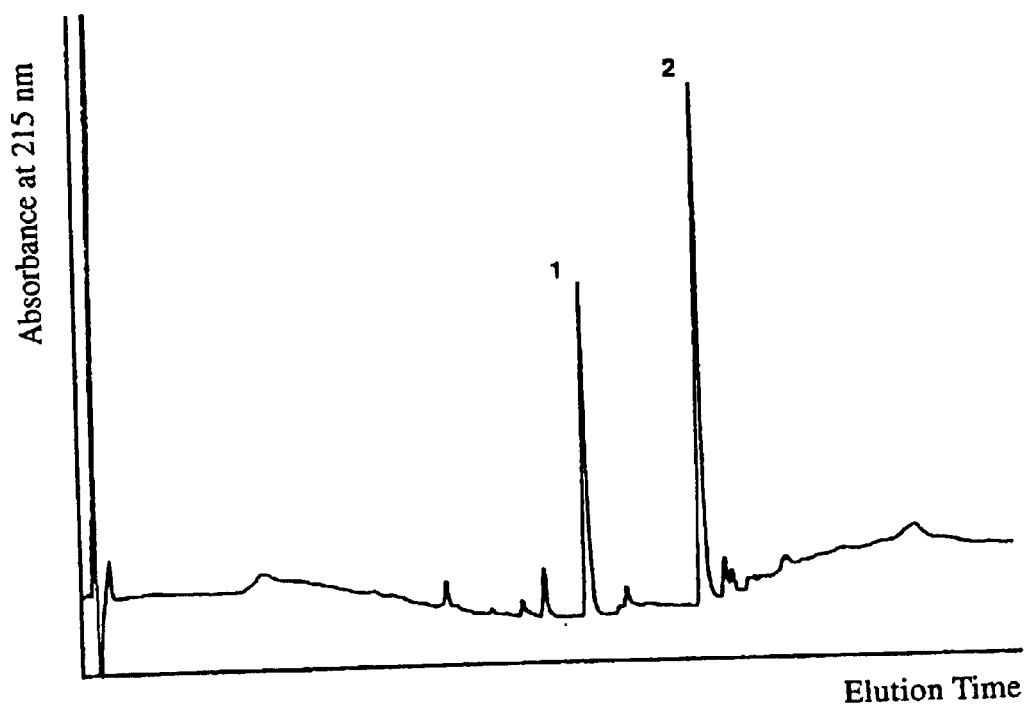
FIG. 6 is a peptide map separated by a reversed phase chromatography, after the secondary digesting TP9, the tryptic digestion fragment of an *Escherichia coli* expression product Gal1(–134), with lysyl endopeptidase.

These results revealed that *E. coli* expressed Gal1 (1–134) (the fraction eluted at approximately 36% acetonitrile) had three sets of SS-bond bridges. One of them was Cys42–Cys60, and Cys88 and Cys130 were linked with either Cys2 or Cys 16. To identify the pattern of disulfide linkages of the remaining two sets, secondary digestion was performed by adding lysil-endopeptidase (manufactured by WAKO PURE CHEMICAL INDUSTRIES., LTD., Japan) to TP9. TP9 was subjected to centrifugal evaporation, to which 20 pmol of lysil-endopeptidase (manufactured by WAKO PURE CHEMICAL INDUSTRIES., LTD., Japan) was added, and then digested for 16 hours at 37° C. in 20 µl of 100 mM Tris-HCl buffer (pH 6.8). The peptide fragments present in the digestion buffer were loaded to a Symmetry C18 reverse phase column (manufactured by Waters Corporation; φ 2.0 mm×50 mm) at a flow rate of 0.25 ml/min at a column temperature of 40° C., using 0.05% TFA as a solvent A and a mixture of isoparopanol:acetonitrile=7:3 with 0.02% TFA as a solvent B. The column was eluted with a 30 minutes linear gradient from 1% B to 50% B to collect the fragments by fractionation (FIG. 6). After centrifugal evaporation, the resultant peptide fragments were subjected to mass spectrometry using a mass spectrometer, type MALDI-TOF (manufactured by Perceptive; Voyager Elite). Fragment Nos, detected mass, and amino acid sequences assigned based on the mass are as shown below:

| | | |
|---|---|---|
| TPAP1 | 1755.31 | $A^{1}C^{2}GLVASNLNLK^{12}$ (SEQ ID NO:46) + $C^{130}VAFD^{134}$ (SEQ ID NO: 47); |
| TPAP2 | 3484.21 | $P^{13}GEC^{16}LR^{18}$ (SEQ ID NO:48) + $E^{74}AVFPFQPGSVAEVC^{88}ITFDQANLTVK^{99}$ (SEQ ID NO:49). |

It was thus identified that the pattern of disulfide linkages of the remaining two sets were Cys2–Cys130 and Cys16–Cys 88. As a result, it was found that *E. coli* expressed Gal1 (1–134) (the fraction eluted at approximately 36% acetonitrile) had three sets of SS bonds and the pattern of disulfide linkages was Cys42–Cys60, Cys2–Cys130, and Cys16–Cys 88.

Similarly, the pattern of disulfide linkages was identified for *E. coli* expressed Gal1 (1–134) that had been eluted at approximately 34% acetonitrile. The SS-linkage form was a mixture of the form: Cys2–Cys42, Cys16–Cys88, and Cys60–Cys130 and the form: Cys2–Cys60, Cys16–Cys88 and Cys42–Cys130.

Example 14
Measurement of Lectin Activity of *E. coli* Expressed Gal1 (1–134)

Galectin belongs to a protein family, generally called animal lectin, and binds to sugars containing P-galactoside. To determin if the *E. coli* expressed Gal1 (1–134) possesses a lectin activity (a β-galactoside binding activity), two methods, i.e. an affinity chromatography using β-galactoside as a ligand and a hemagglutination assay, were conducted.

(1) Affinity Chromatography Using β-Galactosid as a Ligand

The E. coli expressed Gal1 (1–134) was loaded at a flow rate of 0.5 ml/min and at 4° C. to a lactose agarose column (manufactured by HONEN CORPORATION; φ 5.0 mm×50 mm) that had been equilibrated with 0% B, using PBS as a solvent A and PBS containing 0.1 M lactose as a solvent B. After loading, the column was eluted with a 30 minutes linear gradient from 0% B to 100% B. The eluate was fractionated into 2 ml each, and separately analyzed by electrophoresis. As a result, Gal1 (1–134) with a molecular weight of 14500 Da was detected in flow-through fractions. In addition the same sample was subjected to a reduction treatment with 5 mM DTT for 2 hours at room temperature, and applied to the same lactose agarose column. In this time, Gal1 (1–134) was not detected in flow-through fractions, but in fractions having about 10 mM lactose. These results confirmed that the E. coli expressed Gal1 (1–134) could not bind to β-galactoside (lactose), but the β-galactoside binding activity is restored by reduction treatment.

Figure 7:
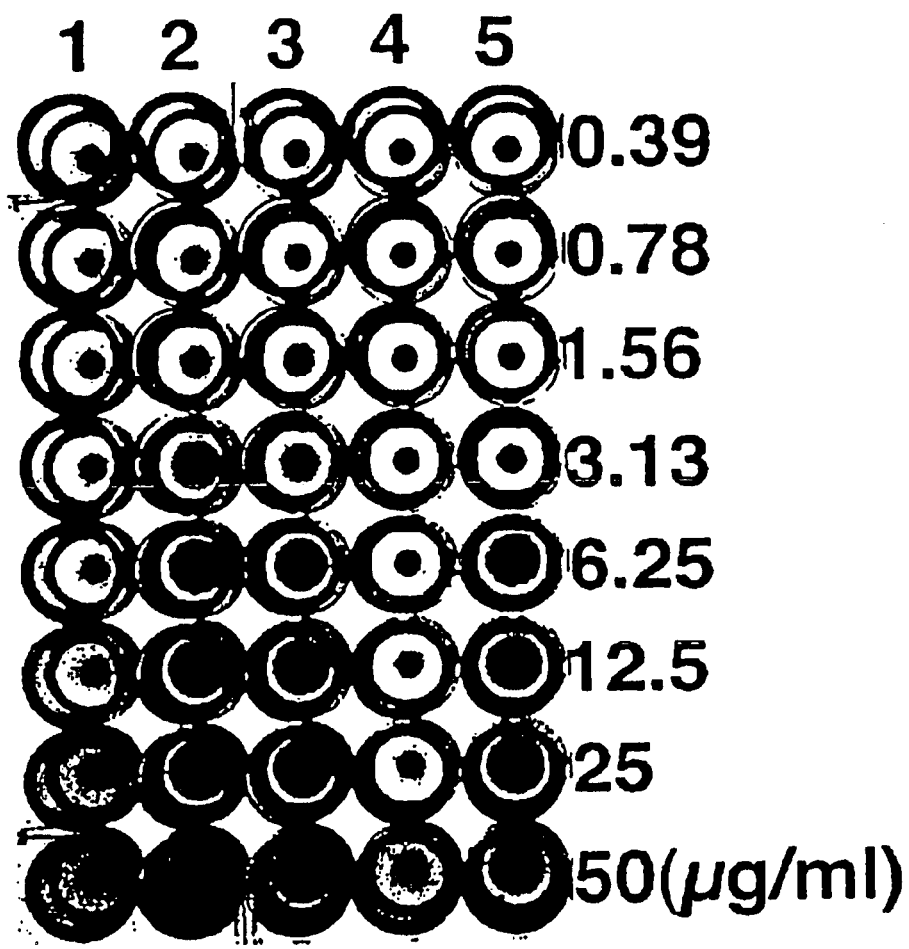
FIG. 7 shows the results of examining hemagglutination activity of an *Escherichia coli* expression product Gal1 (1–134).

(2) Measurement of Hemagglutination Activity 5 ml of PBS was added to 1 ml of stored rabbit blood (manufactured by Cosmo Bio), followed by centrifugation at 2000 G for 5 minutes, thereby removing the supernatant. This procedure was repeated 3 times to obtain an erythrocyte fraction. Then 4.9 ml of PBS was added to 100 μl of the erythrocyte fractions so as to prepare 2% blood cell suspension. 50 μl of E. coli expressed human galectin-1 (diluted 50 μg/ml with PBS) obtained in Example 12 was added to the first row of a 96-well titer plate; and 50 μl each of the same galectin-1 2-fold diluted (at maximum 0.39 μg/ml), was added to the second and the following rows. Then 50 μl each of 2% blood cell suspension was dispensed into each well, and allowed to stand for 1 hour at room temperature. At this time, the same dilution series were prepared for Concanavalin A and for E. coli expressed Gal1 (1–134) that had been subjected to a reduction treatment with concanavalin A and 5 mM DTT for 2 hours at room temperature, and simultaneously the hemagglutination activity was measured. As a result, hemagglutination activity was detected at a concentration of 6.25 μg/ml or more for Concanavalin A and for any of E. coli expressed Gal1 (1–134) that had been subjected to reduction treatment with 5 mM DTT for 2 hours at room temperature. However, for E. coli expressed Gal1 (1–134) (not reduced) obtained in Example 12, no hemagglutination activity was detected even at a concentration of 50 μg/ml (FIG. 7).

As a result of both the affinity chromatography using β-galactoside as a ligand and the measurement of hemagglutination activity, it was confirmed that Gal1 (1–134) having SS bonds, as prepared in Example 12, possessed no lectin activity.

Example 15

Preparation and Purification of Anti-Gal1 (1–134) Antiserum

A rabbit was immunized with E. coli expression Gal1 (1–134) as an antigen to obtain a rabbit anti-Gal1 (1–134) antiserum. The E. coli expression Gal1 (1–134) as the antigen was purified by a TSKgel SP-5PW column (manufactured by TOSOH CORPORATION) as described in Example 12. Two rabbits were immunized. After emulsion was prepared using Gal1 (1–134) and oil adjuvant, it was administered subcutaneously to a rabbit in a dose of 20–200 μg, 6 times in total over approximately 2 months.

After immunization, exsanguination was performed, thereby obtaining a serum of approximately 75 ml per rabbit. Then titration was conducted by ELISA using plates with antigens immobilized thereon. The obtained antiserum showed a significant value even if it was diluted 1: 204800 at the maximum. That is, a highly specific and good antiserum was obtained.

The resulting antiserum was purified using a protein A column, and immunoglobulin (IgG) fractions were prepared. 10 ml of the antiserum was diluted 2-fold with 10 ml of PBS, filtered, then applied to a HiTrap Protein A column (manufactured by Pharmacia; 1 ml gel) equilibrated with PBS. After washing with 20 ml of PBS, adsorbed fractions were eluted using 5 ml of 100 mM glycine-HCl buffer (pH 2.7). At this time, to the fraction tubes, 500 μl of 1 M Tris-HCl buffer (pH 9.0) was previously added. Plow-through fractions, as well as adsorbed fractions, were analyzed by electrophoresis. Only IgG was detected in the adsorbed fractions. Since the flow-through fractions also contained IgG, they were purified again in the same way as described above. When the purified product was analyzed by electrophoresis, second flow-through fractions also contained IgG. The second fractions were similarly re-purified. The adsorbed fractions from three purification runs were combined (16.5 ml), and were dialyzed against 2 L of PBS overnight, thereby obtaining approximately 30 mg of anti-Gal1 (1–134) IgG (as a protein concentration determined by Coomassie dye binding method).

Example 16

Preparation of Anti-Gal1 (1–134) IgG Column

Anti-Gal1 (1–134) IgG column was prepared by immobilizing anti-Gal1 (1–134) IgG obtained in Example 15 to a resin. 5 ml of a solution of 2 mg/ml anti-Gal1 (1–134) IgG was concentrated using a ultrafiltration membrane (10,000 cut-off, MILLIPORE), and simultaneously buffer exchange was performed with 1 ml of a coupling buffer (0.2 M sodium bicarbonate, 0.5 M sodium chloride, pH 8.3). A HiTrap NHS-activated column (manufactured by Pharmacia; 1 ml gel) was washed with 6 ml of 1 mM hydrochloric acid, and then to which 1 ml of the above IgG solution was added, allowing to stand for 30 minutes at room temperature. Subsequently, the column was washed with 3 ml of the same coupling buffer, and washed with 6 ml each of a washing buffer A (0.5 M ethanol amine, 0.5 M sodium chloride, pH 8.3) and a washing buffer B (0.1 M sodium acetate, 0.5 M sodium chloride, pH 4.0). Further, 6 ml of the washing buffer A was loaded to the column, and then allowed to stand for 30 minutes at room temperature. The column was washed with 6 ml each of washing buffer B, washing buffer A, washing buffer B, and PBS, in order, so that anti-Gal1 (1–134) IgG column was prepared.

Example 17

Purification of COS1 Cell Expressed Gal1 (1–134) and Identification of the Pattern of Disulfide Linkages To determine the pattern of SS linkages of Gal1 (1–134) expressed in COS1 cells and secreted in culture supernatant, Gal1 (1–134) was purified from the culture supernatant of COS 1 cells by a purification technique not employing a lactose agarose column after reduction treatment as described in Example 10. Plasmid pEFGal1 having human galectin-1 cDNA as described in Example 9 was transfected in the same manner as described in Example 7, and 250 ml of the culture supernatant was obtained. The culture supernatant was added at a flow rate of 0.5 ml/ml and at 4° C. to the anti-Gal1 (1–134) IgG column obtained in Example 16 that had been equilibrated with PBS, using a Peristaltic pump (manufactured by Pharmacia; type P-1). The column was washed with 50 ml of PBS, and then adsorbed fractions were eluted with 3 ml of 100 mM glycine-HCl buffer (pH 2.7). To the fraction tubes, 300 μl of 1M Tris-HCl buffer (pH 9.0) was previously added. When the adsorbed fraction was analyzed by electrophoresis, a band suspected to be Gal1 (1–134) with a molecular weight of 14500 Da was detected. 3.3 ml of this fraction was used for the next step. Using 0.1% TFA as a solvent A, and 80% acetonitrile containing 0.1% TFA as a solvent B, the anti-Gal1 (1–134) IgG column adsorbed fraction was loaded at a flow rate of 0.5 ml/min at room temperature to a YMC PROTEIN RP column (manufactured by YMC; φ 4.6 mm×150 mm) equilibrated with 40% B. After loading, the column was eluted with a 45 minutes linear gradient from 40% B to 55% B. The eluate was fractionated into 0.5 ml each, and then each fraction was analyzed by electrophoresis. Thus only the band suspected to be Gal1 (1–134) with a molecular weight of 14500 Da was detected in the fraction (Fr35) having approximately 38% acetonitrile. 0.5 μl of this fraction was subjected to mass spectrometry using a MALDI-TOF mass spectrometer (manufactured by Perceptive; voyager Elite) in the same manner as described in Example 13.

As a result, the molecular mass of this band was 14622.1 Da. Compared to the molecular mass of 14583.4 Da of Gal1 (1–134) being in the reduced state, it was found that this band corresponded to Gal1 (1–134) wherein the N-terminus was acetylated and SS bonds were formed. Thus, the purification of Gal1 (1–134) expressed in COS1 cells and secreted in the culture supernatant was completed.

Because it was predicted from the results of mass spectrometry that Gal1 (1–134) secreted in the culture supernatant carries is linked by SS bonds, the patterns of disulfide linkages were identified. Briefly, the Gal1 (1–134) was digested with trypsin and lysyl-endopeptidase according to the methods described in Example 13. The resulting fragments were subjected to mass spectrometry, and each fragment was assigned. It was found that the pattern of SS linkages form of Gal1 (1–134) secreted in the culture supernatant was Cys42–Cys60, Cys2–Cys130, and Cys16–Cys88. This pattern was identical to that of *E. coli* expressed Gal1 (1–134) (the fraction eluted at approximately 36% acetonitrile) as described in Example 13.

Example 18
Sciatic Nerve Injury Model Experiment

Under chloral hydrate anesthesia, sciatic nerves of an adult BALB/c mouse (female, 3–6 weeks old) were exposed at the femoral region and transected. The transected nerve site, at 7 mm from the transected central side end, was injured with forceps. An osmotic minipump (Alzet, model 2002 for 2 weeks, or model 2001 for 1 week) was placed at a subcutaneous position of the murine back, and then the transected central side end of the sciatic nerve was inserted into a polyethylene tube connected to a pump. The mini pump was previously filled with 220 μl a solution of 5 μg/ml Gal1 (1–134) in physiological saline. This Gal1 solution was continuously sent into the transected nerve end at 1.0 or 0.5 μl/h over 14 days or 7 days. For the 14 days model, the region of from the injured site to the transected nerve end was further injured by freezing. On day 7 and on day 14 after injury, the injured sciatic nerve was fixed by perfusion with 4% paraformaldehyde, removed, and then subjected to 2.5% glutaraldehyde fixation. After osmium fixation, the nerve was epon-embedded, sectioned into an ultra-thin section, and then observed it with an electron microscope. A site, at 6 mm away from the injured site and 1 mm from the transected central side end (i.e., the site administered with the solution), was observed with an electron microscope.

Figure 8:
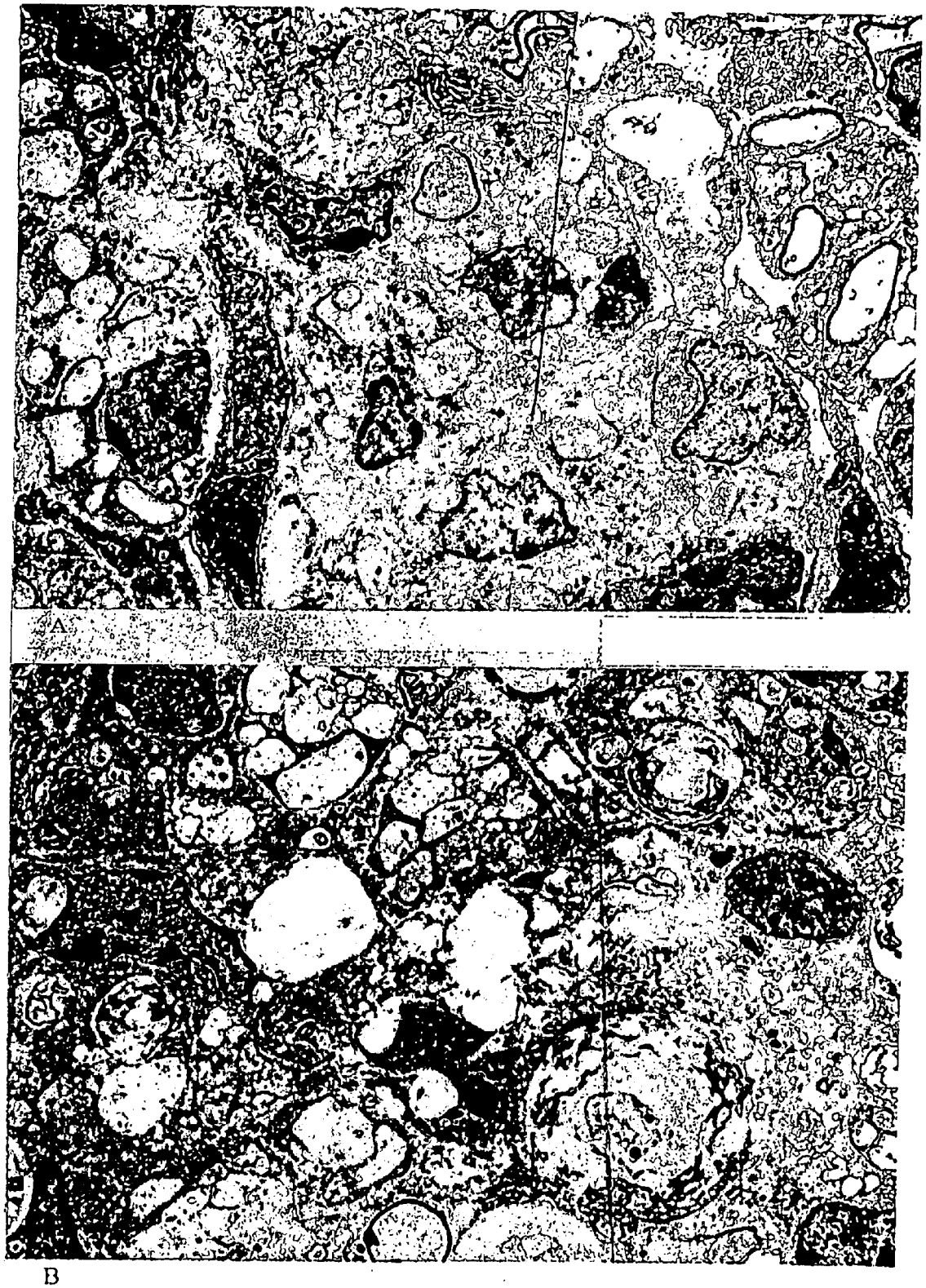
FIG. 8 is two electron micrographs showing a peripheral site positioned at 6 mm from the crush lesion site into which Gal1 (1–134) (A) and a control (B) were respectively administered for 14 consecutive days.

On day 7, for Gal1 (1–134) administered groups, there were observed tendencies of the increase in myelin phagocytes and of the increase in regenerating axons that was thought of an initial regeneration process of medullary sheath, compared to control, suggesting early disruption of myelin and progression of nerve regeneration. On day 14, for control groups, many degenerative myelin remained and regenerating myelinated nerves were hardly observed (FIG. 8B). On the other hand, for Gal1 (1–134) administered groups, a decrease was observed both in myelin phagocytes and in degenerative myelin, and regeneration of lots of thinly myelinated nerves between regenerated nonmedullary nerve bundles was observed (FIG. 8A). These findings suggest that Gal1 (1–134) administration results in promoted regeneration of injured nerves.

Example 19
Preparation of Collagen Gel Silicon Chamber for Regeneration Experiment of Transected Peripheral Nerve and Regeneration Experiment of Transected Peripheral Nerve One end of a sterilized silicon tube (outer diameter 1.5 mm, inner diameter 1 mm, and length 7 mm) was closed with a sterilized glass bead. 0.8 ml of collagen solution (0.3%) was extracted from a rat tail at 0° C. and dissolved in 0.1% acetic acid, followed by sequential addition of 10 μl of Gal1 (1–134) at 500 ng/ml, 0.1 ml of 10×NEM (GIBCO, Minimum Essential Medium), and 0.1 ml of a pH adjusting solution (0.477 g Hepes dissolved in 10 ml 0.3 N NaOH). Similarly, a Gal1 (1–134)-free control collagen solution was prepared. Silicon tubes were filled on ice with each collagen solution, and collagen solutions were converted to a gel phase by warming at 37° C., thereby preparing collagen gel silicon chambers.

A 10–11 weeks old male Wister rat was anesthetized with pentobarbital (0.3 ml, 50 mg/ml). Then the femoral region was incised to expose the sciatic nerve and the nerve was separated into fibular nerve and tibial nerve. Collagen gel silicon chambers containing Gal1 (1–134) and control collagen gel silicon chambers were prepared. The Gal1 (1–134)-containing chamber was arranged in parallel to the left fibular nerve, with their opening in proximity to the left fibular nerve, and the both ends were fixed to the muscle with stitches. Next the fibular nerve was transected, the transected proximal nerve ending was put in the silicon tube, and then the nerve fibers were fixed to the tube with stitches. The incised site was sutured. Similarly, the right fibular nerve was transected, and the control chamber was fixed thereto. Gal1 (1–134)-containing chamber and control chamber were fixed, while alternating the sides (left and right) per rat. 7 and 10 days after rearing, the rat was anesthetized with Pentobarbital, and then fixed by perfusion with a zamboni fixation solution. Then the transplanted chamber was removed. Tubes were fixed with 4% paraformaldehyde, and then longitudinal or cross-frozen sections were generated in a cryostat. Next, immunostaining was performed using hematoxylin-eosin (HE) staining and anti-neurofilament (NF) antibody, and anti-S 100 antibody. Based on images of immuno-staining of longitudinal sections with HE and with anti-S100 antibody and anti-NF antibody, a migration distance from the transected nerve end in the silicon tube to S100 positive Schwann cells, and an elongation distance of NF positive regenerated-axons, were measured. The number of NF positive regenerated-axons was counted from cross sections.

Figure 9:
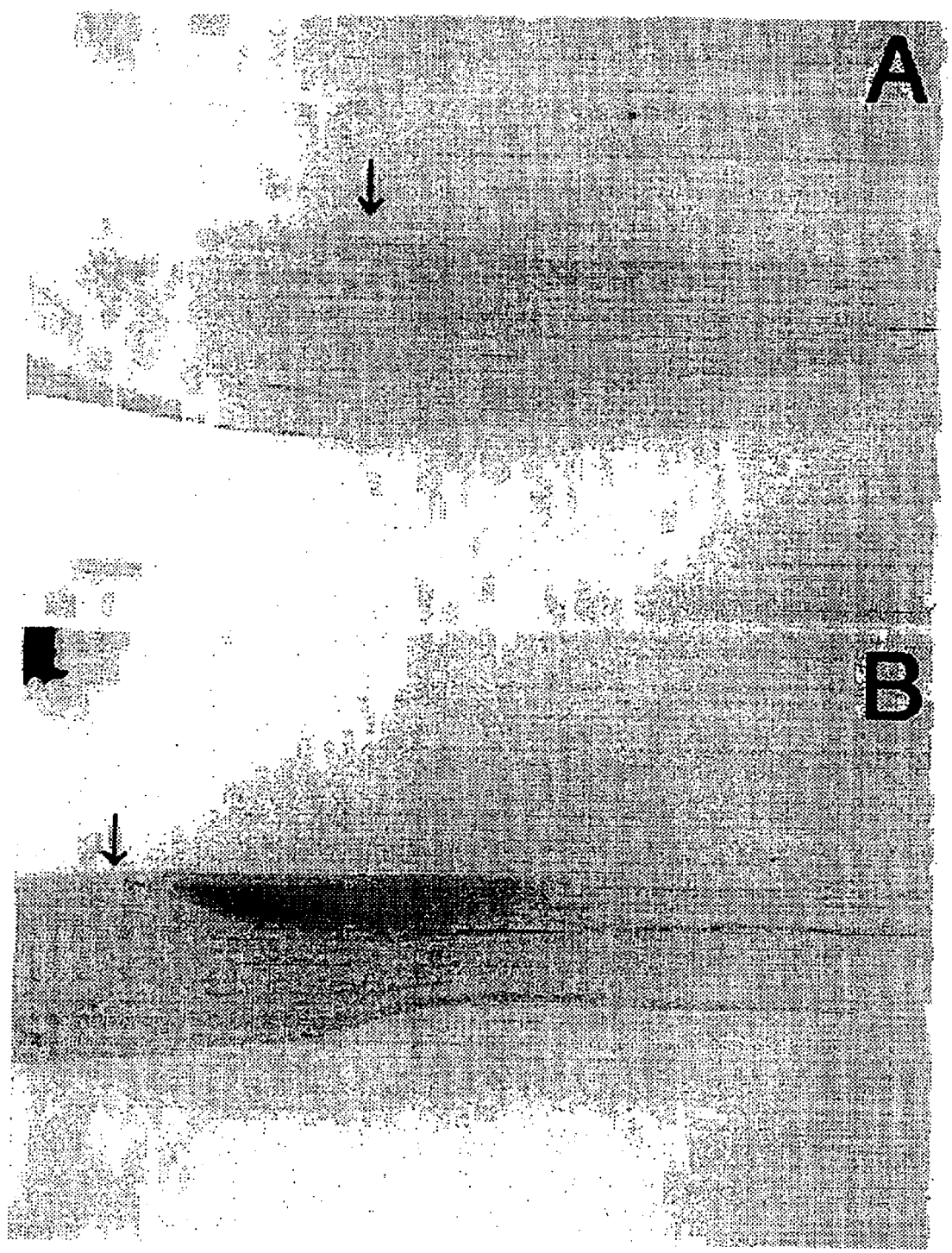
FIG. 9 is two photographs showing HE-stained images of longitudinal frozen nerve sections from rat, which were subjected to a perfusion-fixation 10 days after operation of administering Gal1 (1–134) (A) and a control (B) respectively.
Figure 10:
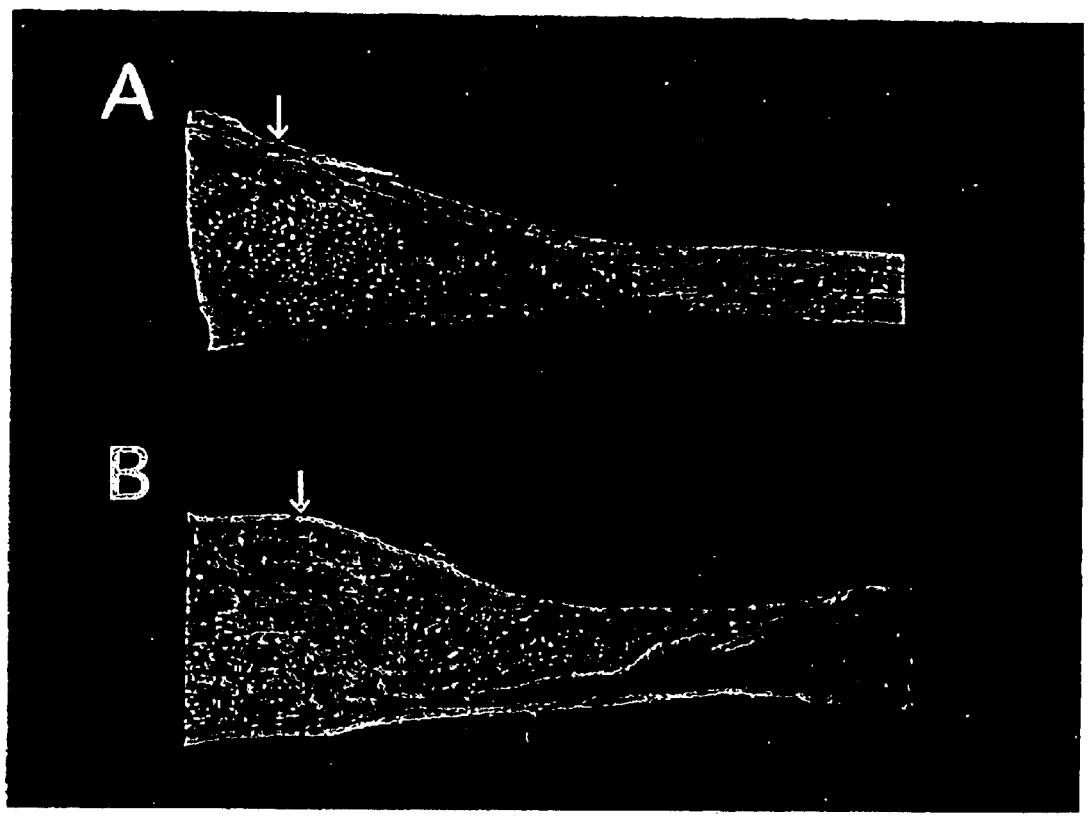
FIG. 10 is two photographs showing immuno-stained images with an anti-NF antibody of longitudinal frozen sections from rat, which were subjected to a perfusion-fixation 10 days after operation of administering Gal1 (1–134) (A) and a control (B) respectively.

Based on the results of HE staining, the migration distance of cells migrated from the transected nerve end into the gel was measured. As shown in FIG. 9, the presence of Gal1 (1–134) resulted in the increase in migration distance of migrating cells when compared to the control. Specifically, as shown in Table 1, on day 7 after treatment, the average migration distance of the control was 0.7 mm while that of the Gal1 (1–134)-administered group was 1.1 mm; on day 10, that of the control was 1.2 mm while that of Gal1 (1–134)-administered group was 1.9 mm. That is, administration of Gal1 (1–134) promoted migration of cells. S100 positive Schwann cell, a major migrating cell, reached the tip of the regeneration site. Further, as shown in FIG. 10, NF positive regenerating axons extended to this position of Schwann cell. It was also found that the number of axons was increased by Gal1 (1–134). Table 2 shows the measurements of the number of regenerating axons using cross-sectioned sections at two positions, 0.5 mm and 1.0 mm from the transected nerve end. Average number of regenerating axons at the position 0.5 mm from the transected nerve end was 241 for the control, and 882 for the Gal1 (1–134)-administered group; that at 1.0 mm from the transected nerve end was 52 for the control, but as high as 302, significantly increased for the Gal1 (1–134)-administered group. As described above, in the Gal1 (1–134)-administered group, migration of cells, mainly Schwann cell, from the transected nerve end was promoted, as well as the elongation of regenerating axons was promoted and the number of the same was increased. It was clearly shown that Gal1 (1–134) was a useful in vivo as a nerve regeneration-promoting factor.

TABLE 1

Migration distance of migrating cells from the transected nerve end

|  | Day | Number of tests | Average migration distance of aletocyte from transected end (mm) |
|---|---|---|---|
| Control | Day 7 | 11 | 0.7 ± 0.2 |
|  | Day 10 | 8 | 1.2 ± 0.4 |
| Gal1 (1–134) | day 7 | 5 | 1.1 ± 0.1 |
|  | Day 10 | 7 | 1.9 ± 0.5 |

Unpaired Student's t-test: day 7: $p < 0.001$; day 10: $p < 0.01$.

TABLE 2

Number of neurofilament positive axons

|  | Test number | Distance from transected nerve end | |
|---|---|---|---|
|  |  | 0.5 mm | 1.0 mm |
| Control | No. 134 | 126 | 50 |
|  | No. 135 | 173 | 44 |
|  | No. 158 | 489 | 167 |
|  | No. 159 | 157 | 41 |
|  | No. 161 | 242 | 68 |
|  | No. 164 | 395 | 0 |
|  | No. 182 | 108 | 0 |
| control | average | 241 ± 135 | 52 ± 52 |
| Gal1 (1–134) | No. 139 | 894 | 555 |
|  | No. 160 | 444 | 126 |
|  | No. 163 | 387 | 86 |
|  | No. 171 | 1374 | 795 |
|  | No. 174 | 432 | 137 |
|  | No. 175 | 1766 | 114 |
| Gal1 (1–134) | average | 882 ± 526 | 302 ± 273 |

Unpaired Student's t-test: 0.5 mm: $p < 0.01$; 1.0 mm: $p < 0.05$.

Example 20

Construction of E. coli Expression Vector for a Fusion Protein of Glutathione-S-Transferase (GST) and Human Galectin-1 (Amino Acids 1–134) (Hereinafter, Referred to as "GST-Gal1 (1–134)")

GST-Gal1 (1–134) was expressed as described below using pGEX-5X-2 (manufactured by Pharmacia), an expression vector for a fusion protein with glutathione-S-transferase (GST). First, PCR was performed using pEFGal1 as a template and using two PCR primers, HLEG11 and HLEG13. PCR was performed for 25 cycles after 5 minutes at 94° C., each cycle consisting of 30 seconds at 94° C./30 seconds at 60° C./1 minute at 72° C. for synthesis; followed by 5 minutes at 72° C. for reaction. The amplified fragment was digested with BamHI and NotI, subjected to electrophoresis using 0.8% agarose gel, thereby collecting a fragment of approximately 420 bp. The fragment was purified using Prep-A-Gene DNA Purification Kit, and linked to pGEX-5X-2 that had been digested with BamHI and NotI. E. coli DH5 α was used as a host cell. A clone pGEXGal1 (1–134) having a correct nucleotide sequence of human galectin-1 cDNA (SEQ ID NO:8; the nucleotide sequence from BamHI to NotI of the vector) was selected by analysis of the nucleotide sequence. The selected clone was used as a transformant for expressing GST-Gal1 (1–134). Sequences of the PCR primers used are as follows:

HLEG11: 5'-GAGAGAGGATCCCCATGGCTTGTGGT CTGGTCGC-3' (SEQ ID NO: 50; BamHI site was added to the 5' end of GENBANK ACCESSION NO. J04456, 50–69, so that the primer could be linked to GST-Tag in frame);

HLEG13: 5'-AGAGTGCGGCCGCTTATCAGTCAAAG GCCACACATTTG-3' (SEQ ID NO: 51; NotI site was added to the 5' end of GENBANK ACCESSION NO. J04456, 436457).

This expression plasmid contained GST protein followed by factor Xa recognition sequence, and a sequence encoding human galectin-1 (amino acids 1–134) [The amino acid sequence from the factor Xa recognition sequence to human galectin-1 (amino acid 1–134) is shown in SEQ ID NO:9.].

Example 21

Construction of E. coli Expression Vector for a Fusion Protein of Glutathione-S-Transferase (GST) and Human Galectin-1 (Amino Acid 1–134) in Which Cys at Position 2 was Converted to Ser GST-Gal1 (2/Ser) was expressed as described below using pGEX-5X-2 (manufactured by Pharmacia), an expression vector for a fusion protein with glutathione-S-transferase (GST). First, PCR was performed using pGEX-Gal1 (1–134) as a template and using two PCR primers, HLEG15 and HLEG23. PCR was performed for 25 cycles after 5 minutes at 94° C., each cycle consisting of 30 seconds at 94° C./30 seconds at 55° C./1 minute at 72° C. for synthesis; followed by further 5 minutes at 72° C. The amplified fragment was digested with BamHI and NotI, subjected to electrophoresis using 2% agarose gel, thereby collecting a fragment of approximately 420 bp. The fragment was purified using Prep-A-Gene DNA Purification Kit, and linked to pGEX-5X-2 that had been digested with BamHI and NotI. E. coli DH5 was used as a host cell. A clone pGEXGal1 (2/Ser) having a nucleotide sequence of human galectin-1 cDNA, in which nucleotide No. 56 (GENBANK ACCESSION NO. J04456) had been converted to A, and nucleotide No. 58 (GENBANK ACCESSION NO. J04456) to C (the nucleotide sequence from BamHI to NotI of the vector was the same as that in SEQ ID NO:8, except that T at the 15-position was changed to A, T at the 17-position to C, respectively) was selected by analysis of the nucleotide sequence. The selected clone was used as a transformant for expressing GST-Gal1 (2/Ser). Sequences of the PCR primers used herein are as follows:

HLEG15: 5'-GAGAGAGGATCCCCATGGCTAGCGGT CTGGTCG-3' (SEQ ID NO: 64) (BamHI site was added to the 5' end of GENBANK ACCESSION NO. J04456, 50–68, so that the primer could be linked in frame to GST-Tag. In addition, nucleotide No. 56 was converted to A, and 58 to C).

HLEG23: 5'-AGAGAGCGGCCGCTTATCAGTCAAAG GCCACACATTT-3' (SEQ ID NO: 53; NotI site was added to the 5' end of the complementary strand of GENBANK ACCESSION NO. J04456, 437–457).

This expression plasmid contained GST protein followed by factor Xa recognition sequence, and a sequence encoding human galectin-1 variant [The amino acid sequence from the factor Xa recognition sequence to the human galectin-1 variant was the same as shown in SEQ ID NO:9 except that Cys at the 10-position was changed to Ser].

Example 22

Construction of E. coli Expression Vector for a Fusion Protein (Hereinafter Referred to as "GST-Gal1 (all/Ser)") of Glutathione-S-Transferase (GST) and Human Galectin-1 (Amino Acids 1–134) in Which all Cys Residues Were Converted to Ser Residues GST-Gal1 (all/Ser) was expressed as described below using pGEX-5X-2 (manufactured by Pharmacia), an expression vector for a fusion protein with glutathione-S-transferase (GST). Six Cysteine residues were present in human galectin. First, to convert Cys at the 130-position in SEQ ID NO:1 to Ser, two synthetic oligomers, HLEG21 and HLEG22, were annealed (5 minutes at 99° C./5 minutes at 80° C./5 minutes at 70° C./5 minutes at 60° C./5 minutes at 50° C./5 minutes at 40° C./5 minutes at 30° C.), and then linked to pGEX-5X-2 that had been digested with EcoRI and NotI. E. coli DH5 was used as a host cell. Of nucleotide sequences downstream of EcoRI located at nucleotide No. 366 of human galectin-1 cDNA (GENBANK ACCESSION NO. J04456), clone pGEXGal1 (all/Ser-3') (a sequence from EcoRI site to Not I site is shown in SEQ ID NO:10) having a sequence wherein T of nucleotide No. 440 (GENBANK ACCESSION NO. J04456) was converted to A, T of nucleotide No. 442 (GENBANK ACCESSION NO. J04456) to C, was selected by analysis of the nucleotide sequence. Synthetic oligomer sequences used are as follows:

HLEG21: 5'-AATTCAAGTTCCCCAACCGCCTCAACC TGGAGGCCATCAACTACATGGCAGCTGACGGTG ACTTCAAGATCAAAAGCGTGGCCTTGACTGATA AGC-3' (SEQ ID NO: 54; Not I site was added to the 3' end of GENBANK ACCESSION NO. J04456, 366–457; T of nucleotide No. 440 was converted to A, T of nucleotide No. 442 to C;).

HLEG22: 5'-GGCCGCTTATCAGTCAAAGGCCACGCT TTTGATCTTGAAGTCACCGTCAGCTGCCATGTAG TTGATGGCCTCCAGGTTGAGGCGGTTGGGGAAC TTG-3' (SEQ ID NO:55; NotI site was added to the 5' end of the complementary strand of GENBANK ACCESSION NO. J04456, 370–457; Antisense, A, of nucleotide No. 440, was converted to T, and antisense, A, of nucleotide No. 442, to G).

The remaining 5 Cysteine residues were converted to Serine residues as described below. PCR was performed using 2 ng of pGEXGal1 (1–134) as a template and using 5 pmol each of synthesized primers, HLEG16 and HLEG18. Briefly, the PCR was performed in a volume of 50 µl by GeneAmp™ PCR System 2400 (manufactured by Perkin-Elmer Corporation) using AmpliTaq™ DNA polymerase (manufactured by Perkin-Elmer Corporation). The reaction cycle was repeated 25 times after 5 minutes at 94° C., each consisting of 30 seconds at 94° C./2 minutes at 72° C. for synthesis; followed by further 5 minutes at 72° C. Furthermore, PCR was performed under the same conditions above using pGEXGal1(1–134) as a template and using 5 pmol each of synthesized primers, HLEG17 and HLEG20. After mixing the above two reaction solutions, PCR reaction was performed for 5 times, each cycle consisting of 30 seconds at 94° C. and 2 minutes at 72° C. for synthesis. Then PCR was performed in a volume of 100 µl using 1 µl of the resulting reaction solution as a template, and using 20 pmol each of synthesized primers, HLEG15 and HLEG19. The PCR reaction was performed for 25 times, each consisting of 30 seconds at 94° C./30 seconds at 55° C./1 minute at 72° C. for synthesis; followed by further 5 minutes at 72° C. The amplified fragment was digested with EcoRI and BamHI, subjected to electrophoresis with 2% agarose gel, thereby recovering a fragment of approximately 330 bp. Then the fragment was purified with Prep-A-Gene DNA Purification Kit, and then linked to pGEXGal1 (all/Ser-3') that had been digested with EcoRI and BamHI. E. coli DH5 was used as a host cell. Clone, pGEXGal1 (all/Ser), having a nucleotide sequence of human galectin-1 wherein all Cys had been converted to Ser (i.e., a nucleotide sequence from BamHI to NotI of the vector was the same as shown in SEQ ID NO:8 except that T at the 15-position was converted to A, T at the 17-position to C, T at the 57-position to A, T at the 135-position to A, T at the 189-position to A, T at the 273-position to A, T at the 399-position to A, and T at the 401-position to C), was selected by analysis of the nucleotide sequence. Sequences of the PCR primers used are as follows:

HLEG16: 5'-ATGGCTAGCGGTCTGGTCGCCAGCAAC CTGAATCTCAAACCTGGAGAGAGCCTFCG-3' (SEQ ID NO:56; GENBANK ACCESSION NO. J04456, 50–105. Nucleotide No. 56 was converted to A, No. 58 to C, and No. 98 to A);

HLEG17: 5'-ACCTGAGCCTGCACTTCAACCCTCGCT TCAACGCCCACGGCGACGCCAACACCATCGTGA GCAAC-3' (SEQ ID NO:57; GENBANK ACCESSION NO. J04456, 171–235. Nucleotide No.176 was converted to A, and No. 230 to A);

HLEG18: 5'-GTTGCTCACGATGGTGTTGGCGTCGCC GTGGGCGTTGAAGCGAGGGTTGAAGTGCAGGCT CAGGT-3' (SEQ ID NO:58; complementary strand of GENBANK ACCESSION NO. J04456, 171–235. Antisense, A, of nucleotide No. 176, was converted to T, and antisense, A, of No. 230, to T);

HLEG19: 5'-AACTTGAATTCGTATCCATCTG-3' (SEQ ID NO:59; complementary strand of GENBANK ACCESSION NO. J04456, 354–375);

HLEG20: 5'-AACTTGAATTCGTATCCATCTGGCAGCT TGACGGTCAGGTTGGCCTGGTCGAAGGTGATGC TCAC-3' (SEQ ID NO:60; complementary strand of GENBANK ACCESSION NO. J04456, 311–375. Antisense, A, of nucleotide No. 314, was converted to T).

The expression plasmid contained a sequence encoding GST protein followed by a factor Xa recognition sequence, and a sequence encoding human galenctin-1 in which all the cysteine residues were converted to Serine residues (The amino acid sequence from the factor Xa recognition sequence to human galectin-1 variant was the same as shown in SEQ ID NO: 9 except that all the cysteine residues were converted to serine residues).

Example 23

Expression of GST Fusion Protein (GST-Gal1 (1–134)) in E. coli and Removal of GST Portion by Factor Xa, and Purification of Gal1 (1–134) [GIPM-Gal1 (1–134)] Having GlyIleProMet (SEQ ID NO: 61) Added to the N-Terminus First, the clone obtained in Example 20 was streaked onto the surface of an LB agar plate containing 50 µg/ml of ampicillin, and then cultured overnight at 37° C., allowing the colony formation. One of the resulting colonies was shake-cultured in 50 ml of an LB medium containing 50 μg/ml of Ampicillin. Subsequently the culture was added to 1000 ml of an LB medium containing 50 μg/ml of ampicillin at an initial $OD_{600}$ of 0.2, and shake-cultured at 37° C. until the $OD_{600}$ reached 0.5–0.6. Then IPTG (isopropylthiogalactosid) was added at a final concentration of 0.1 mM, followed by 3 hours shake-cultur, thereby inducing expression of GST-Gal1 (1–134). One L of the cell culture solution was centrifuged at 10000 G for 30 minutes to obtain a pellet of cells expressing GST-Gal1 (1–134) fusion protein. The pellet was suspended in 20 ml of PBS, and sonicated with cooling so that the cells were disrupted. The cell-disrupted solution was centrifuged at 10000 G for 30 minutes, thereby collecting the supernatant containing GST-Gal1 (1–134) fusion protein as a soluble protein. The collected supernatant was loaded to a glutathione-Sepharose 4B column (manufactured by Pharmacia; φ 3 cm×5 cm) equilibrated with PBS. The elution buffer was exchanged with 50 mM Tris-HCl buffer (pH 8.0) containing 1 mM calcium chloride and 100 mM NaCl, for the sake of thorough washing. Then 400 units factor Xa was loaded to the column which was allowed to stand overnight at room temperature. Next, GIPM-Gal1 (1–134) that had been cleaved with the factor Xa was eluted at a flow rate of 1 ml/min with 50 mM Tris-HCl buffer (pH 8.0) containing 1 mM calcium chloride and 100 mM NaCl. The eluate was fractionated into 3 ml each and each of the fractions was analyzed with electrophoresis. The fraction in which a band suspected to be GIPM-Gal1 (1–134) with a molecular weight of 14500 Da was used for the next step (12 ml). The fraction was concentrated with a ultrafiltration unit (manufactured by Amicon; membrane YM3, 25 mm in diameter), followed by buffer exchange with 20 mM Tris-HCl buffer (pH 8.0). The final solution (3 ml) was loaded at a flow rate of 0.5 ml/min at room temperature to a Shodex IEC DEAE 825 column (manufactured by Showa Denko K.K., Japan; φ8 mm×7.5 cm) equilibrated with 0% B using 20 mM Tris-HCl buffer (pH 8.0) as a solvent A and the same buffer containing 500 mM NaCl as a solvent B. After loading, the column was eluted with a 60 minutes linear gradient from 0% B to 60% B. The eluate was fractionated into 1 ml each, and analyzed by electrophoresis. As a result, a band that was suspected to be GIPM-Gal1 (1–134) with a molecular weight of 14500 Da was detected in a fraction with approximately 80 mM NaCl. This fraction was used for the next step. The fraction (1 ml) was loaded at a flow rate of 0.5 ml/min at room temperature to a TSKgel Phenyl-5PW RP column (manufactured by TOSOH CORPORATION, Japan; φ 4.6 mm×7.5 cm) equilibrated with 20% B, using 0.1% TFA as a solvent A and 80% acetonitrile containing 0.085% TFA as a solvent B. After loading, the column was eluted with a 40 minutes linear gradient from 20% B to 80% B. The eluate was fractionated into 1 ml each, then analyzed by electrophoresis. Only a band that was suspected to be GIPM-Gal1 (1–134) with a molecular weight of 14500 Da was detected in a fraction with approximately 30% acetonitirle. Thus purification was completed. To confirm this band is of GIPM-Gal1 (1–134), N-terminal amino acid sequence analysis was performed using a protein sequencer (manufactured by Perkin-Elmer Corporation; type 492). The detected N-terminal amino acid sequence was as shown below (X denotes unidentified amino acids):
GlyIleProMetAlaXGlyLeuValAlaSerAsnLeuAsnLeu (SEQ ID NO: 62).

This sequence was identical to the N-terminal amino acid sequence of GIPM-Gal1 (1–134) as designed. It was confirmed that the protein purified by the TSKgel Phenyl-5PW RP column was GIPM-Gal1 (1–134).

Similarly, the clone obtained in Example 21 was expressed in *E. coli*, and GST-Gal1 (2/Ser) was obtained. Then the product was cleaved with factor Xa to obtain GIMP-Gal1 (referred to as GIPM-Gal1 (2/Ser)), in which Cys at the 2-position was replaced by Ser.

Furthermore, the clone obtained in Example 22 was expressed in *E. coli*, and GST-Gal1 (all/Ser) was obtained. Then the product was cleaved with factor Xa to obtain GIMP-Gal1 (referred to as GIPM-Gal1 (all/ser)), in which all of six cysteine residues was replaced by serine residues.

All references including patents and patent applications cited herein are incorporated herein by reference in their entirety.

What is claimed is:

1. An isolated protein which possesses nerve regeneration-promoting effect, having the amino acid sequence shown in SEQ ID NO:1 or an amino acid sequence that has a 90% or more homology at the amino acid level with the amino acid sequence shown in SEQ ID NO:1, and carries a disulfide bond(s) at least between Cys at the 16-position (Cys 16) and Cys at the 88-position (Cys 88) among cysteine residues at the 2-position (Cys 2), 16-position (Cys 16), 42-position (Cys 42), 60-position (Cys-60), 88-position (Cys 88) and 130-position (Cys 130).

2. A protein of claim 1 which carries disulfide bonds between cysteine residues of any one of combinations (1) Cys 16–Cys 88, Cys 2–Cys 130 and Cys 42–Cys 60, or (2) Cys 16–Cys 88, Cys 2–Cys 60 and Cys 42–Cys 130, or (3) Cys 16–Cys 88, Cys 2–Cys 42 and Cys 60–Cys 130.

3. A protein of claim 2, which comprises mixture of at least two groups out of said (1), (2), and (3).

4. A protein of claim 3, which contains 50% or more of said (1).

5. A protein of claim 1, wherein the N-terminal end is acylated.

6. A protein of claim 1, wherein $Met^{-2} Lys^{-1}$ or $Met^{-1}$ is added to the N-terminal end.

7. A protein of claim 1, which is covalently bound to a water-soluble polymer.

8. A protein of claim 7, wherein the water-soluble polymer is polyethylene glycol.

9. A process for producing a protein of claim 1, comprising the steps of loading a substance containing said protein to an affinity column having an antibody or antibodies to said protein bound thereto, allowing said protein to be adsorbed, subsequently eluting said protein, and if necessary oxidizing said protein.

10. A method for regenerating an injured nerve, comprising administering as the active ingredient an isolated galectin-1 that comprises the amino acid sequence as shown in SEQ ID No. 1.

11. A method for regenerating injured nerve, comprising administering as the active ingredient a derivative of isolated galectin-1 having a 90% or more homology at the amino acid level with the amino acid sequence shown in SEQ ID NO: 1 and possessing a nerve regeneration-promoting effect, including regeneration of axons or repair of nerve tissues.

12. The method of claim 11, further comprising administering a pharmaceutically acceptable carrier.

13. The method of claim 11, further comprising administering a pharmaceutically acceptable carrier.

14. The method of claim 10, wherein said galectin-1 possesses lectin activity.

15. The method of claim 10, wherein said galectin-1 possesses almost no lectin activity or no lectin activity.

16. The method of claim 10, wherein said galectin-1 has an acylated N-terminal end.

17. The method of claim 10, wherein said galectin-1 is covalently bound to a water-soluble polymer.

18. The method of claim 17, wherein said water soluble polymer is polyethylene glycol.

19. The method of claim 10, wherein the galectin-1 carries a disulfide bond(s) at least between Cys at the 16-position (Cys 16) and Cys at the $^{88}$-position (Cys 88) among cysteine residues at the 2-position (Cys 2), 16-position (Cys 16), 42-position (Cys 42), 60-position (Cys-60), 88-position (Cys 88) and 130-position (Cys 130) in the amino acid sequence shown in SEQ ID NO:1.

20. The method of claim 19, wherein the galectin-1 carries disulfide bonds between any one of combinations (1) Cys 16–Cys 88, Cys 2–Cys 130 and Cys 42–Cys 60, or (2) Cys 16–Cys 88, Cys 2–Cys 60 and Cys 42–Cys 130, or (3) Cys 16–Cys 88, Cys 2–Cys 42 and Cys 60–Cys 130.

21. The method of claim 20, wherein the galectin-1 comprises a mixture of at least two groups out of said (1), (2) and (3).

22. The method of claim 21, wherein said mixture contains 50% or more of said (1).

23. The method of claim 10, further comprising administering at least one other neurotrophic factor, or paraneural cells, or an extracellular matrix containing said factor.

24. The method of claim 23, wherein said extracellular matrix is laminin, collagen, fibronectin or thrombospondin.

25. The method of claim 23, wherein said paraneural cells are Schwann cells, fibroblasts, satellite cells, macrophage or glia cells.

26. The method of claim 11, wherein said galectin-1 derivative possesses lectin activity.

27. The method of claim 11, wherein said galectin-1 derivative possesses almost no lectin activity or no lectin activity.

28. The method of claim 11, wherein said galectin-1 derivative has an acylated N-terminal end.

29. The method of claim 11, wherein said galectin-1 derivative is covalently bound to a water-soluble polymer.

30. The method of claim 11, further comprising administering at least one other neurotrophic factor, or paraneural cells, or an extracellular matrix containing said factor.

31. The method of claim 11, Herein the galectin-1 derivative carries a disulfide bond(s) at least between Cys at the 16-position (Cys 16) and Cys at the 88-position (Cys 88) among cysteine residues at the 2-position (Cys 2), 16-position (Cys 16), 42-position (Cys 42), 60-position (Cys-60), 88-position (Cys 88) and 130-position (Cys 130) in the amino acid sequence shown in SEQ ID NO:1.

32. The method of claim 31, wherein the galectin-1 derivative carries disulfide bonds between any one of combinations (1) Cys 16–Cys 88, Cys 2–Cys 130 and Cys 42–Cys 60, or (2) Cys 16–Cys 88, Cys 2–Cys 60 and Cys 42–Cys 130, or (3) Cys 16–Cys 88, Cys 2–Cys 42 and Cys 60–Cys 130.

33. The method of claim 32, wherein the galectin-1 derivative comprises a mixture of at least two groups out of said (1), (2) and (3).

34. The method of claim 30, wherein said extracellular matrix is laminin, collagen, fibronectin or thrombospondin.

35. The method of claim 30, wherein said paraneural cells are Schwann cells, fibroblasts, satellite cells, macrophage or glia cells.

36. The method of claim 28, wherein said N-terminal end of said galectin-1 derivative is acetylated.

37. The method of claim 16, wherein said N-terminal end of said galectin-1 is acetylated.

38. The method of claim 29, wherein said water-soluble polymer is polyethylene glycol.

39. The method of claim 33, wherein said mixture contains 50% or more of said (1).

40. The method of claim 10, wherein said galectin-1 is packed in a tube made of biocompatible material.

41. The method of claim 11, wherein said galectin-1 derivative is packed in biocompatible material.

* * * * *